(12) United States Patent
Yin et al.

(10) Patent No.: US 8,933,302 B2
(45) Date of Patent: Jan. 13, 2015

(54) JATROPHA CURCAS CURCIN GENES, TISSUE-SPECIFIC PROMOTERS AND GENERATION OF CURCIN-DEFICIENT TRANSGENIC JATROPHA PLANTS

(75) Inventors: Zhong Chao Yin, Singapore (SG); Li Fang Wu, Singapore (SG); Hui Zhu Mao, Singapore (SG); Cheng Xiang Qiu, Singapore (SG)

(73) Assignee: Temasek Life Sciences Laboratory Liimited, Singapore (SG)

( * ) Notice: Subject to any disclaimer, the term of this patent is extended or adjusted under 35 U.S.C. 154(b) by 539 days.

(21) Appl. No.: 13/375,594

(22) PCT Filed: Jun. 2, 2010

(86) PCT No.: PCT/SG2010/000206
§ 371 (c)(1),
(2), (4) Date: Dec. 1, 2011

(87) PCT Pub. No.: WO2010/140981
PCT Pub. Date: Dec. 9, 2010

(65) Prior Publication Data
US 2012/0073018 A1    Mar. 22, 2012

Related U.S. Application Data

(60) Provisional application No. 61/184,416, filed on Jun. 5, 2009.

(51) Int. Cl.
*C12N 15/82* (2006.01)
*A01H 5/10* (2006.01)
*C07H 21/04* (2006.01)
*C12N 15/87* (2006.01)
*C07K 14/415* (2006.01)

(52) U.S. Cl.
CPC .......... *C07K 14/415* (2013.01); *C12N 15/8218* (2013.01); *C12N 15/8225* (2013.01); *C12N 15/8234* (2013.01); *C12N 15/8238* (2013.01); *C12N 15/8239* (2013.01); *C12N 15/8242* (2013.01); *C12N 15/8251* (2013.01); *C12N 2310/14* (2013.01)

USPC ........ 800/287; 536/24.1; 435/320.1; 435/419

(58) Field of Classification Search
None
See application file for complete search history.

(56) References Cited

PUBLICATIONS

Qin et al. 2009, Planta 230:387-395.*
Genbank Accession No. EU195892, 2007.*
Qin, X. et al., "Isolation and Characterization of a Curcin Promoter from *Jatropha curcas* L. and Its Regulation of Gene Expression in Transgenic Tobacco Plants," Plant Mol. Biol. Rep., Published online Dec. 30, 2008, vol. 27, pp. 275-281.
Qin, X. et al., "Stress-induced curcin-L promoter in leaves of *Jatropha curcas* L. and characterization in transgenic tobacco," Planta., Published online May 28, 2009, vol. 230, pp. 387-395.
GenBank Accession No. EF612740, Jun. 9, 2007, Sequence shares 96.46% identity with residues 1751 to 2087 of SEQ ID No. 8.
GenBank Accession No. EF612741, Jun. 9, 2007, Sequence shares 93.63% identity with residues 2944 to 3170 of SEQ ID No. 7 and 96.46% identity with residues 1751 to 2087 of SEQ ID No. 8.
GenBank Accession No. EF612739.1 (Jun. 9, 2007), *Jatropha curcas* clone CP1 curcin ribosome-inactivating protein gene, promoter region, 1 page.
Intellectual Property Office of Singapore (Written Opinion and Search Report from Hungarian Intellectual Property Office) dated May 2, 2014, Patent Application No. 2011087848, Title: *Jatropha curcas* Curcin Genes, Tissue-Specific Promoters and Generation of Curcin-Deficient Transgenic Jatropha Plants, 17 pages.

* cited by examiner

*Primary Examiner* — Li Zheng
(74) *Attorney, Agent, or Firm* — Rothwell, Figg, Ernst & Manbeck P.C.

(57) ABSTRACT

The present invention relates to the isolation of *Jatropha curcas* curcin genes and tissue-specific promoters and to the production of curcin-deficient *Jatropha* plants. More specifically, the present invention relates to the isolation of *Jatropha cur

FIG. 2

```
 -180 TGGATTTTCAATAATTCTTTTTCATTGGGATATGTTGTTGTTTGTCTTTATTTTACATCT
 -120 TATGAAACTGTCGTTTGGTTGCTAATAATAATAATAATAATAAAGAAAAAAAATTGA
  -60 CAAAATAAAGGGCCGGGAAGGCAGTTTCCCTATAAAAGCAGGTGATGGGGGAAGGCAAAA
    1 GACCATCTCTTGCTCTCTTCTTCTTTACTTCCCCGTTTGCTCAGTTGCTTTCTTTgtaag
   61 taatatagaagcctctgcccttctttgttgttgacaaattccatttttttgttttactatt
  121 agcatgttaatttctagcttctggaaatgagtttattatcctttatatgataaacttgtg
  181 accattctatctcttttttaattattttttataattttatgcaattctattaaaataatcgt
                          CF2
  241 attcgtataat gatatttgtgtttcttcata caactggacagGTGAAATCAATATGAAAG
                                                              M  K  G
  301 GTGGAAAGATGAATCTCTCCATTATGGTGGCTGCATGGTTTTGCTGGAGTAGTATTATAT
         G  K  M  N  L  S  I  M  V  A  A  W  F  C  W  S  S  I  I  F
  361 TCGGATGGGCATCGGCTAGGGAAATAGTTTGTCCATTCTCATCAAACCAAAACTACAAAG
         G  W  A  S  A  R  E  I  V  C  P  F  S  S  N  Q  N  Y  K  A
  421 CTGGTTCCCCTCCAACTTTAACCATTACTTATGACGCTACTACTGATAAGAAAAACTACG
         G  S  P  P  T  L  T  I  T  Y  D  A  T  T  D  K  K  N  Y  A
  481 CCCAGTTCATTAAAGATCTAAGAGAAGCATTTGGCTTCAGTTATTCAAGCCATGAAATAC
         Q  F  I  K  D  L  R  E  A  F  G  F  S  Y  S  S  H  E  I  P
  541 CAGTCTTACGGGCCACAGTTGCTCCAAATCAGAAATTTATTGTAGCCAAAGTCATAAATG
         V  L  R  A  T  V  A  P  N  Q  K  F  I  V  A  K  V  I  N  V
  601 TAGCGAATTTAGAAGTATCATTAGGATTAAACGTCGTTAATGCGTATTTAGTGGGTTATA
         A  N  L  E  V  S  L  G  L  N  V  V  N  A  Y  L  V  G  Y  K
  661 AGGTAGGAGGTACTTCCTATTTCTTTAACGATCCGGAATCTTTGGCTGATGCAAAAACAT
         V  G  G  T  S  Y  F  F  N  D  P  E  S  L  A  D  A  K  T  Y
  721 ATCTTTTCACAGACACAAAGCAACAAACGCTATCATTTACTGGTAGCTATGCAGATTTTC
         L  F  T  D  T  K  Q  Q  T  L  S  F  T  G  S  Y  A  D  F  L
  781 TATCTAGGGCAAACGTACACAGAGAGGATGTGGATTTAGGGGTGCAGGCATTAGATAATT
         S  R  A  N  V  H  R  E  D  V  D  L  G  V  Q  A  L  D  N  Y
  841 ACATATATACACTTGAAAAAGTTCAAAGCCAGCAGACATTGCTAAACCTCTAGTTGGTT
         I  Y  T  L  E  K  S  S  K  P  A  D  I  A  K  P  L  V  G  F
  901 TTATCGAAATGGTTCCAGAGGCAGCAAGATTCAAATATATTGAGAAAAAAGTATTAAGTC
         I  E  M  V  P  E  A  A  R  F  K  Y  I  E  K  K  V  L  S  Q
  961 AAATTAGCAAAACCTTTAGGCCGGGTGGTGACATAATTAGCCTTGAGAACAACTGGGGAG
         I  S  K  T  F  R  P  G  G  D  I  I  S  L  E  N  N  W  G  D
 1021 ACCTCTCTTATCAAATACAGAAATGTGTAAATGGTGTATTTCTGAAGCCAGTTCAATTAC
         L  S  Y  Q  I  Q  K  C  V  N  G  V  F  L  K  P  V  Q  L  Q
 1081 AACGTGAAAACTATACCAATATCCTAGTGAACAATGTCACCCAAGTAGCAGGTGTCATGG
         R  E  N  Y  T  N  I  L  V  N  N  V  T  Q  V  A  G  V  M  G
 1141 GAGTCTTGTTGAATGCAGTCAATTACAAAGTCTGAATGGAAGAAATTATTTTCAACTACC
         V  L  L  N  A  V  N  Y  K  V  *
 1201 AAAAGTGGCTGCCATGGCTTTAATCCTACTTTTGCTCTATATATAGAGT AGCATAAATAA
                                                         ←――――――
                                                           CR2
 1261 AGGACAACAAA TTT ATTATTATTGTTGCTAATGCTATA TGCTATTTCCCTGTAATATCCT
                      ←――――――――――――――――――
                              C1SR
 1321 CATCTTTCCAATGTATGAATATGATGATGAATTATATATGACAAATAAAGTTTCTACTAG
 1381 TTCTTAAT
```

FIG. 3

```
 -180 CCTTGCATTTTCAATAATTCTTTTTCATTGGGATTTGTTGTTGTTTGTCTTTATTTTACA
 -120 TCTTATGAAACTGTCGTTTGGTAGCTAATAATAATAATAATAATAATAATAATAAAGAAA
  -60 AAAAATTGACAAAATAAAGGGCAGTTTCCCTATAAAAGCAGGTGATGGGGGAAGGCAAAA
    1 GACCATCTCTCGCTTTCTTTgtaagtaatagtgaagcctctgcccttcttttttgttgac
   61 aaattccattttttgttttactaatagcatgttaatttctagcttctggaaatgagttta
  121 ttatcctttatatgataaacttgtgaacattctatctcttttttaattatttttataattt
                                                   ─────CF2────────▶
  181 tatgcaaagctattaaaataatcgtattcgtataat*gatatttgtgtttcttcat*acaac
  241 tggacagGTGAAATCAATATGAAAGGTGGCAAGATGAACCTCTCTATTATGGTGGCTGCA
                         M  K  G  G  K  M  N  L  S  I  M  V  A  A
  301 TGGTTTTGCTGGAGTTGTATTATATTCGGATGGGCATCGGCTAGGGAAATAGTTTGTCCA
        W  F  C  W  S  I  I  F  G  W  A  S  A  R  E  I  V  C  P
  361 TTCTCATCAAACCAAAACTACAAAGCTGGTTCCACTCCAACTTTAACCATTACTTATGAC
        F  S  S  N  Q  N  Y  K  A  G  S  T  P  T  L  T  I  T  Y  D
  421 GCTGCTGCTGATAAGAAAAACTACGCCAACTTCATTAGAGATCTAAGAGAAGCATTTGGC
        A  A  A  D  K  K  N  Y  A  N  F  I  R  D  L  R  E  A  F  G
  481 TTCAGTTATTCAAGCCATGAAATACCAGTCCTACGGGCCACGGTTGCTGCAAATCAGAAA
        F  S  Y  S  S  H  E  I  P  V  L  R  A  T  V  A  A  N  Q  K
  541 TTTATTGTAGCCAAAGTCATAAATGTAGCGAATTTAGAAGTATCATTAGGATTAAACGTC
        F  I  V  A  K  V  I  N  V  A  N  L  E  V  S  L  G  L  N  V
  600 GTTAATGCATATTTAGTGGCTTATAAGGCAGGAGGTACATCCTATTTCTTTAACGATCCC
        V  N  A  Y  L  V  A  Y  K  A  G  G  T  S  Y  F  F  N  D  P
  661 GAATCTTTGGCTGATGCAAAAAAATATCTTTTCACAGACACAAAGCAACAAACGCTATCA
        E  S  L  A  D  A  K  K  Y  L  F  T  D  T  K  Q  Q  T  L  S
  721 TTTACTGGTAGCTATGCAGATTTTCTATCTAGGGCAAACGTACACAGAGAGGATGTGGAT
        F  T  G  S  Y  A  D  F  L  S  R  A  N  V  H  R  E  D  V  D
  781 TTAGGGGTGCTGGCATTAGATAATTACATATATATACTTCACAAAAGTTCTCAACCAGCA
        L  G  V  L  A  L  D  N  Y  I  Y  I  L  H  K  S  S  Q  P  A
  841 GACATTGCTAAACCTCTAGTTGGTTTTATCGAAATGGTTCCAGAGGCAGCAAGATTCAAA
        D  I  A  K  P  L  V  G  F  I  E  M  V  P  E  A  A  R  F  K
  901 TATATTGAGAAAAAGTATTAACTCAAATTAGCGAAACCTTTAGGCCGCGTGGTGTCATA
        Y  I  E  K  K  V  L  T  Q  I  S  E  T  F  R  P  R  G  V  I
  961 ATTAGCCTTGAGAACAACTGGGGAGACCTCTCTTATCAAATACAGAAATCTGTAAATGGT
        I  S  L  E  N  N  W  G  D  L  S  Y  Q  I  Q  K  S  V  N  G
 1021 ATATTTCTGAAGCCAGTTCAATTGCAACGTGAAAACTATACCAATATCCTAGTGAACAAT
        I  F  L  K  P  V  Q  L  Q  R  E  N  Y  T  N  I  L  V  N  N
 1081 GTCACCCAAGTAACAGGTCTCATGGGAGTCTTGTTGAATGCAGTCAATTACAAAGTCTCA
        V  T  Q  V  T  G  L  M  G  V  L  L  N  A  V  N  Y  K  V  S
 1141 ATGGAAGAAATTATTTTCAACTACCAAAAGTGGCTGCCATGGCTTTAATCCTACTTTTGC
        M  E  E  I  I  F  N  Y  Q  K  W  L  P  W  L  *
 1201 TCTATATATAGTAGCATAAATAAAGGACAACAAATTTAGTATTATTGTTGTTGTCCAAAC
                 ◀─────────CR2─────────
 1261 ATGTTGCCAATGATATATGCTATTTCCCTGTAATATCCTCATCTTTCCAATGTATGAATA
 1321 TGATGATGTATTATATATGACAAATAAAGTTTCTACTAGTTCTTAAT
```

FIG. 4

```
 -180 TTCTTTTTTTTTTTTTTTTTGACAGTTGTTATTGTTTGTCTTTATTTTTACATCTTATGA
 -120 AACTGTCGTTTGGTAGCTAATAATCAAAATAATAATAAAAATAATAATAATAAAGAAAA
  -60 AAAAATTGACAAAATAAAGGGCAGTTTCCCTATAAAAGCAGGTGATGGGGGAAGGCAAAA
    1 GACCATCTCTCGCTCTCTTCTTCTTTACTTCCCCGTTTGCTCAGTTGCTTTCTTTgtaag
   61 taatattgaagcctctgcccttcttttttgttgacaaattccatttttttgttttactaa
  121 tagcatgttaatttctagcttctggaaatgagtttattatactttatatgataaacttgt
  181 gaccattctatctcttttaatcatttttataattttatgcaaatctattataataatcg
                             CF2
  241 tattcgtataatgatatttgtgtttcttcatacaactggacagGTGAAATCAATATGAAA
                                                              M  K
  301 GGTGGAAAGATGAACCTCTCCATTATGGTGGCTGCCTGGTTTTGCTGGAGTAGTATTATA
       G  G  K  M  N  L  S  I  M  V  A  A  W  F  C  W  S  S  I  I
  361 TTCGGATGGGCATCGGCTAGGGAAATAGTTTGTCCATTCTCATCAAACCAAAACTACAAA
       F  G  W  A  S  A  R  E  I  V  C  P  F  S  S  N  Q  N  Y  K
  421 GCTGGTTCCACTCCAACTTTAGCCATTACTTATGACGCTACTACTGATAAGAAAAACTAC
       A  G  S  T  P  T  L  A  I  T  Y  D  A  T  T  D  K  K  N  Y
  481 GCCCAGTTCATTGAAGATCTAAGAGAAGCATTTGACTTCAGTTATTTAAGCCATAAAATA
       A  Q  F  I  E  D  L  R  E  A  F  D  F  S  Y  L  S  H  K  I
  541 CCAGTCTTACGGGCCACGGTTGCTGCAAATCAGAAATTTATTGTAGCCAAAGTCATAAAT
       P  V  L  R  A  T  V  A  A  N  Q  K  F  I  V  A  K  V  I  N
  601 TCTGGGGACATAGAAGTATCAGTAGGATTAAACGTCATTAATGCATATCTAGTGGCTTAT
       S  G  D  I  E  V  S  V  G  L  N  V  I  N  A  Y  L  V  A  Y
  661 AAGGTAGGAAGTAATTCCTATTTCTTTAACGATTCGGAATCTTTGGCTGATGCAAAAAAA
       K  V  G  S  N  S  Y  F  F  N  D  S  E  S  L  A  D  A  K  K
  721 AATCTTTTCACAGACACAAACCAACAAACACTAGCATTTACTGGTAGCTATGCAGATTTT
       N  L  F  T  D  T  N  Q  Q  T  L  A  F  T  G  S  Y  A  D  F
  781 GAATCTAGGGCAAAGTTACATAGAGAGGAAGTGGATTTAGGAGTGGTGGCATTGGATAAT
       E  S  R  A  K  L  H  R  E  E  V  D  L  G  V  V  A  L  D  N
  841 TACGTATATACACTTGAAAAAGTTCTCAGCCAGCAGACATTGCTAAACCTCTAGTTGGT
       Y  V  Y  T  L  E  K  S  S  Q  P  A  D  I  A  K  P  L  V  G
  901 TTTATCGAAATGGTTCCAGAGGCAGCAAGATTCAAATATATTGAGAAAAAAATATCAACT
       F  I  E  M  V  P  E  A  A  R  F  K  Y  I  E  K  K  I  S  T
  961 CAAATTAGCAAAACCTTTAGGCCGCGTGGTGACATAATTAGCCTTGAGAACAACTGGGGA
       Q  I  S  K  T  F  R  P  R  G  D  I  I  S  L  E  N  N  W  G
 1021 GACCTCTCTTATCAAATACAGAAATCTGTTGATGATGTATTTCTGAAGCCAGTTCAATTG
       D  L  S  Y  Q  I  Q  K  S  V  D  D  V  F  L  K  P  V  Q  L
 1081 CAACGTGAAAACTATACCAATATCCTAGTGAACAATGTCACCCAAGTAAAAGGTCTCATG
       Q  R  E  N  Y  T  N  I  L  V  N  N  V  T  Q  V  K  G  L  M
 1141 GGAGTCTTGTTGAATGCAGTCAATTACAAAGTCTCAATGGAAGAAATTATTTTCAACGAC
       G  V  L  L  N  A  V  N  Y  K  V  S  M  E  E  I  I  F  N  D
 1201 CAAAAGTGGCTGCCATGGCTTTAATCCTACTTTTGCTCTATATATAGTAGCATAAATAAA
       Q  K  W  L  P  W  L  *                          CR2
 1261 GGACAACAAATTTAGTATTATTGTTGTTGTCCAAACATGTTGCTAATGATATATGCTCTT
                                         C2ASR
 1321 TCCCTGTAATATCCTCGTCTTTCCAATGTATGAATATGATGATGAATTATATATGACAAA
 1381 TAAAGTTTCTACTAGTTCTTAAT
```

FIG. 6

```
                    *        20         *        40         *        60         *        80
Curcin 2A  : MKGGKMNLSIMVAAWFCWSSIIFGWASAREIVCPFSSNQNYKAGSTPTLAITYDATDKKNYAQFIEDLREAFDFSYLSH :  80
ABZ04128   : MKGGKMNLSIMVAAWFCWSSIIFGWASAREIVCPFSSNQNYKAGSTPTLAITYDATDKKNYAQFIEDLREAFDFSYLSH :  80
AAR08395   : MKGGKMNLSIMVAAWFCWSSIIFGWASAREIVCPFSSNQNYKAGSTPTLAITYDATDKKNYAQFIEDLREAFDFSYLSH :  80
ABW17545   : MKGGKMNLSIMVAAWFCWSSIIFGWASAREIVCPFSSNQNYKAGSTPTLVITYDATDKKNYAQFIEDLREAFDFSYLSH :  80
Curcin 1   : MKGGKMNLSIMVAAWFCWSCIIFGWASAREIVCPFSSNQNYKAGSTPTLTITYDATDKKNYAQFIKDLREAFGFSYSSH :  80
AAL58089   : MKGGKMNLSIMVAAWFCWSCIIFGWASAREIVCPFSSNQNYKAGSTPTLTITYDAADKKNYACFIKDLREAFGFSYSSH :  80
Curcin 2   : MKGGKMNLSIMVAAWFCWSCIIFGWASAREIVCPFSSNQNYKAGSTPTLTITYDAAADKKNYANFIRDLREAFGFSYSSH :  80
AAL86778   : MKGGKMNLSIMVAAWFCWSCIIFGWASAREIVCPFSSNQNYKAGSTPTLTITYDAAADKKNYANFIRDLREAFGFSYSSH :  80

*       100         *       120         *       140         *       160
Curcin 2A  : KIPVLRATVAANQKFIVAKVINSGDIEVSVGLNVINAYLVAYKVGSNSYFFNDSESLADAKKNLFTDTNQQTLAFTGSYA : 160
ABZ04128   : KIPVLRATVAANQKFIVAKVINSGDIEVSVGLNVINAYLVAYKVGSNSYFFNDSESLADAKKNLFTDTNQQTLAFTGSYA : 160
AAR08395   : KIPVLRATVAANQKFIVAKVINSGDIEVSVGLNVINAYLIVAYKVGSNSYFFNDSESLADAKKNLFTDTNQQTLAFTGSYA : 160
ABW17545   : KIPVLRATVAANQKFIVAKVINSGDIEVSVGLNVINAYLIVAYKVGSNSYFFNDSESLADAKKNLFTDTNQQTLAFTGSYA : 160
Curcin 1   : EIPVLRATVAPNQKFIVAKVINVANLEVSLGLNVVNAYLIVGTKVGTSYFFNDSESLADAKTYLFTDTKQTLSFTGSYA : 160
AAL58089   : EIPVLRATVAPNQKFIVAKVINVANLEVSLGLNVVNAYLIVGYKVGTSYFFNDSESLADAKTYLFTDTKQTISFTGSYA : 160
Curcin 2   : EIPVLRATVAANQKFIVAKVINVANLEVSLGLNVVNAYLIVGYKAGCTSYFFNDSESLADAKKYLFTDTKKQTLSFTGSYA : 160
AAL86778   : EIPVLRATVAANQKFIVAKVINVANLEVSLGLNVVNAYLIVGYKVGTSYFFNDPESLADAKTYLFTDTKQTLSFTGSYA : 160

*       180         *       200         *       220         *       240
Curcin 2A  : DFFSRAKLHREVDLGVVALDNYVTLEKSSQPADIAKPLVGFIEMVPEAAREKYIEKKISTQISKTFRPRGDIISLENN : 240
ABZ04128   : DFFSRAKLHREVDLGVVALDNYVTLEKSSQPADIAKPLVGFIEMVPEAAREKYIEKKISTQISKTFRPRGDIISLENN : 240
AAR08395   : DFFSRAKLHKEVDLGVVALDNYVTLEKSSQPADIAKPLVGFIEMVPEAAREKYIEKKISTQISKTFRPRGDIISLENN : 240
ABW17545   : DFFSRAKLHREVDLGVVALDNYVTLEKSSQPADIAKPLVGFIEMVPEAAREKYIEKKISTQISKTFRPRGDIISLENN : 240
Curcin 1   : DFLSRANVHREDVDLGVVTLEKSSKPADIAKPLVGFIEMVPEAAREKYIEKKVLSQISKTLRPGGDIISLENN : 240
AAL58089   : DFLSRANVHREDVDLGVVTLEKKSSKPADIAKPLVGFIEMVPEAAREKYIEKKVLSQISKTLRPGGDIISLENN : 240
Curcin 2   : DFLSRANVHREDVDLGVVTLEKSKPADIAKPLVGFIEMVPEAAREKYIEKKVLTQISETFRPRGVIISLENN : 240
AAL86778   : DFLSRANVHREDVDLGVVTLEKSSKPADIAKPLVGFIEMVPEAAREKYIEKKISTQISKTFRPRGDIISLENN : 240

*       260         *       280         *       300
Curcin 2A  : WGDLSYQIQKSVDDVFLKPVQLQRENYTNILVNNVTQVKGLMGVLLNAVNMKVSMEEIIFNDQKWLPWL : 309
ABZ04128   : WGDLSYQIQKSVDDVFLKPVQLQRENYTNILVNNVTQVKGLMGVLLNAVNMKVSMEEIIFNDQKWLPWL : 309
AAR08395   : WGDLSYQIQKSVDDVFLKPVQLQRENYTNILVNNVTQVKGLMGVLLNAVNMKVSMEEIIFNDQKWLPWL : 309
ABW17545   : WGDLSYQIQKSVDDVFLKPVQLQRENYTNILVNNVTQVKGLMGVLLNAVNMKVSMEEIIFNDQKWLPWL : 309
Curcin 1   : WGDLSYQIQKCVNGVFLKPVQLQRENYTNILVNNVTQVACVMGVLLNAVNNKV---------------  : 293
AAL58089   : WGDLSYQIQKCVNGVFLKPVQLQRENYTNILVNNVTQVACVMGVLLNAVNNKV---------------  : 293
Curcin 2   : WGDLSYQIQKSVNGIFLKPVQLQRENYTNILVNNVTQVKGLMGVLLNAVNMKVSMEEIFNYQKWLPWL : 309
AAL86778   : WGDLSYQIQKSVDDVFLKPVQLQRENYTNILVNNVTQVKGLMGVLLNAVKKV---------------  : 293
```

Anti-Curcin 1

Anti-Curcin 1

JATROPHA CURCAS CURCIN GENES, TISSUE-SPECIFIC PROMOTERS AND GENERATION OF CURCIN-DEFICIENT TRANSGENIC JATROPHA PLANTS

CROSS-REFERENCE TO RELATED APPLICATION

The present application is a national stage filing under 35 U.S.C. §371 of PCT/SG2010/000206, filed on 2 Jun. 2010 which in turn claims priority to U.S. provisional patent application Ser. No. 61/184,416 filed 5 Jun. 2009, which are both incorporated herein by reference.

BACKGROUND OF THE INVENTION

The present invention relates to the isolation of *Jatropha curcas* curcin genes and tissue-specific promoters and to the production of curcin-deficient *Jatropha* plants. More specifically, the present invention relates to the isolation of *Jatropha curcas* Curcin 1, Curcin 2 and Curcin 2A. The present invention further relates to of the Curcin 1, Curcin 2A and Curcin 2 genes and more particularly to tissue specific promoters of the Curcin 1 and Curcin 2A genes. The present invention further relates to production of curcin-deficient transgenic *jatropha* plants by using RNAi technology to suppress curcin gene expression.

The publications and other materials used herein to illuminate the background of the invention or provide additional details respecting the practice, are incorporated by reference, and for convenience are respectively grouped in the Bibliography.

Tissue specific promoters are strongly desired for plant biotechnology to express gene-of-interest in the particular plant tissue at right time (Mansoor et al., 2006). Plant seed endosperm accumulates storage materials, such as starch, proteins and lipids (Berger et al., 2006; Hannah and James, 2008). The endosperm-specific promoters have been used to drive the expression of genes that are involved in biosynthesis pathways of these storage materials (Roesler et al., 1997; Plant et al., 1994; Kuwano et al., 2009). The insecticidal toxins, such as *Bacillus thuringiensis* (Bt) δ-endotoxins, have been used to control insects (Christou et al., 2006; Roh et al., 2007). Although Bt toxin has high specificity as an insecticidal toxin and safety for the environment, it is still desirable to have Bt toxin specifically expressed in leaf tissues rather than in seeds and fruits (Datta et al., 1998). Therefore, there is an increasing demand of specific promoter to control the expression of gene of interest in specific tissues at particular developmental stages. In addition, the multi-gene transformation system was used for delivery several genes simultaneously constructed in one expression vector (Lin et al., 2003; Chen et al., 2006; Wakasa et al., 2006). Each of these multiple genes needs a different promoter to drive them to avoid the gene silencing. However, a lack of suitable promoters is a critical limiting factor for such research (Qu et al., 2008).

*Jatropha* (*Jatropha curcas*) is a small tropical, woody plant belonging to the Euphorbiaceae family. It is a dicotyledonous plant and its seeds contain as much as 40% oil (Bringi, 1987). The oil from *jatropha* could be an efficient substitute for fossil fuel (Augustus et al., 2002; Azam et al., 2005; Forson et al., 2004; Pramanik, 2003). However, *Jatropha* suffers from several shortcomings that may limit its wide adoption. The productivity of the plant is constrained by the unfavourable male to female flower ratio and its oil content has not been optimized by breeding. This plant is also sensitive to biotic stresses such as viral (Narayanna et al., 2007), fungal and bacterium pathogens and abiotic stresses, especially cold and drought (http colon www dot *jatropha* dot orgy. The presence of several toxic components (e.g. the protein toxin, curcin, and the cancer-causing agent phorbol esters) in seeds and leaves of the plant possess health hazards for farmers and bioprocess workers in the *Jatropha* industry.

Curcin is a toxin protein identified in *jatropha* seeds (Stirpe et al. 1976). The presence of curcin as well as other toxins in *jatropha* seeds prevents the use of *jatropha* seed meals as animal feed (Makkar et al., 1997). Curcin belongs to the type I of ribosome inactivating proteins (RIPS) that has RNA N-glycosidase activity and can irreversibly inactivate ribosomes (Barbieri, 1993, Lin et al., 2003a). Currently, five curcin proteins have been deposited to GenBank and their accession numbers are AAL58089 (Lin et al., 2003a), AAL86778 (Lin et al., 2003b), ABZ04128, AAR08395 and ABW17545. These curcin proteins can be divided into two types based on the length of their amino acid residues. The precursors of type 1 curcin proteins consist of 293-aa residues while the precursors of type 2 curcin proteins contain 309-aa residues. Lin et al. (2003a) identified a type 1 curcin protein from *jatropha* seeds that encodes a 32-kDa curcin precursor with a 42-amino acid signal peptide. Wei et al. (2005) cloned a type 2 curcin gene. The curcin gene, designated as Curcin 2, was found to be induced by stress. Members of curcin proteins within a type display 93% to 98% identity in amino acids while members between two different types show 87%.

An important strategy to improve agronomic and quality traits of *Jatropha curcas* is by genetic modification. Transgenic *Jatropha* plants can be generated expressing homologous or heterologous gene sequences. In many instances, over-expression or silencing by RNA interference (RNAi) of one or more homologous genes of defined function is desired. Gene sequences of *Jatropha* can be obtained from cDNA and genomic libraries and functions of genes can be tentatively assigned by sequence homology with other plant genes of known function. Tissue-specific promoters are often utilized to express homologous or heterologous gene sequences in the desired tissues.

RNAi is a post-transcriptional, targeted gene-silencing technique that uses double-stranded RNA (dsRNA) to incite degradation of messenger RNA (mRNA) containing the same sequence as the dsRNA (Constans, 2002). Small interfering RNAs, or siRNAs are produced in at least two steps: an endogenous ribonuclease cleaves longer dsRNA into shorter, 21-23 nucleotide-long RNAs. The siRNA segments then mediate the degradation of the target mRNA (Zamore, 2001). RNAi has been used for gene function determination in a manner similar to antisense oligonucleotides (Constans, 2002). Expression vectors that continually express siRNAs in transiently and stably transfected have been engineered to express small hairpin RNAs (shRNAs), which get processed in vivo into siRNAs-like molecules capable of carrying out gene-specific silencing (Brummelkamp et al., 2002; Paddison et al., 2002). Post-transcriptional gene silencing by double-stranded RNA is discussed in further detail by Hutvágner and Zamore, 2002; Vaucheret et al., 2001; Hammond et al., 2001; Maine, 2000; Fire et al., 1998; and Timmons and Fire, 1998. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also International Patent Publications WO 97/01952, WO 98/36083, WO 98/53083, WO 99/32619 and WO 01/75164; and U.S. Patent Publications 2003/0175965, 2003/0175783, 2003/0180945, 2004/0214330, 2005/0244858, 2005/0277610, 2007/0265220 and 2010/0058498.

Thus, it is desired to isolate tissue-specific promoters for use in controlling the expression of a gene of interest in specific tissues at particular developmental stages in *Jatropha curcas* other *Jatropha* species as well as other plant species, such as for genetic engineering of such plants. It is also desired to isolated promoters that can be used in genetic engineering of *Jatropha curcas*, other *Jatropha* species as well as other plant species. It is also desired to produce curcin-deficient *jatropha* plants that are non-toxic to humans and animals.

SUMMARY OF THE INVENTION

The present invention relates to the isolation of *Jatropha curcas* curcin genes and tissue-specific promoters and to the production of curcin-deficient *Jatropha* plants. More specifically, the present invention relates to the isolation of *Jatropha curcas* Curcin 1, Curcin 2 and Curcin 2A. The present invention further relates to of the Curcin 1, Curcin 2A and Curcin 2 genes and more particularly to tissue specific promoters of the Curcin 1 and Curcin 2A genes. The present invention further relates to production of curcin-deficient transgenic *jatropha* plants by using RNAi technology to suppress curcin gene expression.

Thus in a first aspect, the present invention provides the sequences of three *Jatropha curcas* curcin genes. In one embodiment, the curin gene is Curcin 1. The nucleotide sequence of Curcin 1 is set forth in SEQ ID NO: 1. The coding sequence for Curcin 1 comprises nuclectotides 474-1355 of SEQ ID NO: 1. The protein sequence for Curcin 1 is set forth in SEQ ID NO: 2.

In a second embodiment, the curin gene is Curcin 2. The nucleotide sequence of Curcin 2 is set forth in SEQ ID NO: 3. The coding sequence for Curcin 1 comprises nuclectotides 439-1368 of SEQ ID NO: 3. The protein sequence for Curcin 2 is set forth in SEQ ID NO: 4.

In a third embodiment, the curin gene is Curcin 2A. The nucleotide sequence of Curcin 2A is set forth in SEQ ID NO: 5. The coding sequence for Curcin 2A comprises nucleotides 475-1404 of SEQ ID NO: 5. The protein sequence for Curcin 2A is set forth in SEQ ID NO: 6.

In a second aspect, the present invention provides the tissue-specific promoters of two *Jatropha curcas* curcin genes and a promoter of a third *Jatropha curcas* curcin gene. In one embodiment, the promoter is derived from the Curcin 1 gene. The nucleotide sequence of Curcin 1 promoter is set forth in SEQ ID NO: 7. The Curcin 1 promoter is an endosperm-specific promoter. Fragments of this sequence are also active as tissue-specific promoters, i.e., as endosperm-specific promoters. Such fragments include the following: (a) nucleotides 1 to 2888 of SEQ ID NO: 7, (b) nucleotides 1142 to 3181 of SEQ ID NO: 7, (c) SEQ ID NO: 7 with nucleotides 2944 to 3170 deleted, (d) nucleotides 1142 to 3181 of SEQ ID NO: 7 with nucleotides 2944 to 3170 deleted and (e) nucleotides 2688 to 3181 of SEQ ID NO: 7 with nucleotides 2944 to 3170 deleted.

In a second embodiment, the promoter is derived from the Curcin 2A gene. The nucleotide sequence of Curcin 2A promoter is set forth in SEQ ID NO: 8. The Curcin 2A promoter is a leaf-specific promoter. Fragments of this sequence are also active as tissue specific promoters. However, the specificity changes from leaf-specific to non-tissue specific when some fragments are deleted. Such fragments that are active as non-tissue specific promoters include the following: (a) nucleotides 912 to 2087 of SEQ ID NO: 8, (b) nucleotides 1 to 2087 of SEQ ID NO: 8 with nucleotides 1853 to 2076 deleted, (c) nucleotides 912 to 2087 of SEQ ID NO: 8 with nucleotides 1853 to 2076 deleted and (d) nucleotides 1751 to 2087 of SEQ ID NO: 8 with nucleotides 1853 to 2076 deleted.

In a third embodiment, the promoter is derived from the Curcin 2 gene. The nucleotide sequence of Curcin 2 promoter is set forth in SEQ ID NO: 9. As described herein, this promoter is not expressed in endosperm or leaf tissues, but may be activated and expressed upon activation by jasmonic acid (JA) upon attack by insects and/or upon activation by ethylene during defense reaction or leaf senescence.

In a third aspect, the present invention provides transgenic *jatropha* plants that are curcin-deficient and to the production of curcin-deficient transgenic *jatropha* plants. In one embodiment, a transgenic plant that is curcin-deficient comprises a nucleic acid stably integrated in its genome, wherein the nucleic acid encodes a double stranded RNA (dsRNA) targeted to a curcin gene. In another embodiment, a transgenic plant that is curcin-deficient comprises a nucleic acid stably integrated in its genome, wherein the nucleic acid encodes short interfering RNA (siRNA) targeted to a curcin gene. In an additional embodiment, a curcin-deficient transgenic plant comprises a nucleic acid stably integrated in its genome, wherein the nucleic acid encodes a short hairpin RNA (shRNA) targeted to a curcin gene. In one embodiment, the curcin gene is Curcin 1. In another embodiment, the curcin gene is Curcin 2. In an additional embodiment, the curcin gene is Curcin 2A. In one embodiment, the nucleic acid includes a portion of the Curcin 1 gene. In another embodiment, the nucleic acid includes a portion of the Curcin 2 gene. In an additional embodiment, the nucleic acid includes a portion of the Curcin 2A gene. In one embodiment, the curcin-deficient transgenic plants are produced by transforming *jatropha* plant tissue. In another embodiment, the transformation is *Agrobacterium*-mediated transformation.

BRIEF DESCRIPTION OF THE FIGURES

FIG. 2 shows the nucleotide sequence of Curcin 1 gene (SEQ ID NO: 1) and its deduced amino acid sequence (SEQ ID NO: 2). The transcription initiation site of Curcin 1 is indicated as position 1 on the nucleotide sequence. The nucleotide sequences of the intron in the 5' untranslated region (5'UTR) are shown in lower-case letters. The positions of oligo primers are highlighted in bold italics with arrows indicating forward or reverse direction. The two Sau3AI sites in the coding region are displayed in bold and underlined. Only the second poly(A) signal sequence is highlighted in bold.

FIG. 3 shows the nucleotide sequence of Curcin 2 gene (SEQ ID NO: 3) and its deduced amino acid sequence (SEQ ID NO: 4). The putative transcription initiation site of Curcin 2 is indicated as position 1 on the nucleotide sequence. The putative nucleotide sequences of the intron in the 5' untranslated region (5'UTR) are shown in lower-case letters. The positions of oligo primers are highlighted in bold italics with arrows indicating forward or reverse direction. The two Sau3AI sites in the coding region are displayed in bold and underlined. Only the second poly(A) signal sequence is highlighted in bold. The annotation of Curcin 2 was predicted based on the annotation of Curcin 1.

FIG. 4 shows the nucleotide sequence of Curcin 2A gene (SEQ ID NO: 5) and its deduced amino acid sequence (SEQ ID NO: 6). The putative transcription initiation site of Curcin 2A is indicated as position 1 on nucleotide sequence. The nucleotide sequences of the intron in the 5' untranslated region (5'UTR) are shown in lower-case letters. The positions of oligo primers are highlighted in bold italics with arrows indicating forward or reverse direction. The Sau3AI site in the coding region is displayed in bold and underlined. Only the second poly(A) signal sequence is highlighted in bold.

FIG. 6 shows an alignment of curcin proteins identified from *J curcas*. Amino acid residues showing identity among eight curcin genes are shown in black background. Dart indicates the cleavage site of N-terminal signal peptide (Lin et al., 2003a). The amino acid sequences identifiers are as follows: Curcin 2A—SEQ ID NO: 6; ABZ04128—SEQ ID NO: 10; AAR08395—SEQ ID NO: 11; ABW17545—SEQ ID NO: 12; Curcin 1—SEQ ID NO: 2; AAL58089—SEQ ID NO: 13; Curcin 2—SEQ ID NO: 4; and AAL86778—SEQ ID NO: 14.

FIG. 8A: Detection of the expression of Curcin 1 and Curcin 2A genes in *jatropha* by RT-PCR. The primers for Curcin 1 were CF and C1SR (Table 1), whereas the promers for Curcin 2A were CF and C2ASR (Table 1). L, RNA sample from leaves; E, RNA sample from endosperm. FIG. 8B: Expression of Curcin 1 in endosperm at different developmental stages. Transcript levels were measured by real-time PCR and the identity of the amplified sequences was confirmed by sequencing. *Jatropha* Actin gene was used as an internal control, and relative values normalized to the 6-week-old seeds (6 wk) are shown. The primers for Curcin 1 were C1SF and C1SR, and the primers for the *jatropha* Actin gene were Jc actin F2 and Jc actin R1 (Table 1). FIG. 8C: Expression of Curcin 2 in leaves. Transcript levels were measured by real-time PCR and the identity of the amplified sequences was confirmed by sequencing. *Jatropha* Actin gene was used as an internal control, and relative values normalized to the young leaves (YL) are shown. The primers for Curcin 2A were C2ASF and C1SR (Table 1), and the primers for the *jatropha* Actin gene were Jc actin F2 and Jc actin R1 (Table 1). YL, young leaves; FL, full-expanded leaves; OL, old leaves; IL, full-expanded leaves infected with mealybuds (*Pseudococcidae hirsutus*).

FIG. 10A: Endosperm cells of a six-week-old seed. Bar=5 µm. FIG. 10B: Preimmune serum control showing no immunolabelling of protein body. Bar=0.2 µm. FIG. 10C: Curcin 1 proteins immunolocalized to protein body. Bar=0.2 µm. FIG. 10D: Oil bodies and cell walls of endosperm cells after immunolabelling with anti-Curcin 1C antibody. Bar=0.5 µm. Arrows indicate plastids with starchy bodies in white colour. Darts indicate curcin proteins immunolabelled with anti-Curcin 1C antibody. cw, cell wall; ob, oil body; pb, protein body.

FIG. 11A: Mesophyll cells after immunolabelling with preimmune serum. Bar=2 µm. FIG. 11B: Preimmune serum control showing no immunolabelling of vacuolar contents (high magnification of area indicated with a frame in FIG. 11A). Bar=0.2 µm. FIG. 11C: Mesophyll cells after immunolabelling with anti-Curcin 1C antibody. Bar=2 µm. FIG. 11D: Curcin 2A proteins immunolocalized to vacuolar contents (high magnification of area indicated with a frame in FIG. 11C). Bar=0.2 µm. Darts indicate curcin proteins immunolabelled with anti-Curcin 1C antibody. C, chloroplast; cw, cell wall; v, vacuole.

FIG. 12A: Leaf cross section after immunolabelling with anti-Curcin 1C antibody. Two adjacent tracheary elements, including an immature tracheary element (I) and a mature tracheary element (M), are surrounded by mesophyll cells. Bar=5 µm. FIG. 12B: Preimmune serum control showing no immunolabelling of secondary cell wall of tracheary element. Bar=0.2 µm. FIG. 12C: Curcin 2A proteins immunolocalized to the secondary cell wall of the immature tracheary element (high magnification of area indicated with a frame at lower left of FIG. 12A). Bar=0.2 µm. FIG. 12D: Curcin 2A proteins immunolocalized to the secondary cell wall of the mature tracheary element (high magnification of area indicated with a frame at upper right of FIG. 12A). Bar=0.2 µm. Arrows indicate pit area on the walls of tracheary elements. Darts indicate curcin proteins immunolabelled with anti-Curcin 1C antibody. mc, mesophyll cell; pcw, primary cell wall; scw, secondary cell wall; v, vacuole.

FIG. 13A: Transient expression of GFP in developing endosperm of *J. curcas* after bombardment with empty vector pC1300 (left panel), $P_{Ubi}$:GFP:$T_{Nos}$ (middle panel) and $P_C1P_3$:GFP:$T_{Nos}$ (right panel) genes. GFP, fluorescence channel; Ph2, phase contrast channel; Merge, merge of the GFP and Ph2 channels. Bar=10 µm. FIG. 13B: Transient expression of GUS activity in the leaf tissues of *J. curcas* after bombardment with empty vector pC1300 (left panel), $P_{35S}$:GUS:$T_{Nos}$ (middle panel) and $P_C2AP3$:GUS:$T_{Nos}$ (right panel) genes. Cells showing GUS activities are in blue color (indicated with darts) after stained with X-Gluc solution.

FIG. 16: Southern blot analysis of the transgenic jatropha plants. Souther blots were probed with Gus linker (upper panel) or Hpt (lower panel) probes. Arrow indicates the position of RNAi cassette when the genomic DNAs of the transgenic plants were digested by restriction enzymes KpnI and SpeI. The primers for the Gus linker were Gus F and Gus R (Table 1). M, molecular maker; Wt, wild-type *jatropha* plants; L3 to L26, independent $T_0$ transgenic *jatropha* plants.

FIG. 17A to 17B shows the expression of double-strand-RNA (dsRNA) from the RNAi cassette and Curcin 2A. FIG. 17A: Expression of dsRNA of curcin 1 in young leaves. Transcript levels of dsRNA of curcin 1 were measured by real-time PCR for the Gus linker and the identity of the amplified sequences was confirmed by sequencing. *Jatropha* Actin gene was used as an internal control, and relative values normalized to transgenic line 17 (L17) are shown. The primers for the Gus linker were Gus RT F1 and Gus RT R1, and the primers for the *jatropha* Actin gene were Jc actin F2 and Jc actin R1 (Table 1). Wt, wild-type plant; L17 to L46, independent $T_0$ plants. FIG. 17B: Expression of Curcin 2A in young leaves. Transcript levels were measured by real-time PCR and the identity of the amplified sequences was confirmed by sequencing. *Jatropha* Actin gene was used as an internal control, and relative values normalized to control transgenic plant transformed with empty vector pC1300 are shown. The primers for Curcin 2A were C2ASF and C2ASR (Table 1), and the primers for the *jatropha* Actin gene were Jc actin F2 and Jc actin R1 (Table 1). Wt, wild-type plant; L17 to L46, independent $T_0$ plants.

FIG. 18 shows the expression of Curcin 2A proteins in young leaves of transgenic *jetropha* plants. FIG. 18: Expression of Curcin 2A in young leaves of transgenic *jatropha* plants. The Curcin 2A proteins (indicated with arrow) were detected with anti-Curcin 1 antibodies. Wt, wild-type plant; L17 to L46 are independent transgenic plants.

FIGS. 19A-19D show the inheritance of transgenes to the $T_1$ generation. FIGS. 19A and 19B: Shoots (A) and roots (B) of wild-type *jatropha* seedlings germinated and grown on half-strength MS medium containing 10 mg/L hygromycin for 12 days. FIGS. 19C and 19D: Shoots (C) and roots (D) of $T_1$ seedlings of transgenic line L26 germinated and grown on half-strength MS medium containing 10 mg/L hygromycin for 12 days.

DETAILED DESCRIPTION OF THE INVENTION

The present invention relates to the isolation of *Jatropha curcas* curcin genes and tissue-specific promoters and to the production of curcin-deficient *Jatropha* plants. More specifically, the present invention relates to the isolation of *Jatropha curcas* Curcin 1; Curcin 2 and Curcin 2A. The present invention further relates to of the Curcin 1, Curcin 2A and Curcin 2 genes and more particularly to tissue specific promoters of the Curcin 1 and Curcin 2A genes. The present invention further relates to production of curcin-deficient transgenic *jatropha* plants by using RNAi technology to suppress curcin gene expression.

Thus in a first aspect, the present invention provides the sequences of three *Jatropha curcas* curcin genes. In one embodiment, the curin gene is Curcin 1. The nucleotide sequence of Curcin 1 is set forth in SEQ ID NO: 1. The coding sequence for Curcin 1 comprises nucletotides 474-1355 of SEQ ID NO: 1. The protein sequence for Curcin 1 is set forth in SEQ ID NO: 2. As shown herein, Curcin 1 is specifically expressed in the endosperm of developing seeds. Curcin 1 localizes to protein bodies of endosperm.

In a second embodiment, the curin gene is Curcin 2. The nucleotide sequence of Curcin 2 is set forth in SEQ ID NO: 3. The coding sequence for Curcin 2 comprises nucletotides 439-1368 of SEQ ID NO: 3. The protein sequence for Curcin 2 is set forth in SEQ ID NO: 4. As shown herein, Curcin 2 is not expressed in developing seeds or leaf.

In a third embodiment, the curin gene is Curcin 2A. The nucleotide sequence of Curcin 2A is set forth in SEQ ID NO: 5. The coding sequence for Curcin 2A comprises nucletotides 475-1404 of SEQ ID NO: 5. The protein sequence for Curcin 2A is set forth in SEQ ID NO: 6. As shown herein, Curcin 2A is specifically expressed in the leaves. Curcin 2A was detected in vacuoles of mesophyll cells and secondary cell wall of leaf tracheary elements.

In a second aspect, the present invention provides the tissue-specific promoters of two *Jatropha curcas* curcin genes. In one embodiment, the promoter is derived from the Curcin 1 gene. The nucleotide sequence of Curcin 1 promoter is set forth in SEQ ID NO: 7. Promoter deletion studies indicate that the Curcin 1 promoter of 2888 base pairs is sufficient for its tissue-specific expression in the seed endosperm. Thus, the Curcin 1 promoter is an endosperm-specific promoter. Fragments of this sequence are also active as tissue specific promoters, i.e., as endosperm-specific promoters. Such fragments include the following: (a) nucleotides 1 to 2888 of SEQ ID NO: 7, (b) nucleotides 1142 to 3181 of SEQ ID NO: 7, (c) SEQ ID NO: 7 with nucleotides 2944 to 3170 deleted, (d) nucleotides 1142 to 3181 of SEQ ID NO: 7 with nucleotides 2944 to 3170 deleted and (e) nucleotides 2688 to 3181 of SEQ ID NO: 7 with nucleotides 2944 to 3170 deleted. The Curcin 1 promoter or its fragments can be used to specifically express downstream DNA of interest in seed endosperm of transgenic plants. In some embodiments, the endosperm-specific Curcin 1 promoter can be used to express DNA of interest, for example a target gene such as a gene encoding an enzyme or a protein, in endosperm of *jatropha* seeds as well as other crop seeds.

In a second embodiment, the promoter is derived from the Curcin 2A gene. The nucleotide sequence of Curcin 2A promoter is set forth in SEQ ID NO: 8. Promoter deletion studies indicate that the Curcin 2A promoter of 1793 base pairs is sufficient for its tissue-specific expression in leaf tissues. Thus, the Curcin 2A promoter is a leaf-specific promoter. Fragments of this sequence are also active as tissue-specific promoters. However, the specificity changes from leaf-specific to non-tissue specific when some fragments are deleted. Such fragments that are active as non-tissue specific promoters include the following: (a) nucleotides 912 to 2087 of SEQ ID NO: 8, (b) nucleotides 1 to 2087 of SEQ ID NO: 8 with nucleotides 1853 to 2076 deleted, (c) nucleotides 912 to 2087 of SEQ ID NO: 8 with nucleotides 1853 to 2076 deleted and (d) nucleotides 1751 to 2087 of SEQ ID NO: 8 with nucleotides 1853 to 2076 deleted.

The Curcin 2A promoter can be used to specifically express downstream DNA of interest in leaf tissues of transgenic plants. In some embodiments, the leaf-specific Curcin 2A promoter can be used to express DNA of interest, for example a target gene such as a gene encoding an enzyme or a protein, in leaves or other green-tissues of Jatropha as well as other crops. In other embodiments, the non-tissue specific fragments of the Curcin 2A promoter can be used to direct the non-tissue specific expression of DNA of interest, such as enzymes or proteins, in *Jatropha*, as well as other crop seeds.

In a third embodiment, the promoter is derived from the Curcin 2 gene. The nucleotide sequence of Curcin 2 promoter is set forth in SEQ ID NO: 9. As described herein, this promoter is not expressed in endosperm or leaf tissues, but may be activated and expressed upon activation by jasmonic acid (JA) upon attack by insects and/or upon activation by ethylene during defense reaction or leaf senescence.

The promoters of the present invention are particularly useful for preparing transgenic plants, including *Jatropha*, to contain a DNA of interest. Other plant species include, but are not limited to, castor bean, palm oil, coconut, peanut, rapeseeds, soybean, sunflower, cassava, tomato, beans, cotton, cucumber, cabbage, barley, oats, wheat, corn and rice. In one embodiment, the Curcin 1 promoter or its fragments can be used to direct expression of the DNA of interest, such as a gene of interest, in the endosperm of seeds of *Jatropha* or other plant seeds. In another embodiment, the Curcin 2A promoter can be used to direct expression of the DNA of interest, such as a gene of interest, in leaves or other green tissue of *Jatropha* or other plant species. In a further embodiment, the Curcin 2 promoter can be used to direct expression of the DNA of interest, such as a gene of interest, under inducible conditions, such as upon activation by JA upon attack by insects and/or upon activation by ethylene during defense reaction or leaf senescence.

The DNA that is inserted (the DNA of interest) into plants of the genera *Jatropha* or other plant species is not critical to the transformation process. Generally the DNA that is introduced into a plant is part of a construct. The DNA may be a gene of interest, e.g., a coding sequence for a protein, or it may be a sequence that is capable of regulating expression of a gene, such as an antisense sequence, a sense suppression sequence, a post-transcriptional gene silencing sequence (an RNAi sequence such as an siRNA, shRNA or dsRNA) or a micro-RNA (miRNA) sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. The promoters and tissue-specific promoters identified herein are particularly useful for preparing constructions for the transformation of *Jatropha*, as well as for the transformation of other plant species. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670, 2006/0248616 and 20090100536, and the references cited therein. The expression cassettes may additionally contain 5' leader sequences in the expression cassette construct. Such leader sequences can act to enhance translation. Translation leaders are known in the art and include those described in International Publication No. WO 2008/094127 and the references cited therein.

In a preferred embodiment, the promoters and tissue-specific promoters identified herein are used in the practice of the invention. The promoters can be selected based on the desired outcome. That is, the nucleic acids can be combined with the tissue-specific promoters for expression in a specific host cell or host tissue of interest.

The DNA of interest that is under control of a promoter, such as a promoter described herein, may be any DNA as defined herein and may be used to alter any characteristic or trait of a plant species into which it is introduced, including *Jatropha* as a preferred embodiment. In one embodiment, the DNA of interest is introduced into a plant in order to enhance a trait of the plant. In another embodiment, an enhanced agronomic trait may be characterized by enhanced plant morphology, physiology, growth and development, yield, nutritional enhancement, disease or pest resistance, or environmental or chemical tolerance. In some aspects, the enhanced trait is selected from group of enhanced traits consisting of enhanced water use efficiency, enhanced temperature tolerance, increased yield, enhanced nitrogen use efficiency, enhanced seed protein enhanced seed oil and enhanced biomass. Increase yield may include increased yield under non-stress conditions and increased yield under environmental stress conditions. Stress conditions may include, for example, drought, shade, fungal disease, viral disease, bacterial disease, insect infestation, nematode infestation, extreme temperature exposure (cold or hot), osmotic stress, reduced nitrogen nutrient availability, reduced phosphorus nutrient availability and high plant density. In some embodiments, the DNA of interest may be used to modify metabolic pathways, such as fatty acid biosynthesis or lipid biosynthesis pathways in seeds, or to modify resistance to pathogens in *Jatropha* or other plant species.

Generally, the expression cassette may additionally comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, International Publication No. WO 02/36782, U.S. Pat. No. 7,205,453 and U.S. Patent Application Publication Nos. 2006/0218670, 2006/0248616, 2007/0143880 and 20090100536, and the references cited therein. This list of selectable marker genes is not meant to be limiting. Any selectable marker gene can be used. The selectable marker gene is also under control of a promoter operable in the plant species to be transformed. Such promoters include those described in International Publication No. WO 2008/094127 and the references cited therein.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

Figure 1:
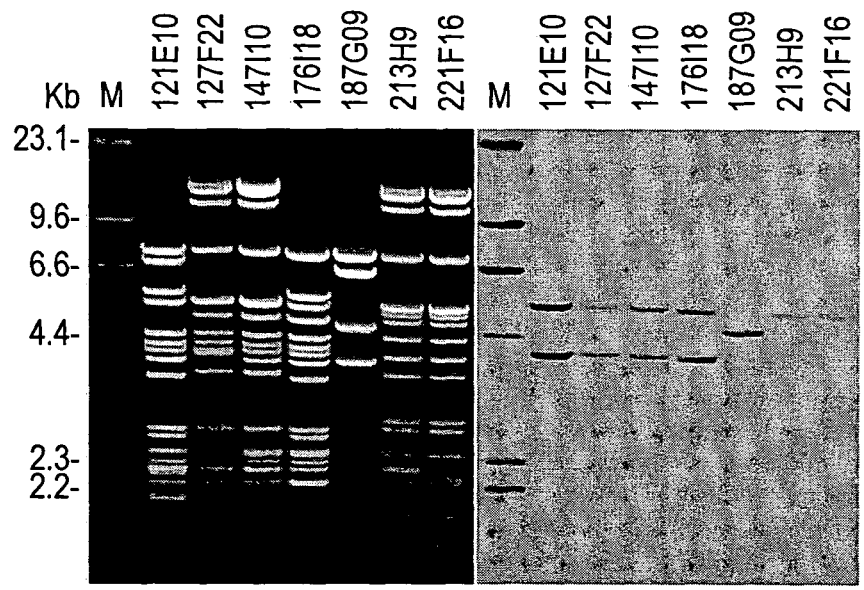
FIG. 1 shows the isolation of BAC clones that contain curcin genes and the isolation of curcin genes. Seven curcin gene-containing BAC clones were digested by HindIII (left panel) and its Southern blot was hybridized with a probe comprising the Curcin 1 coding region (right panel). The molecular weights of standard DNA markers (New England Biolabs, # N3012L) are indicated in kilobases (Kb). M, molecular marker.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Once a nucleic acid has been cloned into an expression vector, it may be introduced into a plant cell using conventional transformation procedures. The term "plant cell" is intended to encompass any cell derived from a plant including undifferentiated tissues such as callus and suspension cultures, as well as plant seeds, pollen or plant embryos. Plant tissues suitable for transformation include leaf tissues, root tissues, meristems, protoplasts, hypocotyls, cotyledons, scutellum, shoot apex, root, immature embryo, pollen, and anther. "Transformation" means the directed modification of the genome of a cell by the external application of recombinant DNA from another cell of different genotype, leading to its uptake and integration into the subject cell's genome. In this manner, genetically modified plants, plant cells, plant tissue, seed, and the like can be obtained.

DNA constructs containing the promoters of the present invention can be used to transform any plant and particularly *Jatropha* plants. The constructs may be introduced into the genome of the desired plant host by a variety of conventional techniques. Techniques for transforming a wide variety of higher plant species are well known and described in the technical and scientific literature. Transformation protocols may vary depending on the type of plant or plant cell, i.e., monocot or dicot, targeted for transformation, as is well known to the skilled artisan. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. Thus, any method, which provides for effective transformation/transfection may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Published Application Nos. WO 2005/103271 and WO 2008/094127 and references cited therein.

In one embodiment, the explant tissue can be co-cultured with an *Agrobacterium* strain harboring a DNA construct containing a gene or nucleic acid of interest using techniques well known in the art. Transformed tissue can be selected using conventional techniques well known in the art. In another embodiment, the embryogenic liquid suspension cultures can be co-cultured with an *Agrobacterium* strain harboring a DNA construct containing a gene or nucleic acid of interest using techniques well known in the art. Transformed tissue can be selected using conventional techniques well known in the art. In a further embodiment, the DNA can be introduced into the explant tissue or cells of the embryogenic liquid suspension culture using conventional techniques, such as particle bombardment. Transformed tissue can be selected using conventional techniques well known in the art. Transformed or transgenic plants can be regenerated using the methods described herein. In a further embodiment, *Jatropha* can be transformed with *Agrobacterium* as described in International Patent Application No. PCT/SG2009/000015 filed on 7 Jan. 2009, incorporated herein by reference.

Transformed plant cells which are derived by any of the above transformation techniques can be cultured to regenerate a whole plant which possesses the transformed genotype and thus the desired phenotype, e.g., a transgenic plant. A "transgenic plant" is a plant into which foreign DNA has been introduced. A "transgenic plant" encompasses all descendants, hybrids, and crosses thereof, whether reproduced sexually or asexually, and which continue to harbor the foreign DNA. Regeneration techniques rely on manipulation of certain phytohormones in a tissue culture growth medium, typically relying on a biocide and/or herbicide marker which has been introduced together with the desired nucleotide sequences. See for example, International Published Application No. WO 2008/094127 and references cited therein.

The foregoing methods for transformation are typically used for producing a transgenic variety in which the expression cassette is stably incorporated. After the expression cassette is stably incorporated in transgenic plants, it can be transferred to other plants by sexual crossing. In one embodiment, the transgenic variety could then be crossed, with another (non-transformed or transformed) variety, in order to produce a new transgenic variety. Alternatively, a genetic trait which has been engineered into a particular cotton line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. Any of a number of standard breeding techniques can be used, depending upon the species to be crossed.

Once transgenic plants of this type are produced, the plants themselves can be cultivated in accordance with conventional procedures. Transgenic seeds can, of course, be recovered from the transgenic plants. These seeds can then be planted in the soil and cultivated using conventional procedures to produce transgenic plants.

In a third aspect, the present invention provides transgenic *jatropha* plants that are curcin-deficient and to the production of curcin-deficient transgenic *jatropha* plants. In one embodiment, a curcin-deficient transgenic plant comprises a nucleic acid stably integrated in its genome, wherein the nucleic acid encodes a double stranded RNA (dsRNA) targeted to a curcin gene. In another embodiment, a curcin-deficient transgenic plant comprises a nucleic acid stably integrated in its genome, wherein the nucleic acid encodes a short interfering RNA (siRNA) targeted to a curcin gene. In an additional embodiment, a curcin-deficient transgenic plant comprises a nucleic acid stably integrated in its genome, wherein the nucleic acid encodes a short hairpin RNA (shRNA) targeted to a curcin gene. In one embodiment, the curcin gene is Curcin 1. In another embodiment, the curcin gene is Curcin 2. In an additional embodiment, the curcin gene is Curcin 2A. In one embodiment, the nucleic acid includes a portion of the Curcin 1 gene. In another embodiment, the nucleic acid includes a portion of the Curcin 2 gene. In an additional embodiment, the nucleic acid includes a portion of the Curcin 2A gene. In one embodiment, the curcin-deficient transgenic plants are produced by transforming jatropha plant tissue. The nucleic acid encoding the dsRNA, siRNA or shRNA is generally included in a construct, such as constructs described herein. The nucleic acid is under the operable control of a promoter. Suitable promoters that can be used include those described herein. The construct may further include other regulatory sequences, such as those described herein.

For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence, or a fragment thereof, of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand, or a fragment thereof, of the coding sequence of the polypeptide of interest, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of the mRNA encoding the polypeptide of interest, and the other strand of the stem portion of the double stranded RNA comprises a sequence that is similar or identical to the sequence that is complementary to the 3' or 5' untranslated region, respectively, or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest, and the other strand of the stem portion comprises a sequence that is similar or identical to the sequence that is complementary to the sequence of the intron or fragment thereof in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

In one embodiment described herein, a construct is prepared which comprises a constitutive promoter, such as the CaMV 35S promoter, a partial sequence of one of the Curcin genes described herein in a sense orientation, a linker, the partial sequence of the same Curcin gene in antisense orientation and terminator, such as the NOS terminator. In one embodiment, the Curcin gene is the Curcin 1 gene and the partial sequence of the Curcin 1 gene comprises 862 nucleotides and is set forth in SEQ ID NO: 53. In another embodiment, the Curcin gene is the Curcin 1 cDNA and the sequence of the Curcin 1 cDNA comprises 1161 nucleotides and is set forth in SEQ ID NO: 54. In an additional embodiment, Curcin gene is the Curcin 2A cDNA and the sequence of the Curcin 2A cDNA comprises 1176 nucleotides and is set forth in SEQ ID NO: 55. In a further embodiment, Curcin gene is the putative Curcin 2 cDNA and the sequence of the putative Curcin 2 cDNA comprises 1140 nucleotides and is set forth in SEQ ID NO: 56. In addition to the sequences set forth in SEQ ID NOs: 53-56, partial sequences of these sequences can also be used. The partial sequences may comprise 50 nucleotides, 100 nucleotides, 150 nucleotides, 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 750 nucleotides, 800 nucleotides, 850 nucleotides or more up to less than the number of nucleotides in the full length sequences. It is understood the partial sequences may comprise any number of nucleotides between the number of nucleotides illustrated, for example, 60 nucleotides, 175 nucleotides, etc. It is also understood that the partial sequences may comprise a range of nucleotides between the number illustrated or any number within those illustrated and the number of nucleotides in the full length sequence, for example, 50-100, 50-800, 100-800, 175-862 of SEQ ID NO: 53, and the like.

An siRNA also can refer to an RNA duplex of nucleotides, or, in some alternative aspects, a single molecule of RNA (which can, in some embodiments, have secondary structure, such as loops so as to form a shRNA) that is targeted to a nucleic acid, e.g., a gene, of interest. A "RNA duplex" refers to the structure formed by the complementary pairing between at least two regions of a RNA molecule. Thus, the "RNA duplex" can comprise one, two, three or more RNA molecules. siRNA is "targeted" to a gene in that the nucleotide sequence of the duplex portion of the siRNA is complementary to a nucleotide sequence of the targeted gene. Thus, by using the sequence of a target gene, any siRNA can be routinely designed and made. In some embodiments, the length of the duplex of siRNAs is less than 30 nucleotides. In some embodiments, the length of the duplex of siRNAs is more than 30 nucleotides. In some embodiments, the duplex can be 40, 39, 38, 37, 36, 35, 34, 33, 32, 31, 30, 29, 28, 27, 26, 25, 24, 23, 22, 21, 20, 19, 18, 17, 16, 15, 14, 13, 12, 11 or 10 or less nucleotides in length. In some embodiments, the length of the duplex is 19-25 nucleotides in length. The RNA duplex portion of the siRNA can be part of a hairpin structure. In one aspect, there is no hairpin structure in an siRNA of the invention. In addition to the duplex portion, the hairpin structure may contain a loop portion positioned between the two sequences that form the duplex. The loop can vary in length. In some embodiments the loop is 2, 3, 4, 5, 6, 7, 8, 9, 10, 11, 12 or 13 or more nucleotides in length. The hairpin structure can also contain 3' or 5' overhang portions. In some embodiments, the overhang is a 3' or a 5' overhang 0, 1, 2, 3, 4 or 5 nucleotides in length. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal. The siRNA can be entirely, or in part, comprised of synthetic nucleotides, natural bases or modified bases. The siRNA molecule targeted to a Curcin gene of interest, such as the Curcin 1 gene, the Curcin 2 gene or the Curcin 2A gene described herein, can be designed using algorithms well known in the art.

For further description of RNAi techniques, see, e.g., U.S. Pat. Nos. 5,034,323; 6,326,527; 6,452,067; 6,573,099; 6,753,139; and 6,777,588. See also International Patent Publications WO 97/01952, WO 98/36083, WO 98/53083, WO 99/32619 and WO 01/75164; and U.S. Patent Publications 2003/0175965, 2003/0175783, 2003/0180945, 2004/0214330, 2005/0244858, 2005/0277610, 2007/0265220, 2009/0215860, 2009/0308041 and 2010/0058498.

In accordance with this aspect of the invention, the curcin-deficient transgenic plants are produced by transforming *jatropha* plant tissue. In one embodiment, the transformation is *Agrobacterium*-mediated transformation. In another embodiment, the transformation is a ballistic method, such as DNA particle bombardment. In an additional embodiment, the transformation is direct delivery, such as electroporation or microinjection. In one embodiment, the *Agrobacterium*-mediated transformation is performed as described herein. In another embodiment, the *Agrobacterium*-mediated transformation is performed as described in International Patent Application No. PCT/SG2009/000015 filed on 7 Jan. 2009, incorporated herein by reference. Plants cells are transformed as described herein. Transformed plant cells are selected as described herein. Transgenic plants are regenerated from the transformed plant cells as described herein. The transgenetic plants are screened for stable incorporation of the RNAi construct and for curcin deficiency as described herein.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, N.Y., 1992); Guthrie and Fink, *Guide to Yeast Genetics and Molecular Biology* (Academic Press, N.Y., 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods

Plant materials and growth condition: *Jatropha curcas* Indonesia accession (JC-MD) was used for experiments except that it was specially mentioned. Plants were grown in experimental field in Singapore at temperatures ranging from 32° C. during the day to 26° C. at night, relative humidity averaged 85%, and the photoperiod was 12 to 13 h.

Constructs:

To construct the expression vectors using GFP as the reporter gene, we amplified the PstI-KpnI fragment including GFP coding sequence from plasmid pSSZ41 (Kolesnik et al., 2004) using primer pairs GFPPstIF and GFPKpnIR (Table 1). PCR products were digested with restriction enzymes PstI and KpnI and then inserted into pCAMBIA1300 vector to generate pCGFP. The Curcin 1 terminator was cloned into the region between KpnI and EcoRI sites of pCGFP to generate pCGFPT1. Promoters of curcin genes were cloned into pCGFPT1 at the region between HindIII and PstI sites to generate final expression constructs. The CaMV35S promoter in pC1305.1 was removed by digesting with HindIII and NcoI and the vector fragment was filled at ends and self-ligated to produce pC1305.1(-35S). Promoters of curcin genes were cloned into pC1305.1(-35S) at the region between KpnI and PstI to drive GUS reporter gene in the constructs. The RNAi construct for the curcin gene was made based on the pANDA vector pANDA35HK (Mild and Shimamoto 2004). Briefly, partial coding sequence of Curcin 1 was amplified using primers Curcin 1 TOPO-F and JCG-R (Table 1). The sequence of the amplified product is set forth in SEQ ID NO: 53. The PCR product was cloned into pENTR D-TOPO (Invitrogen) and finally transferred into pANDA35HK vector to generate pANDA35HKC1 using Gateway® technology (Hartley et al., 2000).

TABLE 1

DNA Oligonucleotide Primers

| Primer Name | Nucleotide Sequence (5' to 3') (SEQ ID NO:) |
|---|---|
| GFPPstIF | AACTGCAGATGGTGAGCAAGGGCGAGGAGCTG (15) |
| GFPKpnIR | GGGGTACCTTACTTGTACAGCTCGTCCATGCCGT (16) |
| CantigenF1 | GCTGGTTCCACTCCAACTTTAAC (17) |
| CantigenF2 | CGGGATCCGGTACTTCCTATTTCTTTAACG (18) |
| CantigenR1 | TCAGACTTTGTATTTGACTGCATTC (19) |
| CantigenR2 | CCCAAGCTTAATTATCTAATGCCTGCACCCC (20) |
| CantigenR3 | CCCAAGCTTCACTAGGATATTGGTATAGTTTTC (21) |
| GSP1 | GTCTGCTGGCTTTGAACTTT (22) |
| GSP1A | CACCCCTAAATCCACATCCT (23) |
| AAP | GGCCACGCGTCGACTAGTACGGGGGGGGGGGGGGG (24) |
| AUAP | GGCCACGCGTCGACTAGTAC (25) |
| C2RTF2 | GGGCATCGGCTAGGGAAATA (26) |

TABLE 1-continued

DNA Oligonucleotide Primers

| Primer Name | Nucleotide Sequence (5' to 3') (SEQ ID NO:) |
|---|---|
| 3'RACEF4 | TCTCATCAAACCAAAACTACAAA (27) |
| C2RTR2 | AGAGGTCTCCCCAGTTGTTC (28) |
| 5'RACEG4 | TGAATCTTGCTGCCTCTG (29) |
| CTRTF2 | GGGCATCGGCTAGGGAAATA (30) |
| 3'RACEF1 | GAGAGGATGTGGATTTAGG (31) |
| C2PF4 | CTTCAAGACACTAGTTCAAAAA (32) |
| C1CDSR | TGATGAGAATGGACAAACTAT (33) |
| C2AFAR3 | CCATAACCAATGTATGATTTGGTA (34) |
| AD2 | NGTCGASWGANAWGAA (35) |
| C2ACDSF | CCCAAGTAAAAGGTCTCA (36) |
| C2TR2EcoRI | CGGAATTCGTATTATTTGGATGGTAGAAAATT (37) |
| CF2 | GATATTTGTGTTTCTTCAT (38) |
| CR2 | TTTGTTGTCCTTTATTTATGCT (39) |
| CF | TTTACTTCCCCGTTTGCTCA (40) |
| C1SR | TATAGCATTAGCAACAATAATAAT (41) |
| C2ASR | CATTAGCAACATGTTTGGACAAC (42) |
| Curcin 1 TOPO-F | CACCCCATTACTTATGACGCTACTAC (43) |
| JCG-R | GTAGGATTAAAGCCATGGCAGC (44) |
| Gus F | GTCAGTGGCAGTGAAGGGCGAAC (45) |
| Gus R | TTCCATACCTGTTCACCGACGAC (46) |
| Gus RT F1 | GTGGCAGTGAAGGGCGAAC (47) |
| Gus RT R1 | AGGTACGGTAGGAGTTGGC (48) |
| C1SF | TGCAGTCAATTACAAAGTCTG (49 |
| C2ASF | AGTAAAAGGTCTCATGGGAGTC (50) |
| Jc actin F2 | TAATGGTCCCTCTGGATGTG (51) |
| Jc actin R1 | AGAAAAGAAAAGAAAAAAGCAGC (52) |

*Jatropha* transformation: Cotyledons from 5-7 days old seedling were excised into 0.5×0.5 cm² discs and co-cultivated with agrobacteria ($OD_{595}$=0.25-0.35) suspended *Agrobacterium* suspension medium (liquid MS salts, B5 vitamins, 1.5 mg/L BA (6-penzylaminopurine), 0.1 mg/L NAA (α-naphthalene-acetic acid), 20 mg/L AS (Acetosyringone), 0.5 g/L MES (2-(N-morpholino)ethanesulfonic acid), 30 g/L sucrose, 10 g/L glucose, pH5.0-5.2) for 2-3 days at 22E C in the dark. The co-cultivated cotyledon discs were then rinsed several times with sterile water, following one wash with 300 mg/L cefotaxime. The cotyledon discs were then cultured on callus formation medium (MS salts, B5 vitamins, 1.5 mg/L 6-BA, 0.05 mg/L NAA, 3.5 mg/L hygromycin, 100 mg/L cefotaxime, 10 mg/L citric acid, 150 mg/L glutamine, 100 mg/L casein hydrolysate, 0.5 g/L $MgCl_2$, 30 g/L sucrose, 2.5 g/L phytagel, pH 5.8-6.0) at 25E C in darkness for 3 weeks. The newly emerged hygromycin-resistant calli were subcultured on shoot regeneration medium I (MS salts, B5 vitamins, 10 mg/L citric acid, 150 mg/L glutamine, 100 mg/L casein hydrolysate, 0.5 g/L $MgCl_2$, 30 g/L sucrose, 1.5 mg/L 6-BA, 0.05 mg/L IBA (indole-3-butyric acid), 2 mg/L adenine, 3.5 mg/L Hygromycin, 100 mg/L cefotaxime, 2.5 g/L phytagel, pH 5.8-6.0) at 25E C in 16 h light/8 h darkness photoperiod for 3 weeks. During this period, any shoots regenerated from calli were required to be subcultured on shoot regeneration medium II (MS salts, B5 vitamins, 10 mg/L citric acid, 150 mg/L glutamine, 100 mg/L casein hydrolysate, 30 g/L sucrose, pH 5.8-6.0, 1.5 mg/L 6-BA, 0.05 mg/L IBA, 0.5 mg/L GA (gibberellic acid), 4 mg/L hygromycin, 100 mg/L cefotaxime, 7 g/L agar). Calli with no regenerated shoots were subcultured on shoot regeneration medium III (MS salts, B5 vitamins, 10 mg/L citric acid, 150 mg/L glutamine, 100 mg/L casein hydrolysate, 0.5 g/L $MgCl_2$, 30 g/L sucrose, 1.5 mg/L 6-BA, 0.05 mg/L IBA, 3.5 mg/L hygromycin, 100 mg/L cefotaxime; 2.5 g/L phytagel, pH 5.8-6.0) for further regeneration of shoots. The regenerated shoots were subcultured on shoot elongation medium (MS salts, B5 vitamins, 10 mg/L citric acid, 150 mg/L glutamine, 100 mg/L casein hydrolysate, 30 g/L sucrose, 0.3 mg/L 6-BA, 0.1 mg/L GA, 7 g/L Agar, pH 5.8-6.0) at 25E C in 16 h light/8 h darkness photoperiod for 3 weeks. The elongated shoots at about 2.5 cm in length were rooted in root induction medium (MS salts, B5 vitamin, 0.07 mg/l IBA, 0.5 g/L MES, 30 g/L sucrose, 2.2 g/L phytagel, PH 5.8). Normally it takes more than one month to get roots.

BAC Library Construction:

BAC library of *J. curcas* was made with BAC vector pIndigoBAC-5 as described by Peterson et al (2000). Briefly, the High Molecular Weight (HMW) DNA was isolated from the fresh leaves according the method OPTION X described in the protocol. The HMW DNA was digested by HindIII and size-selected 100-150-kb fragments were ligated into pIndigoBAC-5. Vector. The product of ligation was transfer into *E. coli* DH10B competent cells and the transformants were arrayed in the 384-well plates. The high density hybridization membrane were prepared and used for BAC clone screening.

Southern and Northern Blot Analysis:

DNA gel blot analysis was carried out according to the standard procedures as previously described (Sambrook et al., 1989). Plant genomic DNA was isolated from leaves as described previously (Dellaporta et al. 1983). About 2 µg DNA was used for each lane in southern analysis. Curcin 1 coding sequence amplified with primer pairs CantigenF 1 and CantigenR1 (Table 1) was used as probes for BAC library screening and Southern blot analyses. Probes were labelled with [$^{32}$P]-dCTP by Rediprime II random prime labelling system (Amersham Biosciences, Piscataway, N.J., USA).

Reverse Transcription Polymerase Chain Reaction (RT-PCR):

Total RNA was isolated from different tissues using RNeasy Plant Mini Kit (Qiagen, Hilden, Germany) according to manufacturer's instruction. The total RNA samples were treated with DNase I. First-strand cDNA was synthesized from 1 µg of total RNA using SMART™ MMLV Reverse Transcriptase (Clontech) according to the manufacturer's instructions.

Rapid Amplification of cDNA Ends (RACE) and Thermal Asymmetric Interlaced (TAIL) PCR:

5' RACE and 3'RACE were carried out according ' to the manufacture's instruction (Invitrogen, Carlsbad, Calif., USA). The primers for 5' RACE of Curcin 1 were primer pairs GSP1 and AAP, and primer pairs GSP1A and AUAP (Table 1). The primers for 3'RACE of Curcin 1 were primer pairs C2RTF2 and AUAP, and primer pairs 3'RACEF4 and AUAP (Table 1). The primers for 5' RACE of Curcin 2A were primer pairs C2RTR2 and AAP, and primer pairs 5'RACEG4 and AUAP (Table 1). The primers for 3'RACE of Curcin 2A were primer pairs CTRTF2 and AUAP, and primer pairs 3'RACEF1 and AUAP (Table 1). TAIL-PCR was performed according to the procedures published previously (Liu et al. 1995). The arbitrary degenerate (AD) primer used for TAIL-PCR was AD2 (Table 1).

Real-time RT-PCR: Quantitative real-time RT-PCR was followed the methods described by Chen et al (2007) and conducted on a Bio-Rad iCycler iQ5 real-time PCR system. Total RNA was extracted from *jatropha* seeds or leaves at developmental stages. The total RNA samples were first treated with DNase I, and then reverse transcribed to first-strand cDNA using iScript cDNA synthesis kit (Bio-Rad) according to the manufacturer's instructions. Oligo primers for real-time RT-PCR were designed based on the 3'UTR of each gene. To ensure maximum specificity and efficiency during quantitative PCR, oligo primers were further tested for linearity of response by constructing standard curves on five or six serial ten-fold dilutions. A standard reaction mixture (15 μl) consisted of 2 μl cDNA template, 1×SsoFast EvaGreen supermix and 500 nM forward and reverse primers. The PCR reaction consisted of an initial denaturizing step of 95E C for 30 sec, followed by 40 cycles of 95E C for 5 sec, 60E C for 10 sec. A melting-curve reaction immediately followed the amplification with heating for 10 sec, starting at 65E C with 0.5E C increments. PCR product specificity was confirmed by melting-curve analysis and electrophoresis on 2% agarose gel to ensure that PCR reactions were free of primer dimmers and non-specific amplicons. The *jatropha* actin gene was used as internal reference to normalize the relative amount of total RNA for all samples. For each selected gene, triplicate sets of PCR reactions, including the actin controls and duplicate negative controls (reaction samples without cDNA templates), were prepared and run in a 96-well plate. The real-time RT-PCR experiments were repeated for each plate to ensure that similar results could be obtained.

Particle Bombardment and Transient Expression of GFP or GUS:

1.0-μm gold particles were coated with plasmid DNA as directed by the manufacturer's instructions (Bio-Rad, Calif., USA). Endosperm from immature *jatropha* seeds at six-week-old developmental stage were manually cut into thin slices of about 0.5-mm thickness. For each bombardment, five to six pieces of slices were bombarded at 1100 psi with a flight distance of 15 cm using a PDS-1000/He system (Bio-Rad). The bombarded samples were cultured overnight at 22-25° C. on wet filter paper in dishes. The bombarded samples were screened with a fluorescence stereomicroscope (Model SZX12, Olympus, Japan) for GFP expression and then imaged on LSM510 META inverted confocal microscope (Zeiss, Jena, Germany) at 488 nm with a band pass of 505-530 nm. The maize ubiquitin promoter and its fusion GFP gene in pSSZ41 (Kolesnik et al., 2004) were used as positive control for GFP assay. For transient GUS expression, leaf discs of 2×2 cm² in size were used for particle bombardment. GUS activity was detected according to the method as described previously (Hiei et al, 1994). X-Gluc staining of GUS activity was observed with a Nikon SMZ1500 stereo microscope and photographed with an attached Nikon DIGITAL SIGHT DS-SMC camera. The CaMV35S promoter with its fusion gene GUS in pC1305.1 was used as the positive control for GUS activity assay. For both GFP and GUS transient expression assays, empty vector pC1300 was used as the negative control.

Generation of Curcin Antibodies:

The N- and C-terminal coding sequences of Curcin 1 were amplified with primer pairs Cantigen F1 and Cantigen R2 for Curcin 1N, and primer, pairs Cantigen F2 and Cantigen R3 for Curcin 1C, respectively (Table 1). The PCR products were cloned into vector pQE30 (Qiagen) to generate pQCF1R2 and pQCF2R3. The constructs were then introduced into *E. coli* BL21 strain for antigen expression. The antigen proteins were extracted and purified by polyhistidine-tagged protein purification kit (MACHEREY-NAGEL, Duren, Germany). The anti-Curcin 1N or anti-Curcin 1C antibodies were raised following standard procedure for polyclonal antibody production for rabbits.

Western Blot Analysis:

Western blot analysis was carried out with 20 μg total proteins from different tissues of plants. Proteins were separated on 12% SDS polyacrylamide gels followed by blotting onto nitrocellulose membrane. Curcin proteins were detected with anti-Curcin 1N or anti-Curcin 1C antibody and a horseradish peroxidase-coupled secondary antibody (Bio-Rad) according to the product manual.

Immunogold Electron Microscopy:

Immunogold electron microscopy was carried out according to the procedure described previously (Chye et al., 1999). Seed or leaf sections were fixed in a solution of 0.5% glutaraldehyde and 2% paraformaldehyde in 0.1 M phosphate buffer for 4 h under vacuum. Specimens were washed with 50 mM phosphate buffer for 45 min. After dehydration in a graded ethanol series, specimens were infiltrated in LR white resin (EMS, Hatfield, Pa. 19440, USA) and embedded in gelatin capsules. Specimens were sectioned at 80 nm using a Leica Ultracut microtome and mounted on Formvar-coated slotted grids. Curcin proteins were detected with anti-curcin polyclonal antibodies followed by labelling with 15 nm gold-conjugated goat anti-rabbit IgG antibody (EMS). Rabbit pre-immune serum was used in control experiments. Samples on grids were further stained with 2% uranyl acetate and 1% lead citrate. Samples were visualized with a transmission electron microscope (JEOL JEM-1230, JEO LTD, Tokyo 196-8558, Japan) operating at 120 kv and photographed with a digital microphotography system (Gatan Inc., Pleasanton, Calif. 94588, USA).

Example 2

Isolation of Curcin 1 and Curcin 2

To isolate curcin genes from *J. curcas*, a *jatropha* BAC library was constructed and seven BAC clones were identified from the BAC library to contain one or two members of curcin genes (FIG. 1). BAC clone 121E10 carried two copies of curcin genes (FIG. 1). BAC 121E10 was sequenced by shotgun approach and the insert in the BAC was revealed to be 64,841 bp. The two curcin genes in the BAC insert were closely linked and arrayed in tandem manner. One curcin gene encodes a 293-aa curcin protein while another encodes a 309-aa curcin 2-like protein. The two curcin genes were thereafter designated as Curcin 1 for the 293-aa curcin and Curcin 2 for the 309-aa curcin, respectively. Curcin 1 and Curcin 2 are 8-kb from each other and Curcin 1 locates at the 3' of Curcin 2. The curcin genes in the remaining six BAC clones were subcloned and sequenced. The curcin genes in BAC clones 127F22, 147110 and 176118 harboured both Curcin 1 and Curcin 2, whereas the curcin genes in 213H9 and 221F16 carried Curcin 1, respectively. BAC clone 187G09 also carried Curcin 1, but its sequence showed mutation at −2463 bp downstream of the Curcin 1 coding sequence.

We performed cDNA library screening and RT-PCR with 5'RACE and 3'RACE to isolate the full-length cDNA clones of the Curcin 1 and Curcin 2 genes. A cDNA corresponding to Curcin 1 was isolated from the endosperm of immature *jatropha* seeds (FIG. 2). Curcin 1 cDNA consists of 1388 nucleotides excluding 3' poly(A) sequence (FIG. 2). It contains a 66-bp 5' untranslated region (5'UTR) and a 213-bp 3'UTR (FIG. 2). Comparing Curcin 1 cDNA with its genomic sequence, a 227-bp intron was identified in 5'UTR (FIG. 2). The intron is located at 12 bp upstream of start codon (FIG. 2). There are two canonical polyadenylation signals (AATAAA) in the 3'-untranslated region of Curcin 1 gene, which is typical for RIPs genes (Lin et al., 2003; Chow et al., 1999). The first polyadenylation signal locates at 80 bp downstream of the stop codon while the second one resides at 20 bp upstream of the polyadenylation site (FIG. 2). Although the genomic sequence of Curcin 2 shows high identity to that Curcin 1, we failed to isolate cDNA for Curcin 2 from either immature seeds or leaf tissues with the above-mentioned technologies. We reasoned that Curcin 2 gene might not express under normal developmental condition. FIG. 3 shows the annotation of Curcin 2 with its genomic sequence, putative intron in the 5'UTR and its deduced amino acid residues.

Example 3

Isolation of Curcin 2A

During our attempt to isolate Curcin 2 cDNA from *jatropha*, we obtained a cDNA clone that showed homology to that of Curcin 2. There are fifty-nine single nucleotide polymorphisms (SNP) in the ORF regions between the cDNA and Curcin 2. The open reading frame (ORF) of the cDNA encodes a curcin protein with 309 amino acid residues which is identical to a type 2 curcin protein in GenBank (Acc. No.: ABZ04128). We designated this curcin gene as Curcin 2A. The genomic clone of Curcin 2A was isolated by PCR. Initially, a 1216-bp genomic region of Curcin 2A was isolated by PCR with primers C2PF4, derived from Curcin 2 genomic clone and C1CDSR from Curcin 2A cDNA (Table 1). This 1216-bp fragment contains 881-bp Curcin 2A promoter. Secondly, a 982-bp fragment corresponding to the 5' regulation region of the Curcin 2A promoter at the upstream of the 881-bp region was isolated by TAIL-PCR with primer pairs C2AFAR3 and AD2 (Table 1). An 832-bp 3' genomic region of Curcin 2A was amplified with C2ACDSF derived from the Curcin 2A cDNA and C2TR2EcoRI based on the Curcin 2 genomic sequence (Table 1). Totally, we have obtained a 3774-bp genomic clone of Curcin 2A including a 1793-bp promoter at the upsteam of transcription initiation site and 758-bp 3' regulation region at the downstream of the stop codon. The gene organization of Curcin 2A is similar to those of Curcin 1. FIG. 4 shows the annotation of Curcin 2A with its genomic sequence, intron in the 5'UTR and its deduced amino acid residues.

Figure 5:
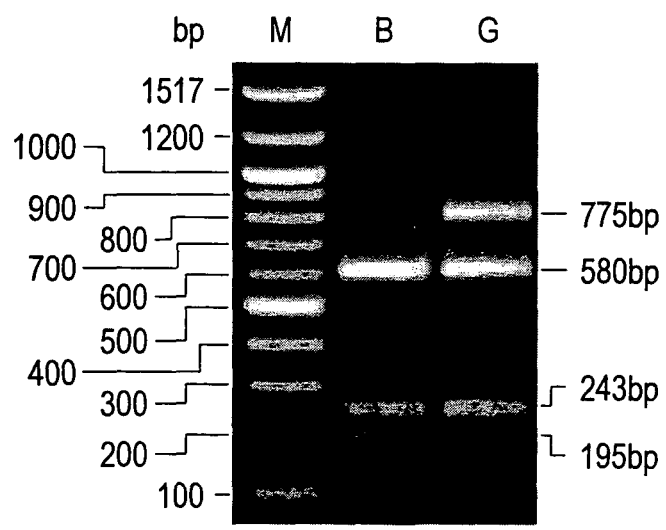
FIG. 5 shows detection of curcin gene polymorphism by cleaved amplified polymorphic sequence (CAPS) analysis. PCR fragments amplified with primers CF2 and CR2 from BAC clone 121E10 (lane B) or genomic DNA (lane G) were digested with Sau3AI. Curcin 1 produced three bands (195 bp, 243 bp and 582 bp), Curcin 2 also produced three bands (195 bp, 243 bp and 580 bp) whereas Curcin 2A produced two bands (243 bp and 775 bp). BAC clone 121E10 only contains Curcin 1 and Curcin 2, therefore, the digested PCR products (lane B) have three bands (195-bp band, 243-bp band, 580-bp and 582-bp bands as they could not be separated in 1.2% agarose gel). Genomic DNA contains all of the three curcin genes. The digested PCR products of genomic DNA (lane G) had all of the bands as shown in lane B and an additional band with size at 775 bp. M, 100-bp DNA ladder is indicated in base pairs (New England Biolabs, # N3231L).

So far, we have isolated three curcin genes from *J. curcas*. Previously, we have obtained seven BAC clones from *jatropha* BAC library. However, DNA sequencing indicated that none of the seven BAC clones harbors Curcin 2A. BAC clones 121E10, 127F22, 147110 and 176118 carry Curcin 1 and Curcin 2, BAC clone 187G09 contains Curcin 1, and BAC clones 213H9 and 221F16 harbor Curcin 2. To further verify the presence of Curcin 2A in the *jatropha* genome, we designated a pair of universal primers CF2 and CR2 (Table 1) to amplify the three curcin genes from genomic DNA as well as Curcin 1 and Curcin 2 from BAC 121E10. The PCR products were digested with Sau3AI and separated on 2% agarose gel. Both Curcin 1 and Curcin 2 generate three fragments (195 bp, 243 bp and 582 bp for Curcin 1; 195 bp, 243 bp and 580 bp for Curcin 2), whereas Curcin 2A produces two fragments (243 bp and 775 bp) due to only one Sau3AI site present in the coding sequence of the gene (FIG. 4). As shown in FIG. 5, the PCR products amplified from BAC 121E10 gave three bands after digestion with Sau3AI (the 582-bp and the 580-bp fragments could not be separated on 1.2% agarose gel), while the products from *jatropha* genome had four bands including an additional 775-bp bands from Curcin 2A. The results indicate the presence of Curcin 1, Curcin 2 and Curcin 2A in *jatropha* genome.

Example 4

Curcin Proteins

Figure 7:
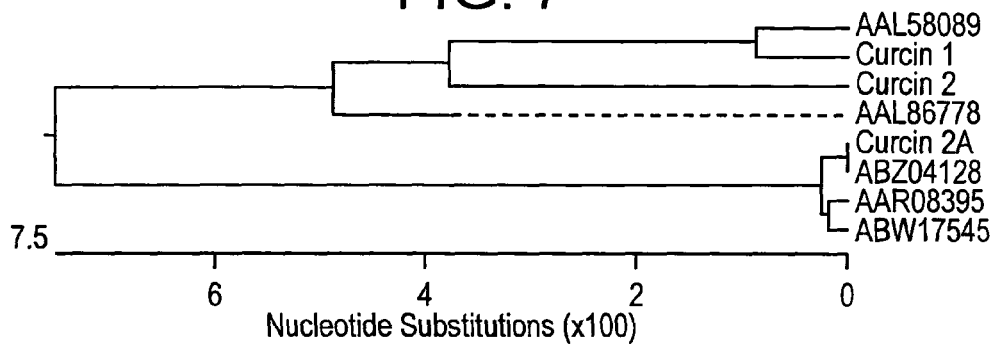
FIG. 7 shows a phylogenetic tree of the curcin proteins identified from *J. curcas*. The phylogenetic tree was created by untitled ClustalW.

The curcin proteins have been identified with Curcin 2A identical to ABZ04128. Total together, there are seven different kinds of curcin proteins (FIG. 6). The first 42 amino acid residues of curcin AAL58089 encodes a signal peptide, which is cleaved in mature protein (Lin et al., 2003a). This N-terminal 42aa signal peptide is conserved among all curcin proteins (FIG. 6). Among these curcin proteins, Curcin 1 identified in this study is more closed to AAL58089 and both belong to type 1 curcins with 293 AA (FIG. 7). Curcin 2A (ABZ04128), AAR083395 and ABW17545 belong to type 2 curcins with 309 AA. These three type 2 curcins are closely related to each other in evolution (FIG. 7). Interestingly, Curcin 2 is more closely related to type 1 curcins, such as Curcin 1 and AAL58089, than type 2 curcins (FIG. 7).

Example 5

Expression of Curcin 1 and Curcin 2A in *Jatropha curcas*

Figure 8A:
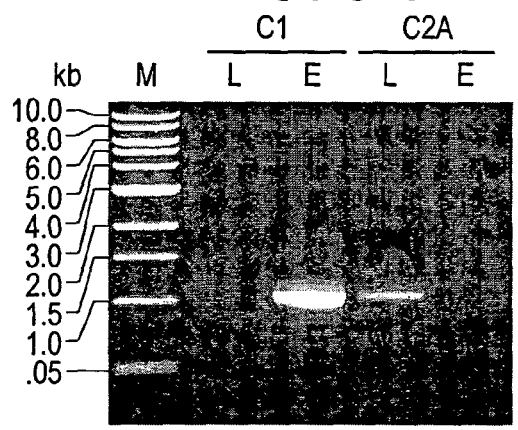
FIGS. 8A-8C show the expression of curcin genes in *J. curcas*.
Figure 8B:
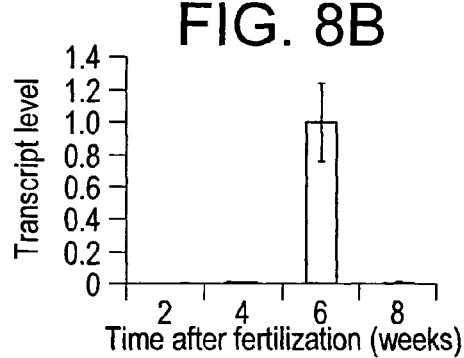
Figure 8C:
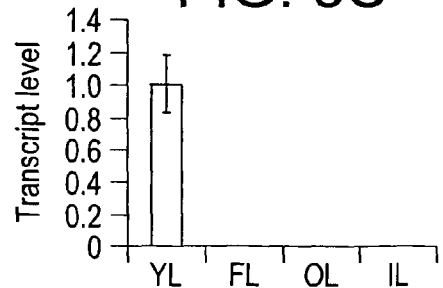

Previous RT-PCR analysis indicated that Curcin 2 did not express in *jatropha* seeds and leaves under normal developmental conditions. We then determined the expression of Curcin 1 or Curcin 2A in the two tissues by RT-PCR with a common forward primer CF and either one of the two specific reverse primers C1SR for Curcin 1 and C2ASR for Curcin 2A (Table 1). Primer CF covers the splicing junction region between exon 1 and exon 2 of Curcin 1 or Curcin 2A. As shown in FIG. 8A, the Curcin 1 transcripts were detected in endosperm. On the contrary, the Curcin 2A transcripts were only present in leaves. We further determined the temporal expression of Curcin 1 in the endosperm of developing seeds (FIG. 8B) as well as in leaves at different developmental stages or infected by insects (FIG. 8C). The Curcin 1 transcripts were detected at high level at 6 weeks after pollination (WAP) (FIG. 8B). No transcript or very low level of Curcin 1 transcript was detected at 2, 4 and 6 WAP (FIG. 8B). Curcin 2A transcripts were only detected in young leaves (YL) but not in full-expanded leaves (FL), old leaves (OL) leaves infected with mealybuds (*Pseudococcidae hirsutus*) (FIG. 8C).

Example 6

Detection of curcin proteins in *Jatropha curcas*

Figure 9:
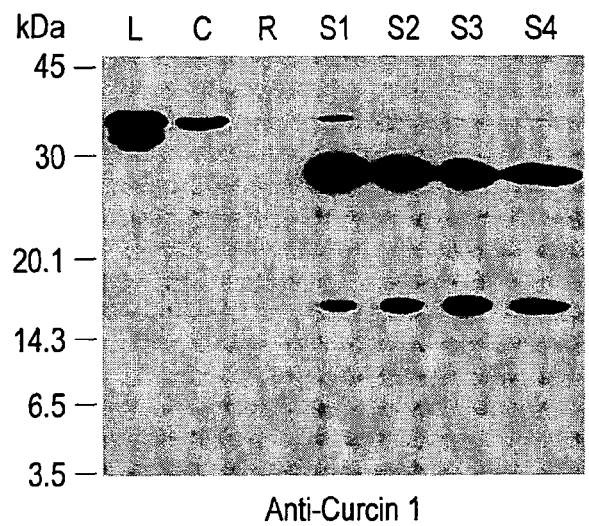
FIG. 9 shows detection of curcin proteins in *J. curcas* showing a Western blot probed with anti-Curcin 1N antibodies. A band with molecular size of about 34 to abot 35 kDa (presumably the Curcin 2A protein) was detected in leaves. Another band with molecular size of about 28 kDa (presumably the mature Curcin 1 protein) was detected in the seeds of all the tested accessions. An unknown protein with molecular size of about 39 kDa was detected in leaves, calli, seeds but not in roots. Similarly, an unknown protein with molecular size of about 16 kDa was detected in seeds. The molecular weights of standard protein markers (Amersham Biosciences, RPN755) are shown in kilodaltons (kDa). L, leaves; C, Calli; R, roots; S1, seeds from Indonesia accession; S2, seeds from India accession; S3, seeds from China accession; S4, seeds from South America accession.

Polyclonal antibodies against C-terminal region of Curcin 1 were raised. Western blot analysis indicated that Curcin 1 proteins were only detected in endospem whereas Curcin 2A proteins were only detected in leaves (FIG. 9). The detected Curcin 1 proteins should be the mature Curcin 1 proteins with the molecular size of about 28 kDa (MW=27.8 kD) (FIG. 9) (Lin et al., 2003a, 2003b). However, the detected Curcin 2A proteins had molecular size of about 34 to 35 kDa and they seemed to be the intact Curcin 2A proteins or precursors of Curcin 2A (MW=34.9 kD) (FIG. 9). It should be mentioned that two unknown proteins were detected by anti-Curcin 1 antibodies. One protein had molecular size of about 39 kDa and was detected in leaves, calli, seeds but not in roots (FIG. 9). Another protein had molecular size of about 16 kDa and was detected in seeds (FIG. 9).

Example 7

Subcellular localization of Curcin 1 and Curcin 2A

Figure 10A:
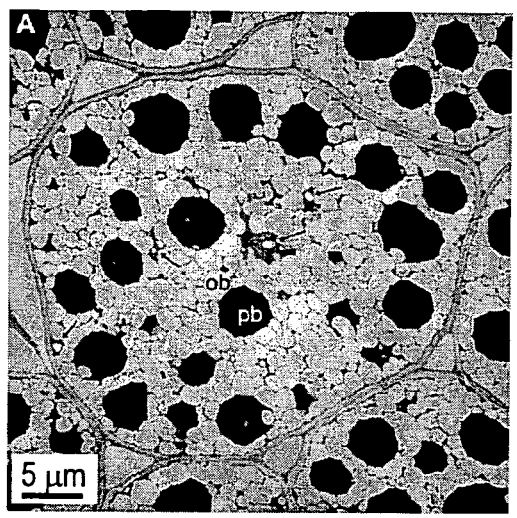
FIGS. 10A-10D show subcellular immunogold localization of Curcin 1 proteins in endosperm cells of developing seeds.
Figure 10B:
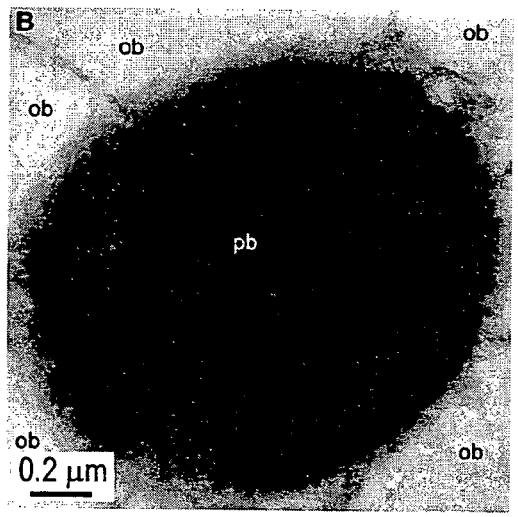
Figure 10C:
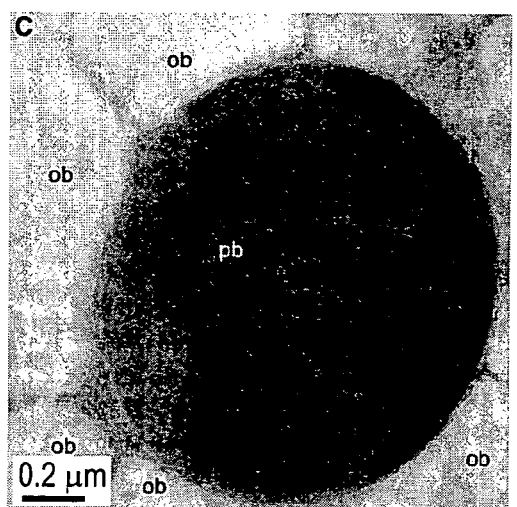
Figure 10D:
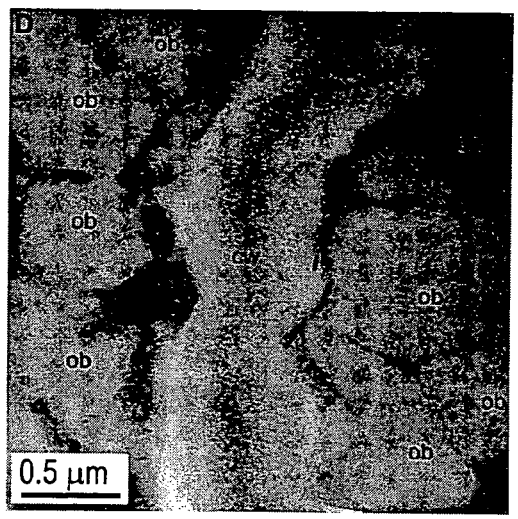

Subcellular localization of curcin proteins was determined by immunogold electron microscopy. As Curcin 1 is only expressed in endosperm at late developmental stage, we took 6-week-old endosperm tissues for subcellular immunogold localization assay of the Curcin 1 proteins. Oil bodies and protein bodies are two major organelles in 6-week-old endosperm cells (FIG. 10A). A few plastids with starch bodies were also observed in endosperm cells at this stage (FIG. 10A). The Curcin 1 proteins, which are indicated by gold particles in immunogold electron microscopy, localized to protein bodies only (FIG. 10C). The cell walls between endosperm cells are primary cell walls, where no Curcin 1 protein was detected or only background labeling was detected (FIG. 10D). No immunolabelling of protein body was detected when preimmune antibody control was used (FIG. 10B). As the anti-Curcin 1 antibody also recognized a 16-kDa non-specific protein in jatropha seeds (FIG. 9), the signal detected by immunogold electron microscopy in this study should include this non-specific recognition.

Figure 11A:
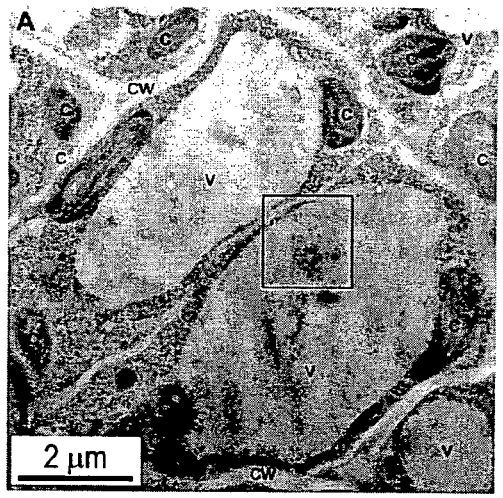
FIGS. 11A-11D show subcellular immunogold localization of Curcin 2A proteins in vacuolar contents of leaf mesophyll cells.
Figure 11B:
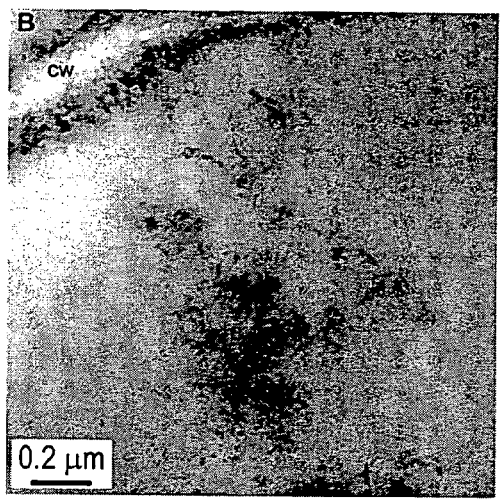
Figure 11C:
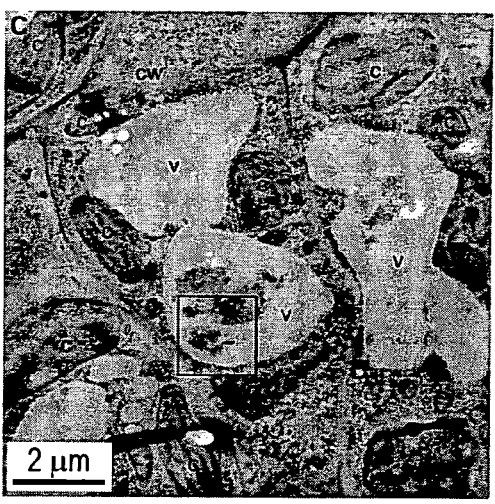
Figure 11D:
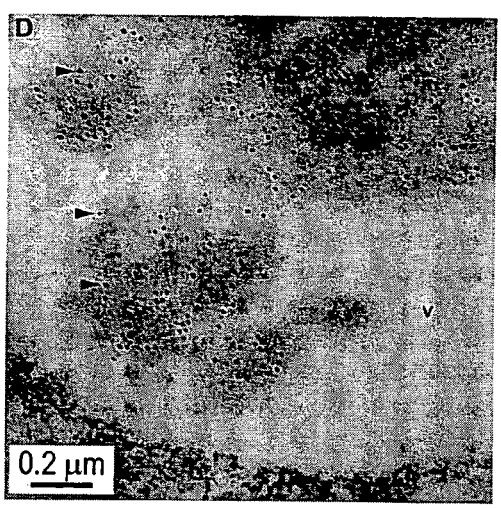
Figure 12A:
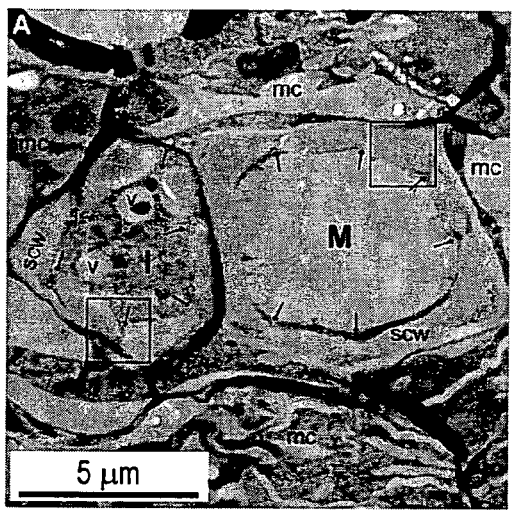
FIGS. 12A-12D show subcellular immunogold localization of Curcin 2A proteins in secondary cell walls of leaf tracheary elements.
Figure 12B:
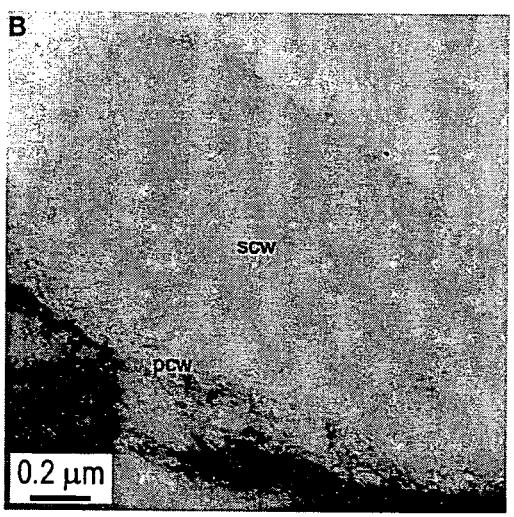
Figure 12C:
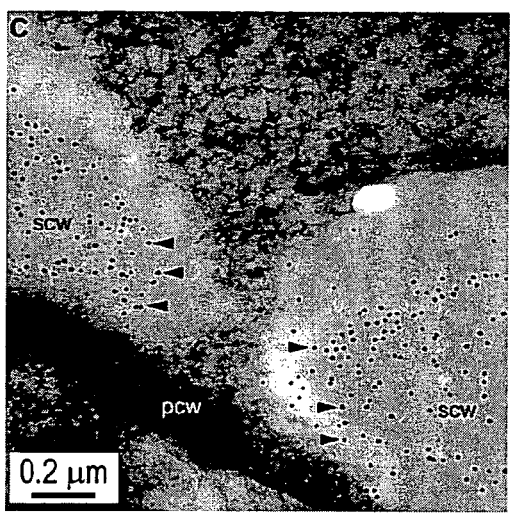
Figure 12D:
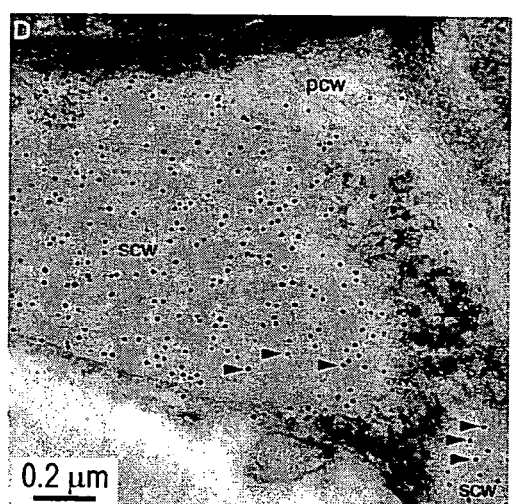

Although the anti-Curcin 1 antibody recognized both Curcin 2A and a 39-kDa non-specific protein from jatropha leaves (FIG. 9), it was used to detect the subcellular localization of the two proteins in jatropha leaves by immunogold electron microscopy assay. Immunogold electron microscopy assay indicated that gold particles were immunolocalized to vacuolar contents of leaf mesophyll cells (FIG. 11D) and secondary cell walls of leaf tracheary elements (FIGS. 12C and 12D). The localization of either the Curcin 2A proteins or the 39-kDa non-specific proteins or both to secondary cell walls of tracheary elements takes place in immature tracheary elements where the cells undergo program cell death (FIGS. 12A and 12C). In control experiments, no immunolabelling or only background signal was detected in vacuolar contents of leaf mesophyll cells (FIGS. 11A and 11B) or secondary cell walls of leaf tracheary elements (FIG. 12B) when preimmune serum was used.

Example 8

Characterization of Curcin 1 and Curcin 2A Promoters

Figure 13A:
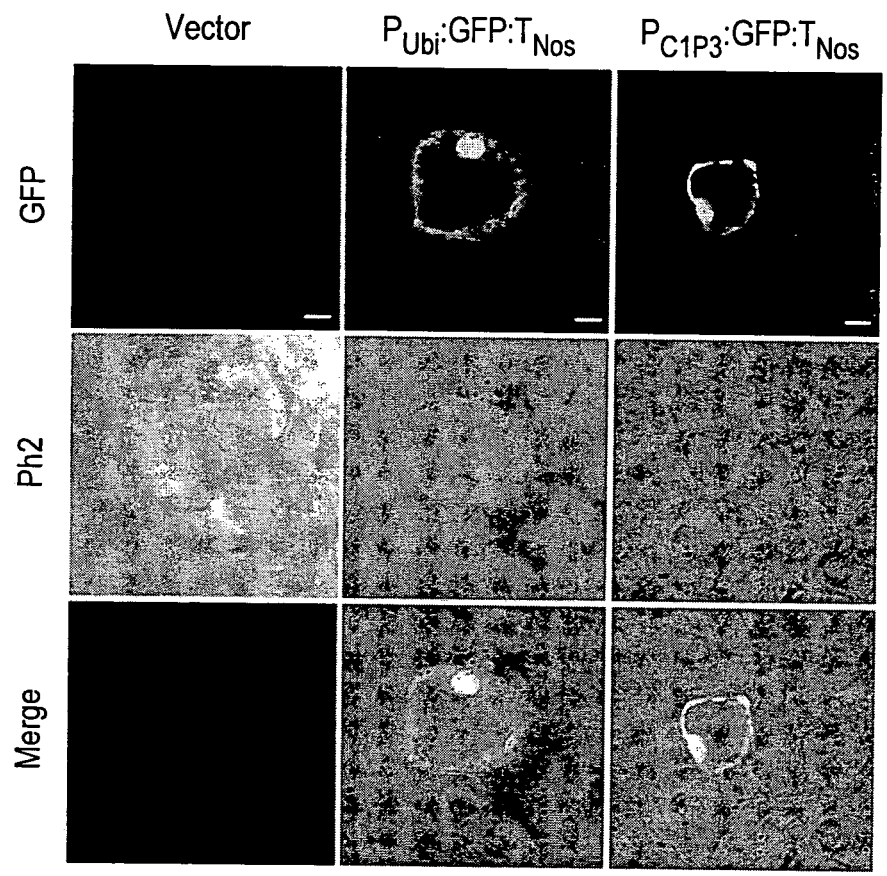
FIGS. 13A and 13B show the characterization of Curcin 1 and Curcin 2A promoters.

Curcin 1 is specifically expressed in endosperm at late developmental stages. We performed PLACE analysis (http colon backslash backslash www dot dna dot affrc dot go dot jp backslash PLACE backslash signalscan dot html) for plant cis-acting regulation DNA elements in Curcin 1 promoter. DNA elements that are involved in endosperm-specific or storage protein gene expression were identified. A DNA element called "RY repeat (CATGCAY)" or legumin box was identified at −1388 bp position (the transcription initiation site is designated at +1 position). The legumin box was found in seed-storage protein genes in legume such as soybean (Glycine max) (Fujiwara and Beachy, 1994). Another DNA element termed AACA element was identified at −1534 bp. The core of AACA element were found in rice (Oryza sativa) glutelin genes and involved in controlling the endosperm-specific expression (Wu et al., 2000). At upstream of the AACA element, there are several E-box elements locate at from −2649 bp and −2273 bp. One of the E-box located at −2649 bp was also found in napA storage-protein gene of rapeseed (Brassica napus) (Stalberg et al., 1996). Curcin 1 promoters containing all these cis-elements (C1P3 and C1P4) were sufficient to drive endosperm-specific gene expression (Table 2, FIG. 13A). Deletion of E-box elements (C1P2) or E-box elements, legumin box and AACA element (C1P1) attenuated or abolished endosperm-specific gene expression (Table 2). No activity of Curcin 1 promoters was detected in leaf tissues (Table 2).

TABLE 2

Characterization of Curcin Gene Promters

| Promoter[a] cells | Size of promoter[b] | Reporter | Tissue tested | Positive sections/ total sections bombarded | Positive or spots/ positive section[c] |
|---|---|---|---|---|---|
| Empty vector - | | — | Endosperm | 0/80 | 0 |
| Empty vector - | | — | Leaf | 0/25 | 0 |
| Ubiquitin | N.A. | GFP | Endosperm | 64/81 | 10-20 cells |
| CaMV35S | N.A. | GUS | Leaf | 5/25[d] | 5-20 spots |
| C1P1 | −200 to +293 | GFP | Endosperm | 0/80 | 0 |
| C1P2 | −1746 to +293 | GFP | Endosperm | 5/80 | 1-3 cells |
| C1P3 | −2888 to +293 | GFP | Endosperm | 42/80 | 5-10 cells |
| C1P4 | −4956 to +293 | GFP | Endosperm | 41/75 | 5-10 cells |
| C1P1 | −200 to +293 | GUS | Leaf | 0/25 | 0 |
| C1P2 | −1746 to +293 | GUS | Leaf | 0/25 | 0 |
| C1P3 | −2888 to +293 | GUS. | Leaf | 0/25 | 0 |
| C1P4 | −4956 to +293 | GUS | Leaf | 0/25 | 0 |
| C1P1D | −200 to +293 (ΔIntron) | GFP | Endosperm | 2/60 | 1-3 cells |
| C1P2D | −1746 to +293 (ΔIntron) | GFP | Endosperm | 38/80 | 5-10 cells |
| C1P3D | −2888 to +293 (ΔIntron) | GFP | Endosperm | 41/83 | 5-10 cells |
| C1P4D | −4956 to +293 (ΔIntron) | GFP | Endosperm | 43/86 | 5-10 cells |
| C1P1D | −200 to +293 (ΔIntron) | GUS | Leaf | 0/25 | 0 |

TABLE 2-continued

Characterization of *Curcin* Gene Promters

| Promoter[a] cells | Size of promoter[b] | Reporter | Tissue tested | Positive sections/ total sections bombarded | Positive or spots/ positive section[c] |
|---|---|---|---|---|---|
| C1P2D | −1746 to +293 (ΔIntron) | GUS | Leaf | 0/25 | 0 |
| C1P3D | −2888 to +293 (ΔIntron) | GUS | Leaf | 0/25 | 0 |
| C1P4D | −4956 to +293 (ΔIntron) | GUS | Leaf | 0/25 | 0 |
| C2AP1 | −42 to +294 | GFP | Endosperm | 0/80 | 0 |
| C2AP2 | −881 to +294 | GFP | Endosperm | 20/80 | 3-5 cells |
| C2AP3 | −1793 to +294 | GFP | Endosperm | 0/80 | 0 |
| C2AP1 | −42 to +294 | GUS | Leaf | 0/25 | 0 |
| C2AP2 | −881 to +294 | GUS | Leaf | 0/25 | 0 |
| C2AP3 | −1793 to +294 | GUS | Leaf | 5/25 | 2-10 spots |
| C2AP1D | −42 to +294 (ΔIntron) | GFP | Endosperm | 3/80 | 1-3 cells |
| C2AP2D | −881 to +294 (ΔIntron) | GFP | Endosperm | 4/75 | 1-3 cells |
| C2AP3D | −1793 to +294 (ΔIntron) | GFP | Endosperm | 1/80 | 4 cells |
| C2AP1D | −42 to +294 (ΔIntron) | GUS | Leaf | 0/25 | 0 |
| C2AP2D | −881 to +294 (ΔIntron) | GUS | Leaf | 0/25 | 0 |
| C2AP3D | −1793 to +294 (ΔIntron) | GUS | Leaf | 0/25 | 0 |
| C2P1 | −326 to +258 | GFP | Endosperm | 0/80 | 0 |
| C2P2 | −1981 to +258 | GFP | Endosperm | 0/80 | 0 |
| C2P3 | −3207 to +258 | GFP | Endosperm | 0/80 | 0 |
| C2P1 | −326 to +258 | GUS | Leaf | 0/25 | 0 |
| C2P2 | −1981 to +258 | GUS | Leaf | 0/25 | 0 |
| C2P3 | −3207 to +258 | GUS | Leaf | 0/25 | 0 |

[a]Empty vector pC1300 was used as negative control. The CaMV35S promoter in pC1305.1 and the ubiquitin promoter in pSSZ41 (Kolesnik et al., 2004) were used as positive controls for endosperm and leaf tissues, respectively.
[b]Transcription initiation site of each promoter is indicated as +1. "ΔIntron" indicates the intron at the 5'UTR of the curcin gene has been deleted.
[c]For transient GFP assay, usually individual cells showing transient GFP expression were observed. For transient GUS expression assay, we only count blue spots. One blue spot is regarded as one successful delivery case.
[d]For each bombardment, one piece of leaf disk at size of 2 × 2 cm² was used. Twenty-five leaf disks were bombarded for GUS transient assay. Even for positive control bombarded with pC1305.1, not all bombarded leaf disks gave blue spot for GUS activity.

Figure 13B:
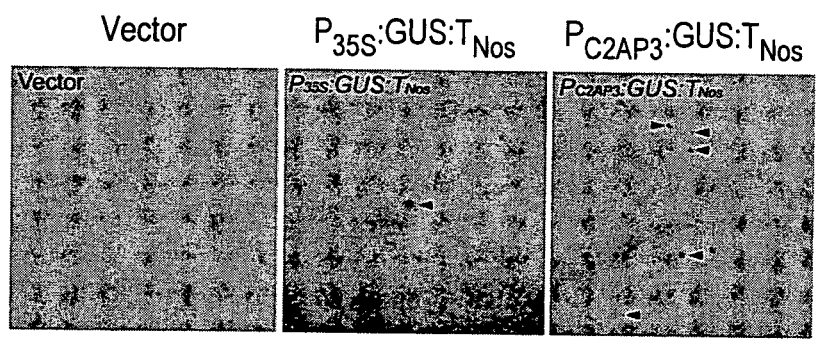

Curcin 2A is specifically expressed in *jatropha* leaves. Totally, a Curcin 2A promoter of 1793 bp was isolated from *J. curcas*. A PLACE survey with the 1793-bp fragment indicated that several light-regulated cis-elements (Terzaghi and Cashmore, 1995) present in the Curcin 1 promoter, which meets its function as a specific promoter with activity in green tissues like leaves. These light-regulated cis-elements include the GT-1 binding sites (Villain et al., 1996) at positions −64, −548, −590, −712, −768, −861, −916, −1315, −1316, −1329, −1411, −1539, −1683 and −1703, I boxes (Giuliano et al., 1988) at positions −548, −861, −916 and −1533, T boxes (Chan et al., 2001) at position −454 and −1581, and GATA boxes (Lam and Chua, 1989) at positions −548, −861, −916, −1093, −1533 and −1747. Although not all these putative cis-element may be functional, the presence of these elements in the Curcin 2A promoter supports its function as leaf- or green-tissue-specific promoter. The PLCAE survey also identified several stress-inducible cis-elements at Curcin 2A promoter. These stress-inducible cis-elements include NPR1-type W boxes (Yu et al., 2001) at positions −54 and −161, ERF3-type W boxes (Nishiuchi et al., 2004) at position at −702, TGAC-containing W-box (Eulgem et al., 1999) at positions −160, −261, −702 and −1453 and MYB binding sites (Urao et al., 1993) at positions −157 and −294. The presence of these putative stress-inducible cis-elements in the Curcin 2A promoter suggests that the Curcin 2A gene might be involved in plant defense. Promoter deletion studies indicated that the light-regulated and stress-inducible cis-elements at the Curcin 2A promoter between position −811 and position −1793 (C2AP3 in Table 2) is required for its leaf-specific activity (Table 2, FIG. 13B). The Curcin 2A promoter carrying cis-elements at upstream to position −811 (C2AP2) still had activity but lost its specificity as a leaf-specific promoter since it only had low level of activity in endosperm but not in leaf tissues (Table 2).

Curcin 2 is not expressed in leaves and endosperm of *J. curcas* under normal developmental condition as no Curcin 2 transcript was detected in these tissues. Transient GFP or GUS assay in endosperm or leaf tissues also did not detect any activity of the Curcin 2 promoter in these tissues (Table 2). DNA alignment with the 3-kb DNA sequences of Curcin 1 and Curcin 2 promoters indicated that the two promoters just show homologous from positions −1 to −275 in Curcin 2 promoter (or positions −1 to −286 in the Curcin 1 promoter). The homologous sequences between Curcin 2 and Curcin 2A promoters start from positions −1 to −1229 in the Curcin 2 promoter (or positions −1 to −1345 in the Curcin 2A promoter). Although PLACE analysis with Curcin 2 promoter identified many cis-elements, two of them which are unique to Curcin 2 promoter are T/G-box (Boter et al., 2004) at position −269 and ethylene responsive element (ERE) at position −782 (Tapia et al., 2005). T/G-boxes, found in tomato proteinase inhibitor II (pin2) and leucine aminopeptidase (LAP) genes, are involved in jasmonate (JA) induction of these genes (Boter et al., 2004), whereas the ERE motifs were found to mediate ethylene-induced activation of the U3 promoter region in the 5'-LTR region of TLC1.1 retrotransposon family in Lycopersicon chilense (Tapia et al., 2005). The presence of T/G-box and ERE motif in the Curcin 2 promoter suggests that the gene might be activated by JA upon attack by insects (Howe and Jander, 2008) and/or ethylene during defense reaction or leaf senescence (van Loon, et al., 2006).

Both Curcin 1 and Curcin 2A have introns in their 5'UTR with lengths of 227 bp and 228 bp, respectively (FIGS. 2 and 4). Curcin 2 might also have the 227-bp intron (FIG. 3). Deletion of the intron in the Curcin 1 promoters with the length up to position −2888 (C1P3D and C1P4D) did not affect their activity and specificity (Table 2). However, deletion of the intron in the Curcin 1 promoters with the lengths up to positions −200 (C1P1D) or −1746 (C1P2D) significantly increased their activity and the mutated promoters still retained specificity for endosperm (Table 2). The results indicate that the intron in the 5'UTR of Curcin1 suppress its expression. Deletion of the intron in 5'UTR of Curcin 2A promoter with length up to positions −42 (C2AP1D) made the promoter have detectable activity in endosperm, whereas the same length of wild-type promoter (C2AP1) did not show any activity even in leaf tissues. Deletion of the intron in 5'UTR of Curcin 2A promoter C2AP2 (C2AP2D) did not significantly change its activity, which was only detected in endosperm (Table 2). Finally, deletion of the intron in 5'UTR of Curcin 2A promoter C2AP3 (C2AP3D) changed its specificity and the activity was detected in endosperm rather than in leaf tissues (Table 3). The deletion studies with the Curcin 2A promoters suggest the intron in the 5'UTR of Curcin 2A affect both its activity and its specificity in leaf tissues.

Example 9

Generation of Curcin-Deficient Transgenic *Jatropha* Plants

Figure 14:
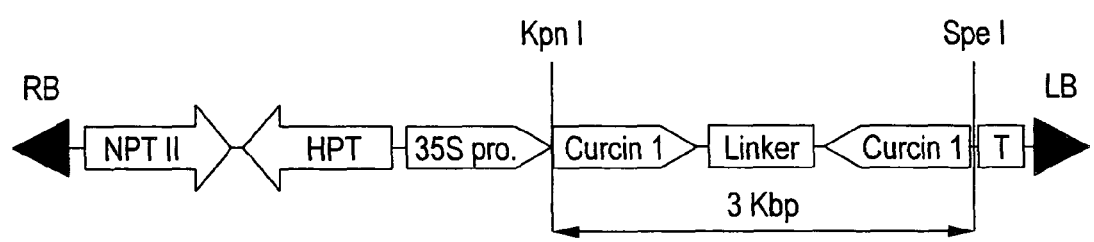
FIG. 14 shows the T-DNA region of the binary plasmid pANDA35HKC1 (not drawn to scale). NPT II, neomycin phosphotransferase gene; HPT, hygromycin phosphotransferase gene; 35S pro., 35S promoter; Curcin 1, partial sequence of Curcin 1; linker, Gus linker; T, terminator of nopaline synthase gene; RB, right border; LB, left border.
Figure 15:
FIG. 15 shows $T_0$ transgenic jatropha plants with knock-down expression of curcin genes. 8-month-old $T_o$ transgenic plants transformed with a binary vector pANDA35HKC1 that carries RNAi cassette designed for the curcin genes are shown.

RNAi strategy was utilized to knock-down curcin gene expression in transgenic *jatropha* plants and produce curcin-deficient *jatropha* plants. Binary construct pANDA35HKC1 contains an RNAi cassette in its T-DNA region (FIG. 14). The expression of the RNAi cassette generates double-strand RNA (dsRNA) of the Curcin 1 gene. pANDA35HKC1 was used for *jatropha* transformation. Initially, ten independent $T_o$ transgenic plants (L3, L4, L11, L17, L19, L22, L23, L24, L26 and L46) were obtained after *Agrobacterium*-mediated transformation. After transplantation, only 4 plants (L17, L23, L26 and L46) were survived in greenhouse (FIG. 15).

Figure 16:
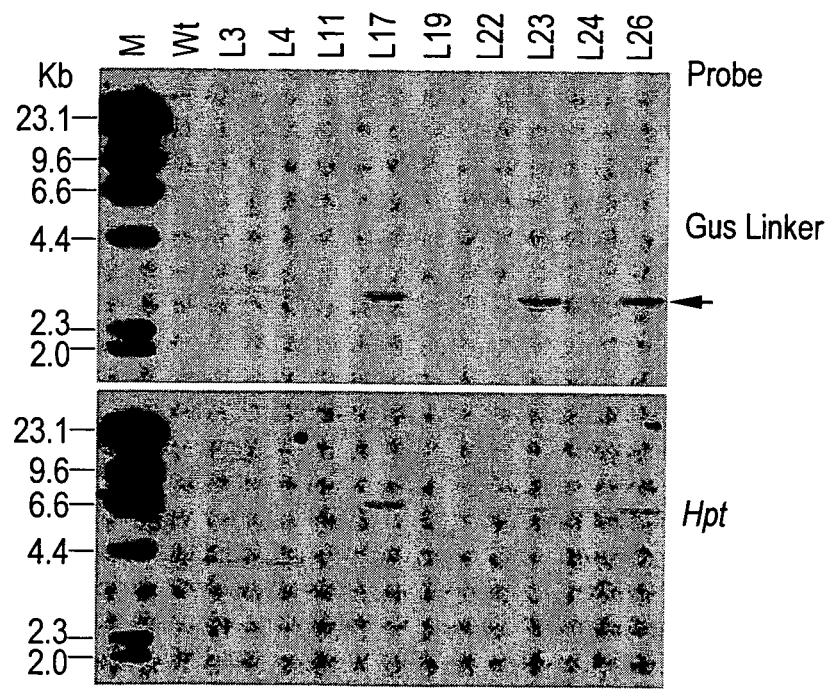
FIG. 16 shows the results of Southern blot analysis of the transgenic jatropha plants.

Southern blot analysis using Gus linker probe indicated that all of the 4 plants carried intact RNAi cassette (FIG. 16, data not shown for L46). Southern blot analysis using Hpt probe showed that they all carried single copy of T-DNA (FIG. 16, data not shown for L46).

Figure 17A:
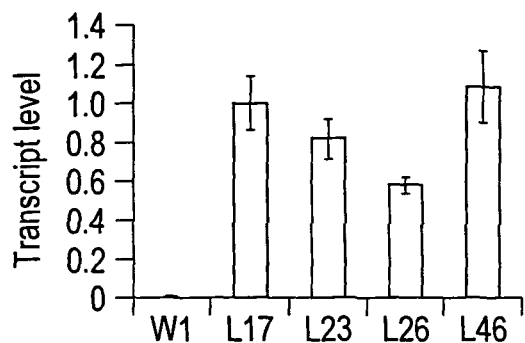
Figure 17B:
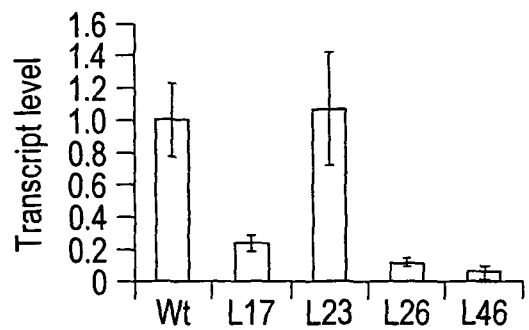

The expression of the RNAi cassette and the Curcin 2A in the young leaves of the transgenic plants was detected by real-time PCR. Real-time PCR analysis with the Gus linker region indicated that the RNAi cassette was expressed in young leaves of the 4 transgenic plants (FIG. 17A). Real-time PCR analysis showed that the Curcin 2A transcripts in young leaves of L17, L26 and L46 were 20% or less than the total Curcin 2A transcripts in the wild-type plants (FIG. 17B). Although the expression of the RNAi cassette in L23 was comparable to that in other transgenic plants, the Curcin 2A transcripts in young leaves of L23 was higher than that in L17, L26 and L46, which was similar to that of wild-type plants.

Figure 18:
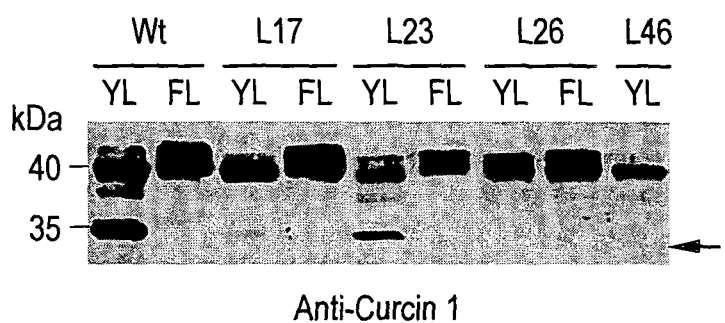
Figure 19A:
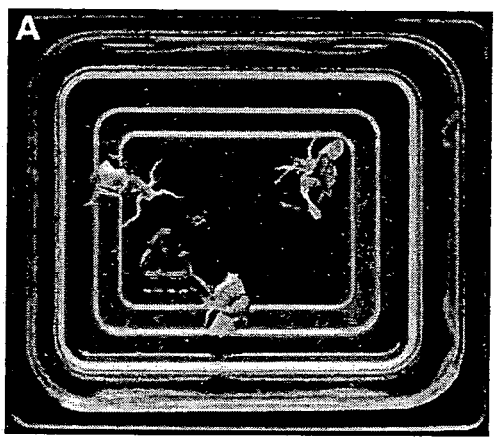
Figure 19B:
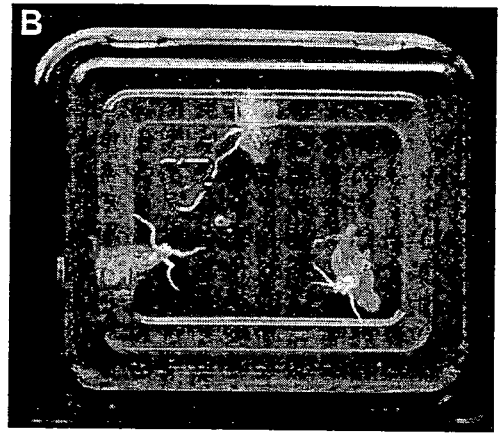
Figure 19C:
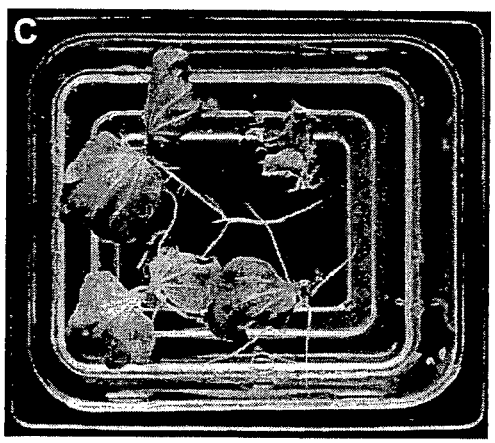
Figure 19D:
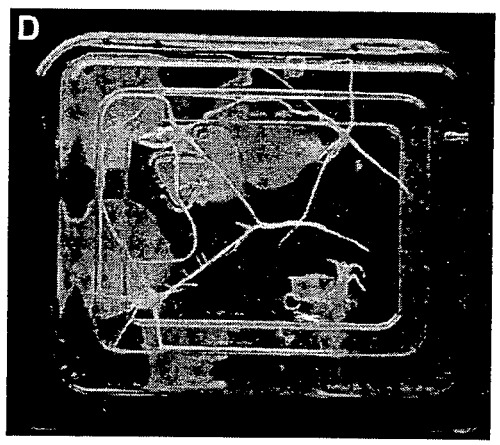

The suppression of Curcin 2A gene in young leaves of the transgenic plants was further confirmed by western blot analysis using anti-Curcin 1 antibodies. In wild-type plants, Curcin 2A was only detected in young leaves but not in full-expanded leaves (FIG. 18). This result was consistent with the fact that Curcin 2A transcripts were only detected in young leaves of wild-type plants (FIG. 8). Curcin 2A was not or hardly detected in transgenic plants L17, L26 and L46 (FIG. 18). Curcin 2A was detected in L23 but its expression level was lower than that of wild-type plants (FIG. 18). The results indicate that the expression of Curcin 2A in the transgenic plants was either partially or completely suppressed by the dsRNA derived from the expression of the RNAi cassette.

To further check the transmission of the T-DNA in the transgenic *jatropha* plants, we germinated $T_1$ seeds of L26 as well as seeds from wild-type plants on selection medium containing 10 mg/L hygromycin. The wild-type seeds were able to germinate on the selection medium, but the young seedlings died within one week (FIG. 19). Fifty $T_1$ seeds of L26 were germinated on the selection medium and thirty-six seedlings were resistant to hygromycin (FIG. 19). L26 carried one copy of T-DNA and the segration of hygromycin-resistant and hygromycin-susceptible follow the Mendelian ratio for single gene inheritance ($X^2$=0.240; 0.5<P<0.8; df=1). This result indicates that the T-DNA region in pANDA35HKC1 has stably integrated into *jatropha* genome and was transmitted to the progeny of the transgenic plants.

In conclusion, we have characterized the promoters of the three curcin genes. The wild-type Curcin 1 promoter with length up to position −2888 is sufficient for its high and specific activity in endosperm, whereas the isolated Curcin 2A promoter with length up to position −1793 has specific activity in leaf tissues. The curcin-deficient transgenic *jatropha* plants were produced by using RNAi technology to suppress curcin gene expression. The curcin-deficient *jatropha* transgenic plants can be used for future breeding program.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Augustus, GDPS, Jayabalan M and Seiler G J. 2002. Evaluation and bioinduction of energy components of *Jatropha curcas*. Biomass and Bioenergy. 23:161-164.

Azam M M, Waris A and Nahar N M. 2005. Prospects and potential of fatty acid methyl esters of some non-traditional seed oils for use as biodiesel in India. Biomass and Bioenergy. 29:293-302.

Barbieri L, Battelli M and Stirpe F. 1993. Ribosome-inactivating protein from plants. Biochim Biophy Acta. 1154: 237-282.

Berger F, Grini P E, Schnittger A. 2006. Endosperm: an integrator of seed growth and development. Curr Opin Plant Biol. 9:664-670.

Boter M, Ruiz-Rivero O, Abdeen A, Prat S. 2004. Conserved MYC transcription factors play a key role in jasmonate signaling both in tomato and *Arabidopsis*. Genes Dev. 18:1577-1591.

Bringi N Y. 1987. Non-traditional oilseeds and oils of India. New Delhi: Oxford & IBH Publishing Co. Pvt. Ltd.

Brummelkamp, T. R. et al. (2002). A system for stable expression of short interfering RNAs in mammalian cells. Science 296:550-553.

Chan C S, Guo L, Shih M C. 2001. Promoter analysis of the nuclear gene encoding the chloroplast glyceraldehyde-3-phosphate dehydrogenase B subunit of *Arabidopsis thaliana* Plant Mol Biol. 46:131-141.

Chen G Q, Turner C, He X, Nguyen T, McKeon T A, Laudencia-Chingcuanco D.

2007. Expression profiles of genes involved in fatty acid and triacylglycerol synthesis in castor bean (*Ricinus communis* L.). Lipids 42: 263-274.

Chen Q, Zhou H, Chen J, Wang X. 2006. A Gateway-based platform for multigene plant transformation. Plant Molecular Biology. 62: 927-936.

Chow L, Chou M, Ho C, Chuang C, Pan F, Wu S, Lin J. 1999. Purification, characterization and molecular cloning of trichoanguin, a novel type I ribosome-inactivating protein from the seeds of Trichosanthes anguina. Biochem J. 338: 211-219.

Christou P, Capell T, Kohli A, Gatehouse J A, Gatehouse A M. 2006. Recent developments and future prospects in insect pest control in transgenic crops. Trends Plant Sci. 11:302-308.

Chye M L, Huang B Q, Zee S Y. 1999. Isolation of a gene encoding *Arabidopsis* membrane-associated acyl-CoA binding protein and immunolocalization of its gene product. Plant J. 18: 205-214.

Constans A. (2002). RNAi for the masses. The Scientist 16:36.

Datta, K., Vasquez, A., Tu, J., Torrizo, L., Alam M. F., Oliva, N., Abrigo, E.,

Khush, G. S., Datta, S. K. 1998. Constitutive and tissue-specific differential expression of the cryIA(b) gene in transgenic rice plants conferring resistance to rice insect pest. Theor Appl Genet. 97:20-30.

Dellaporta S L, Wood J, Hicks J B. 1983. A plant DNA minipreparation: version II. Plant Mol. Biol. Rep. 1:19-21.

Eulgem T, Rushton P J, Schmelzer E, Hahlbrock K and Somssich I E. 1999. Early nuclear events in plant defence signalling: rapid gene activation by WRKY transcription factors. EMBO J. 18:4689-4699.

Fire, A. et al. (1998). Potent and specific genetic interference by double-stranded RNA in *Caenorhabditis elegans*. Nature 391:806-811.

Fujiwara T, Beachy R N. 1994. Tissue-specific and temporal regulation of a beta-conglycinin gene: roles of the RY repeat and other cis-acting elements. Plant Mol Biol. 24:261-272.

Forson F K, Oduro E K and Hammond-Donkoh E. 2004. Performance of *jatropha* oil blends in a diesel engine. Renewable Energy. 29:1135-1145.

Giuliano G, Pichersky E, Malik V S, Timko M P, Scolnik P A, Cashmore A R. 1988.

An evolutionarily conserved protein binding sequence upstream of a plant light-regulated gene. Proc Natl Acad Sci USA. 85:7089-7093.

Hammond, S. M et al. (2001). Post-transcriptional gene silencing by double-strnaded RNA. Nature Rev Gen 2:110-119.

Hannah L C, James M. 2008. The complexities of starch biosynthesis in cereal endosperms. Curr Opin Biotechnol. 19:160-165.

Hartley J L, Temple G F, and Brasch M A. 2000. DNA cloning using in vitro site-specific recombination. Genome Res. 10:1788-1795.

He W J, Liu W Y. 2004. Both N- and C-terminal regions are essential for cinnamomin A-chain to deadenylate ribosomal RNA and supercoiled double-stranded DNA. Biochem J. 377:17-23.

Hiei Y, Ohta S, Komari T, Kumashiro T. 1994. Efficient transformation of rice (*Oryza sativa* L.) mediated by *Agrobacterium* and sequence analysis of the boundaries of the T-DNA. Plant J. 6: 271-282.

Howe G A and Jander G. 2008. Plant immunity to insect herbivores. Annu Rev Plant Biol. 59:41-66.

Hutvágner, G. and Zamore, P. D. (2002). RNAi: nature abhors a double-strand. Curr Opin Genet Dev 12(2): 225-232.

Kolesnik T, Szeverenyi I, Bachmann D, Kumar, C S, Jiang, S, Ramamoorthy, R,

Cai, M, Ma Z G, Sundaresan V, Ramachandran S. 2004. Establishing an efficient Ac/Ds tagging system in rice: large-scale analysis of Ds flanking sequences. Plant J. 37:301-314.

Kuwano M, Mimura T, Takaiwa F, Yoshida K T. 2009. Generation of stable 'low phytic acid' transgenic rice through antisense repression of the 1D-myo-inositol 3-phosphate synthase gene (RINO1) using the 18-kDa oleosin promoter. Plant Biotechnol J. 7:96-105.

Lam E, Chua N H. 1989. ASF-2: A factor that binds to the cauliflower mosaic virus 35S promoter and a conserved GATA motif in cab promoters. Plant Cell. 1:1147-1156.

Lin L, Liu Y, Xu X, Li B. 2003. Efficient linking and transfer of multiple genes by a multigene assembly and transformation vector system. Proceedings of the National Academy of Sciences, USA. 100, 5962-5967.

Lin J, Chen Y, Xu Y, Yang F, Tang L, Chen F. 2003a. Cloning and expression of Curcin, a Ribosome-inactivating Protein from the seeds of *Jatropha curcas*. Acta Botanica Sinica. 45: 858-863.

Lin J, Li Y, Zhou X, Tang K, Chen F. 2003b. Cloning and characterization of a Curcin gene encoding a Ribosome Inactivating Protein from *Jatropha curcas*. DNA sequence. 14: 311-317.

Liu Y G, Whittier R F. 1995. Thermal Asymmetric Interlaced PCR: Automatable Amplification and Sequencing of Insert End Fragments from PI and YAC Clones for Chromosome Walking. Genomics. 25: 674-681.

Maine, E. M. (2000). A conserved mechanism for post-transcriptional gene-silencing? Genome Biol. 1(3):reviews1018.1-reviews1018.4.

Makkar H P S, Becker K, Sporer F and Wink M. 1997. Studies on nutritive potential and toxic constituents of different provenances of *Jatropha curcas*. J Agric Food Chem. 45:3152-3157.

Mansoor S, Amin I, Hussain M, Zafar Y, Briddon R W. 2006. Engineering novel traits in plants through RNA interference. Trends Plant Sci. 11:559-565.

Mild D and Shimamoto K. 2004. Simple RNAi Vectors for Stable and Transient Suppression of Gene Function in Rice. Plant and Cell Physiology. 45:490-495.

Moon Y H, Song S K, Choi K W, Lee J S. 1997. Expression of a cDNA encoding Phytolacca insularis antiviral protein confers virus resistance on transgenic potato plants. Mol Cells. 7:807-815.

Narayana, D S A, Rangaswamy K T, Shankarappa K S, Maruthi M N, Lakshminarayana Reddy C N, Rekha A R, Keshava Murthy K V. 2007. Distinct Begomoviruses Closely Related to Cassava Mosaic Viruses cause Indian *Jatropha* Mosaic Disease. Intl J Virol 3:1-11.

Nishiuchi T, Shinshi H, Suzuki K. 2004. Rapid and transient activation of transcription of the ERF3 gene by wounding in tobacco leaves: Possible involvement of NtWRKYs and autorepression. J Biol Chem. 279: 55355-55361.

Paddison, P. J. et al. (2002). Short hairpin RNAs (shRNAs) induce sequence specific silencing in mammalian cells. Genes & Dev 16:948-958.

Peterson D G, Tomkins J P, Frisch D A, Wing R A, Paterson A H. 2000. Construction of plant bacterial artificial chromosome (BAC) libraries: An illustrated guide. Journal of Agricultural Genomics 5 (www dot ncgr dot org backslash research backslash jag).

Plant A L, van Rooijen G J, Anderson C P, Moloney M M. 1994. Regulation of an *Arabidopsis* oleosin gene promoter in transgenic *Brassica napus*. Plant Mol Biol. 25:193-205.

Pramanik K. 2003. Properties and use of *jatropha curcas* oil and diesel fuel blends in compression ignition engine. Renewable Energy. 28:239-248.

Qu L, Xing Y, Liu W, Xu X and Song Y. 2008. Expression pattern and activity of six glutelin gene promoters in transgenic rice. J Exp. Bot. 59:2417-2424.

Roesler K, Shintani D, Savage L, Boddupalli S and Ohlrogge J. 1997. Targeting of the *Arabidopsis* homomeric acetyl-coenzyme A carboxylase to plastids of rapeseeds. Plant Physiol. 113: 75-81.

Roh J Y, Choi J Y, Li M S, Jin B R, Je Y H. 2007. *Bacillus thuringiensis* as a specific, safe, and effective tool for insect pest control. J Microbiol Biotechnol. 17:547-559.

Sambrook J, Frisch E, Maniatis T. 1989. Molecular Cloning: A Laboratory Manual 2nd edn. Cold Spring Harbor: Cold Spring Harbor Laboratory Press.

Stalberg K, Ellerstom M, Ezcurra I, Ablov S, Rask L. 1996. Disruption of an overlapping E-box/ABRE motif abolished high transcription of the napA storage-protein promoter in transgenic *Brassica napus* seeds. Planta. 199:515-519.

Stirpe F, Pession-Brizzia, Lorenzoni E, Strocchi P, Montanarol L, Sperti S. 1976. Studies on the Proteins from the Seeds of Croton tiglium and of *Jatropha curcas*. Biochem J. 156: 1-6.

Tapia G, Verdugo I, Yanez M, Ahumada I, Theoduloz C, Cordero C, Poblete F, Gonzalez E, Ruiz-Lara S. 2005. Involvement of Ethylene in Stress-Induced Expression of the TLC1.1 Retrotransposon from Lycopersicon chilense Dun. Plant Physiol. 138:2075-2086.

Terzaghi W B, Cashmore A R. 1995. Light-regulated transcription. Annu Rev Plant Physiol Plant Mol Biol. 46:445-474.

Timmons, L. and Fire, A. (1998). Specific interference by ingested dsRNA. Nature 395:854.

Urao T, Yamaguchi-Shinozaki K, Urao S, Shinozaki K. 1993. An *Arabidopsis* myb homolog is induced by dehydration stress and its gene product binds to the conserved MYB recognition sequence. Plant Cell. 5:1529-1539.

van Loon L C, Rep M, Pieterse C M. 2006. Significance of inducible defense-related proteins in infected plants. Annu Rev Phytopathol. 44:135-162.

Vaucheret, H. et al. (2001). Post-transcriptional gene silencing in plants. J Cell Sci 114:3083-3091.

Vickers C E, Xue G, Gresshoff P M. 2006. A novel cis-acting element, ESP, contributes to high-level endosperm-specific expression in an oat globulin promoter. Plant Mol Biol. 62: 195-214.

Villain P, Mache R, Zhou D X. 1996. The mechanism of GT element-mediated cell type-specific transcriptional control. J Biol Chem. 271:32593-32598.

Wakasa Y, Yasuda H, Takaiwa F. 2006. High accumulation of bioactive peptide in transgenic rice seeds by expression of introduced multiple genes. Plant Biotechnology Journal. 4, 499-510.

Wei Q, Huang M, Xu Y, Zhang X, Chen F. 2005. Expression of a ribosome inactivating protein (curcin 2) in *Jatropha curcas* is induced by stress. J. Biosci. 30:351-357.

Wu, C., Washida, H., Onodera, Y., Harada, K., Takaiwa, F. 2000. Quantitative nature of the Prolamin-box, ACGT and AACA motifs in a rice glutelin gene promoter: minimal cis-element requirements for endosperm-specific gene expression. Plant J. 23:415-421.

Yu D, Chen C, Chen Z. 2001. Evidence for an important role of WRKY DNA binding proteins in the regulation of NPR1 gene expression. Plant Cell. 13: 1527-1540.

Zamore, P. D. (2001). RNA interference: listening to the sound of silence. Nature Struct Biol 8:746-750.

What is claimed is:

1. A nucleic acid construct comprising a nucleic acid having promoter activity in a plant operably linked to a heterologous DNA of interest, wherein the nucleic acid having promoter activity in a plant is selected from the group consisting of:
   (a) a nucleic acid comprising nucleotides 1 to 3181 of SEQ ID NO:7;
   (b) a nucleic acid comprising nucleotides 1 to 2888 of SEQ ID NO:7;
   (c) a nucleic acid comprising nucleotides 1142 to 3181 of SEQ ID NO:7;
   (d) a nucleic acid comprising nucleotides 1 to 3181 of SEQ ID NO:7 with nucleotides 2944 to 3170 deleted;
   (e) a nucleic acid comprising nucleotides 1142 to 3181 of SEQ ID NO:7 with nucleotides 2944 to 3170 deleted; and
   (f) a nucleic acid comprising nucleotides 2688 to 3181 of SEQ ID NO:7 with nucleotides 2944 to 3170 deleted.

2. A transgenic plant cell containing within its genome the nucleic acid construct of claim 1.

3. The transgenic plant cell of claim 2, wherein the plant is selected from the group consisting of a *Jatropha* species, castor bean, palm oil, coconut, peanut, rapeseeds, soybean, sunflower, cassava, tomato, beans, cotton, cucumber, cabbage, barley, oats, wheat, corn and rice.

4. The transgenic plant cell of claim 3, wherein the *Jatropha* species is *Jatropha curcas*.

5. A transgenic plant containing within its genome the nucleic acid construct of claim 1.

6. The transgenic plant of claim 5, wherein the plant is selected from the group consisting of a *Jatropha* species, castor bean, palm oil, coconut, peanut, rapeseeds, soybean, sunflower, cassava, tomato, beans, cotton, cucumber, cabbage, barley, oats, wheat, corn and rice.

7. The transgenic plant of claim 6, wherein the *Jatropha* species is *Jatropha curcas*.

8. A method of producing a transgenic plant cell comprising transforming cells of the plant with the nucleic acid construct of claim 1.

9. The method of claim 8, wherein the plant is selected from the group consisting of a *Jatropha* species, castor bean, palm oil, coconut, peanut, rapeseeds, soybean, sunflower, cassava, tomato, beans, cotton, cucumber, cabbage, barley, oats, wheat, corn and rice.

10. The method of claim 9, wherein the *Jatropha* species is *Jatropha curcas*.

11. A method of producing a transgenic plant comprising transforming cells of the plant with the nucleic acid construct of claim 1 and regenerating a transgenic plant from the transformed plant cells.

12. The method of claim 11, wherein the plant is selected from the group consisting of a *Jatropha* species, castor bean, palm oil, coconut, peanut, rapeseeds, soybean, sunflower, cassava, tomato, beans, cotton, cucumber, cabbage, barley, oats, wheat, corn and rice.

13. The method of claim 12, wherein the *Jatropha* species is *Jatropha curcas*.

14. A transgenic *jatropha* plant containing within its genome the nucleic acid construct of claim 1, wherein the transgenic *jatropha* plant is curcin deficient.

15. The transgenic *jatropha* plant of claim 14, wherein the *jatropha* plant is *Jatropha curcas*.

\* \* \* \* \*

SEQUENCE LISTING

```
<160> NUMBER OF SEQ ID NOS: 56

<210> SEQ ID NO 1
<211> LENGTH: 1568
<212> TYPE: DNA
<213> ORGANISM: Jatropha curcas
<220> FEATURE:
<221> NAME/KEY: misc_feature
<222> LOCATION: (181)..(181)
<223> OTHER INFORMATION: transcription start site
<220> FEATURE:
<221> NAME/KEY: 5'UTR
<222> LOCATION: (236)..(462)
<220> FEATURE:
<221> NAME/KEY: CDS
```

<222> LOCATION: (474)..(1355)

<400> SEQUENCE: 1

```
tggattttca ataattcttt ttcattggga tatgttgttg tttgtcttta ttttacatct    60
tatgaaactg tcgtttggtt gctaataata ataataataa taaataaagaa aaaaaattga   120 caaaataaag ggccgggaag gcagtttccc tataaaagca ggtgatgggg gaaggcaaaa   180
gaccatctct tgctctcttc ttctttactt ccccgtttgc tcagttgctt tctttgtaag   240
taatatagaa gcctctgccc ttctttgttg ttgacaaatt ccattttttg ttttactatt   300
agcatgttaa tttctagctt ctggaaatga gttattatc ctttatatga taaacttgtg    360
accattctat ctcttttaa ttattttat aattttatgc aattctatta aaataatcgt    420
attcgtataa tgatatttgt gtttcttcat acaactggac aggtgaaatc aat atg      476
                                                           Met
                                                             1
```

| aaa | ggt | gga | aag | atg | aat | ctc | tcc | att | atg | gtg | gct | gca | tgg | ttt | tgc | 524 |
|-----|-----|-----|-----|-----|-----|-----|-----|-----|-----|-----|-----|-----|-----|-----|-----|-----|
| Lys | Gly | Gly | Lys | Met | Asn | Leu | Ser | Ile | Met | Val | Ala | Ala | Trp | Phe | Cys | |
| | | | 5 | | | | | 10 | | | | | 15 | | | |

| tgg | agt | agt | att | ata | ttc | gga | tgg | gca | tcg | gct | agg | gaa | ata | gtt | tgt | 572 |
|-----|-----|-----|-----|-----|-----|-----|-----|-----|-----|-----|-----|-----|-----|-----|-----|-----|
| Trp | Ser | Ser | Ile | Ile | Phe | Gly | Trp | Ala | Ser | Ala | Arg | Glu | Ile | Val | Cys | |
| | | 20 | | | | | 25 | | | | | 30 | | | | |

| cca | ttc | tca | tca | aac | caa | aac | tac | aaa | gct | ggt | tcc | cct | cca | act | tta | 620 |
|-----|-----|-----|-----|-----|-----|-----|-----|-----|-----|-----|-----|-----|-----|-----|-----|-----|
| Pro | Phe | Ser | Ser | Asn | Gln | Asn | Tyr | Lys | Ala | Gly | Ser | Pro | Pro | Thr | Leu | |
| | 35 | | | | | 40 | | | | | 45 | | | | | |

| acc | att | act | tat | gac | gct | act | act | gat | aag | aaa | aac | tac | gcc | cag | ttc | 668 |
|-----|-----|-----|-----|-----|-----|-----|-----|-----|-----|-----|-----|-----|-----|-----|-----|-----|
| Thr | Ile | Thr | Tyr | Asp | Ala | Thr | Thr | Asp | Lys | Lys | Asn | Tyr | Ala | Gln | Phe | |
| 50 | | | | | 55 | | | | | 60 | | | | | 65 | |

| att | aaa | gat | cta | aga | gaa | gca | ttt | ggc | ttc | agt | tat | tca | agc | cat | gaa | 716 |
|-----|-----|-----|-----|-----|-----|-----|-----|-----|-----|-----|-----|-----|-----|-----|-----|-----|
| Ile | Lys | Asp | Leu | Arg | Glu | Ala | Phe | Gly | Phe | Ser | Tyr | Ser | Ser | His | Glu | |
| | | | | 70 | | | | | 75 | | | | | 80 | | |

| ata | cca | gtc | tta | cgg | gcc | aca | gtt | gct | cca | aat | cag | aaa | ttt | att | gta | 764 |
|-----|-----|-----|-----|-----|-----|-----|-----|-----|-----|-----|-----|-----|-----|-----|-----|-----|
| Ile | Pro | Val | Leu | Arg | Ala | Thr | Val | Ala | Pro | Asn | Gln | Lys | Phe | Ile | Val | |
| | | | 85 | | | | | 90 | | | | | 95 | | | |

| gcc | aaa | gtc | ata | aat | gta | gcg | aat | tta | gaa | gta | tca | tta | gga | tta | aac | 812 |
|-----|-----|-----|-----|-----|-----|-----|-----|-----|-----|-----|-----|-----|-----|-----|-----|-----|
| Ala | Lys | Val | Ile | Asn | Val | Ala | Asn | Leu | Glu | Val | Ser | Leu | Gly | Leu | Asn | |
| | | | 100 | | | | | 105 | | | | | 110 | | | |

| gtc | gtt | aat | gcg | tat | tta | gtg | ggt | tat | aag | gta | gga | ggt | act | tcc | tat | 860 |
|-----|-----|-----|-----|-----|-----|-----|-----|-----|-----|-----|-----|-----|-----|-----|-----|-----|
| Val | Val | Asn | Ala | Tyr | Leu | Val | Gly | Tyr | Lys | Val | Gly | Gly | Thr | Ser | Tyr | |
| | | 115 | | | | | 120 | | | | | 125 | | | | |

| ttc | ttt | aac | gat | ccg | gaa | tct | ttg | gct | gat | gca | aaa | aca | tat | ctt | ttc | 908 |
|-----|-----|-----|-----|-----|-----|-----|-----|-----|-----|-----|-----|-----|-----|-----|-----|-----|
| Phe | Phe | Asn | Asp | Pro | Glu | Ser | Leu | Ala | Asp | Ala | Lys | Thr | Tyr | Leu | Phe | |
| 130 | | | | | 135 | | | | | 140 | | | | | 145 | |

| aca | gac | aca | aag | caa | caa | acg | cta | tca | ttt | act | ggt | agc | tat | gca | gat | 956 |
|-----|-----|-----|-----|-----|-----|-----|-----|-----|-----|-----|-----|-----|-----|-----|-----|-----|
| Thr | Asp | Thr | Lys | Gln | Gln | Thr | Leu | Ser | Phe | Thr | Gly | Ser | Tyr | Ala | Asp | |
| | | | | 150 | | | | | 155 | | | | | 160 | | |

| ttt | cta | tct | agg | gca | aac | gta | cac | aga | gag | gat | gtg | gat | tta | ggg | gtg | 1004 |
|-----|-----|-----|-----|-----|-----|-----|-----|-----|-----|-----|-----|-----|-----|-----|-----|------|
| Phe | Leu | Ser | Arg | Ala | Asn | Val | His | Arg | Glu | Asp | Val | Asp | Leu | Gly | Val | |
| | | | 165 | | | | | 170 | | | | | 175 | | | |

| cag | gca | tta | gat | aat | tac | ata | tat | aca | ctt | gaa | aaa | agt | tca | aag | cca | 1052 |
|-----|-----|-----|-----|-----|-----|-----|-----|-----|-----|-----|-----|-----|-----|-----|-----|------|
| Gln | Ala | Leu | Asp | Asn | Tyr | Ile | Tyr | Thr | Leu | Glu | Lys | Ser | Ser | Lys | Pro | |
| | | | | 180 | | | | | 185 | | | | | 190 | | |

| gca | gac | att | gct | aaa | cct | cta | gtt | ggt | ttt | atc | gaa | atg | gtt | cca | gag | 1100 |
|-----|-----|-----|-----|-----|-----|-----|-----|-----|-----|-----|-----|-----|-----|-----|-----|------|
| Ala | Asp | Ile | Ala | Lys | Pro | Leu | Val | Gly | Phe | Ile | Glu | Met | Val | Pro | Glu | |
| | | | 195 | | | | | 200 | | | | | 205 | | | |

| gca | gca | aga | ttc | aaa | tat | att | gag | aaa | aaa | gta | tta | agt | caa | att | agc | 1148 |
|-----|-----|-----|-----|-----|-----|-----|-----|-----|-----|-----|-----|-----|-----|-----|-----|------|
| Ala | Ala | Arg | Phe | Lys | Tyr | Ile | Glu | Lys | Lys | Val | Leu | Ser | Gln | Ile | Ser | |
| 210 | | | | | 215 | | | | | 220 | | | | | 225 | |

| aaa | acc | ttt | agg | ccg | ggt | ggt | gac | ata | att | agc | ctt | gag | aac | aac | tgg | 1196 |
|-----|-----|-----|-----|-----|-----|-----|-----|-----|-----|-----|-----|-----|-----|-----|-----|------|

```
Lys Thr Phe Arg Pro Gly Gly Asp Ile Ile Ser Leu Glu Asn Asn Trp
                230                 235                 240 gga gac ctc tct tat caa ata cag aaa tgt gta aat ggt gta ttt ctg      1244
Gly Asp Leu Ser Tyr Gln Ile Gln Lys Cys Val Asn Gly Val Phe Leu
            245                 250                 255 aag cca gtt caa tta caa cgt gaa aac tat acc aat atc cta gtg aac      1292
Lys Pro Val Gln Leu Gln Arg Glu Asn Tyr Thr Asn Ile Leu Val Asn
        260                 265                 270 aat gtc acc caa gta gca ggt gtc atg gga gtc ttg ttg aat gca gtc      1340
Asn Val Thr Gln Val Ala Gly Val Met Gly Val Leu Leu Asn Ala Val
    275                 280                 285 aat tac aaa gtc tga atggaagaaa ttattttcaa ctaccaaaag tggctgccat      1395
Asn Tyr Lys Val
290 ggctttaatc ctactttgc tctatatata gagtagcata aataaaggac aacaaattta    1455 ttattattgt tgctaatgct atatgctatt tccctgtaat atcctcatct ttccaatgta   1515 tgaatatgat gatgaattat atatgacaaa taaagtttct actagttctt aat          1568

<210> SEQ ID NO 2
<211> LENGTH: 293
<212> TYPE: PRT
<213> ORGANISM: Jatropha curcas

<400> SEQUENCE: 2

Met Lys Gly Gly Lys Met Asn Leu Ser Ile Met Val Ala Ala Trp Phe
1               5                   10                  15

Cys Trp Ser Ser Ile Ile Phe Gly Trp Ala Ser Ala Arg Glu Ile Val
            20                  25                  30

Cys Pro Phe Ser Ser Asn Gln Asn Tyr Lys Ala Gly Ser Pro Pro Thr
        35                  40                  45

Leu Thr Ile Thr Tyr Asp Ala Thr Thr Asp Lys Lys Asn Tyr Ala Gln
    50                  55                  60

Phe Ile Lys Asp Leu Arg Glu Ala Phe Gly Phe Ser Tyr Ser Ser His
65                  70                  75                  80

Glu Ile Pro Val Leu Arg Ala Thr Val Ala Pro Asn Gln Lys Phe Ile
                85                  90                  95

Val Ala Lys Val Ile Asn Val Ala Asn Leu Glu Val Ser Leu Gly Leu
            100                 105                 110

Asn Val Val Asn Ala Tyr Leu Val Gly Tyr Lys Val Gly Gly Thr Ser
        115                 120                 125

Tyr Phe Phe Asn Asp Pro Glu Ser Leu Ala Asp Ala Lys Thr Tyr Leu
    130                 135                 140

Phe Thr Asp Thr Lys Gln Gln Thr Leu Ser Phe Thr Gly Ser Tyr Ala
145                 150                 155                 160

Asp Phe Leu Ser Arg Ala Asn Val His Arg Glu Asp Val Asp Leu Gly
                165                 170                 175

Val Gln Ala Leu Asp Asn Tyr Ile Tyr Thr Leu Glu Lys Ser Ser Lys
            180                 185                 190

Pro Ala Asp Ile Ala Lys Pro Leu Val Gly Phe Ile Glu Met Val Pro
        195                 200                 205

Glu Ala Ala Arg Phe Lys Tyr Ile Glu Lys Val Leu Ser Gln Ile
    210                 215                 220

Ser Lys Thr Phe Arg Pro Gly Gly Asp Ile Ile Ser Leu Glu Asn Asn
225                 230                 235                 240

Trp Gly Asp Leu Ser Tyr Gln Ile Gln Lys Cys Val Asn Gly Val Phe
```

-continued

```
                        245                 250                 255
Leu Lys Pro Val Gln Leu Gln Arg Glu Asn Tyr Thr Asn Ile Leu Val
            260                 265                 270

Asn Asn Val Thr Gln Val Ala Gly Val Met Gly Val Leu Leu Asn Ala
        275                 280                 285

Val Asn Tyr Lys Val
    290

<210> SEQ ID NO 3
<211> LENGTH: 1547
<212> TYPE: DNA
<213> ORGANISM: Jatropha curcas
<220> FEATURE:
<221> NAME/KEY: misc_feature
<222> LOCATION: (181)..(181)
<223> OTHER INFORMATION: transcription start site
<220> FEATURE:
<221> NAME/KEY: 5'UTR
<222> LOCATION: (201)..(427)
<220> FEATURE:
<221> NAME/KEY: CDS
<222> LOCATION: (439)..(1368)

<400> SEQUENCE: 3
ccttgcattt tcaataattc tttttcattg ggatttgttg ttgtttgtct ttattttaca      60
tcttatgaaa ctgtcgtttg gtagctaata ataataataa taataataat aataaagaaa    120
aaaaattgac aaaataaagg gcagtttccc tataaaagca ggtgatgggg gaaggcaaaa    180
gaccatctct cgctttcttt gtaagtaata gtgaagcctc tgcccttctt ttttgttgac    240
aaattccatt ttttgtttta ctaatagcat gttaatttct agcttctgga aatgagttta    300 ttatcccttta tatgataaac ttgtgaacat tctatctctt tttaattatt tttataattt    360
tatgcaaagc tattaaaata atcgtattcg tataatgata tttgtgtttc ttcatacaac    420
tggacaggtg aaatcaat atg aaa ggt ggc aag atg aac ctc tct att atg      471
                    Met Lys Gly Gly Lys Met Asn Leu Ser Ile Met
                    1               5                   10 gtg gct gca tgg ttt tgc tgg agt tgt att ata ttc gga tgg gca tcg      519
Val Ala Ala Trp Phe Cys Trp Ser Cys Ile Ile Phe Gly Trp Ala Ser
            15                  20                  25 gct agg gaa ata gtt tgt cca ttc tca tca aac caa aac tac aaa gct      567
Ala Arg Glu Ile Val Cys Pro Phe Ser Ser Asn Gln Asn Tyr Lys Ala
        30                  35                  40 ggt tcc act cca act tta acc att act tat gac gct gct gct gat aag      615
Gly Ser Thr Pro Thr Leu Thr Ile Thr Tyr Asp Ala Ala Ala Asp Lys
    45                  50                  55 aaa aac tac gcc aac ttc att aga gat cta aga gaa gca ttt ggc ttc      663
Lys Asn Tyr Ala Asn Phe Ile Arg Asp Leu Arg Glu Ala Phe Gly Phe
60                  65                  70                  75 agt tat tca agc cat gaa ata cca gtc cta cgg gcc acg gtt gct gca      711
Ser Tyr Ser Ser His Glu Ile Pro Val Leu Arg Ala Thr Val Ala Ala
                80                  85                  90 aat cag aaa ttt att gta gcc aaa gtc ata aat gta gcg aat tta gaa      759
Asn Gln Lys Phe Ile Val Ala Lys Val Ile Asn Val Ala Asn Leu Glu
            95                  100                 105 gta tca tta gga tta aac gtc gtt aat gca tat tta gtg gct tat aag      807
Val Ser Leu Gly Leu Asn Val Val Asn Ala Tyr Leu Val Ala Tyr Lys
        110                 115                 120 gca gga ggt aca tcc tat ttc ttt aac gat ccc gaa tct ttg gct gat      855
Ala Gly Gly Thr Ser Tyr Phe Phe Asn Asp Pro Glu Ser Leu Ala Asp
    125                 130                 135
```

```
gca aaa aaa tat ctt ttc aca gac aca aag caa caa acg cta tca ttt      903
Ala Lys Lys Tyr Leu Phe Thr Asp Thr Lys Gln Gln Thr Leu Ser Phe
140             145                 150                 155 act ggt agc tat gca gat ttt cta tct agg gca aac gta cac aga gag      951
Thr Gly Ser Tyr Ala Asp Phe Leu Ser Arg Ala Asn Val His Arg Glu
            160                 165                 170 gat gtg gat tta ggg gtg ctg gca tta gat aat tac ata tat ata ctt      999
Asp Val Asp Leu Gly Val Leu Ala Leu Asp Asn Tyr Ile Tyr Ile Leu
    175                 180                 185 cac aaa agt tct caa cca gca gac att gct aaa cct cta gtt ggt ttt     1047
His Lys Ser Ser Gln Pro Ala Asp Ile Ala Lys Pro Leu Val Gly Phe
190                 195                 200 atc gaa atg gtt cca gag gca gca aga ttc aaa tat att gag aaa aaa     1095
Ile Glu Met Val Pro Glu Ala Ala Arg Phe Lys Tyr Ile Glu Lys Lys
    205                 210                 215 gta tta act caa att agc gaa acc ttt agg ccg cgt ggt gtc ata att     1143
Val Leu Thr Gln Ile Ser Glu Thr Phe Arg Pro Arg Gly Val Ile Ile
220                 225                 230                 235 agc ctt gag aac aac tgg gga gac ctc tct tat caa ata cag aaa tct     1191
Ser Leu Glu Asn Asn Trp Gly Asp Leu Ser Tyr Gln Ile Gln Lys Ser
            240                 245                 250 gta aat ggt ata ttt ctg aag cca gtt caa ttg caa cgt gaa aac tat     1239
Val Asn Gly Ile Phe Leu Lys Pro Val Gln Leu Gln Arg Glu Asn Tyr
        255                 260                 265 acc aat atc cta gtg aac aat gtc acc caa gta aca ggt ctc atg gga     1287
Thr Asn Ile Leu Val Asn Asn Val Thr Gln Val Thr Gly Leu Met Gly
                270                 275                 280 gtc ttg ttg aat gca gtc aat tac aaa gtc tca atg gaa gaa att att     1335
Val Leu Leu Asn Ala Val Asn Tyr Lys Val Ser Met Glu Glu Ile Ile
285                 290                 295 ttc aac tac caa aag tgg ctg cca tgg ctt taa tcctactttt gctctatata  1388
Phe Asn Tyr Gln Lys Trp Leu Pro Trp Leu
300                 305 tagtagcata aataaaggac aacaaattta gtattattgt tgttgtccaa acatgttgcc   1448
aatgatatat gctatttccc tgtaatatcc tcatctttcc aatgtatgaa tatgatgatg   1508
tattatatat gacaaataaa gtttctacta gttcttaat                          1547

<210> SEQ ID NO 4
<211> LENGTH: 309
<212> TYPE: PRT
<213> ORGANISM: Jatropha curcas

<400> SEQUENCE: 4

Met Lys Gly Gly Lys Met Asn Leu Ser Ile Met Val Ala Ala Trp Phe
1               5                   10                  15

Cys Trp Ser Cys Ile Ile Phe Gly Trp Ala Ser Ala Arg Glu Ile Val
            20                  25                  30

Cys Pro Phe Ser Ser Asn Gln Asn Tyr Lys Ala Gly Ser Thr Pro Thr
        35                  40                  45

Leu Thr Ile Thr Tyr Asp Ala Ala Asp Lys Lys Asn Tyr Ala Asn
    50                  55                  60

Phe Ile Arg Asp Leu Arg Glu Ala Phe Gly Phe Ser Tyr Ser Ser His
65                  70                  75                  80

Glu Ile Pro Val Leu Arg Ala Thr Val Ala Ala Asn Gln Lys Phe Ile
                85                  90                  95

Val Ala Lys Val Ile Asn Val Ala Asn Leu Glu Val Ser Leu Gly Leu
            100                 105                 110
```

```
Asn Val Val Asn Ala Tyr Leu Val Ala Tyr Lys Ala Gly Gly Thr Ser
            115                 120                 125

Tyr Phe Phe Asn Asp Pro Glu Ser Leu Ala Asp Ala Lys Lys Tyr Leu
        130                 135                 140

Phe Thr Asp Thr Lys Gln Gln Thr Leu Ser Phe Thr Gly Ser Tyr Ala
145                 150                 155                 160

Asp Phe Leu Ser Arg Ala Asn Val His Arg Glu Asp Val Asp Leu Gly
                165                 170                 175

Val Leu Ala Leu Asp Asn Tyr Ile Tyr Ile Leu His Lys Ser Ser Gln
            180                 185                 190

Pro Ala Asp Ile Ala Lys Pro Leu Val Gly Phe Ile Glu Met Val Pro
        195                 200                 205

Glu Ala Ala Arg Phe Lys Tyr Ile Glu Lys Lys Val Leu Thr Gln Ile
    210                 215                 220

Ser Glu Thr Phe Arg Pro Arg Gly Val Ile Ile Ser Leu Glu Asn Asn
225                 230                 235                 240

Trp Gly Asp Leu Ser Tyr Gln Ile Gln Lys Ser Val Asn Gly Ile Phe
                245                 250                 255

Leu Lys Pro Val Gln Leu Gln Arg Glu Asn Tyr Thr Asn Ile Leu Val
            260                 265                 270

Asn Asn Val Thr Gln Val Thr Gly Leu Met Gly Val Leu Leu Asn Ala
        275                 280                 285

Val Asn Tyr Lys Val Ser Met Glu Glu Ile Ile Phe Asn Tyr Gln Lys
    290                 295                 300

Trp Leu Pro Trp Leu
305
```

<210> SEQ ID NO 5
<211> LENGTH: 1583
<212> TYPE: DNA
<213> ORGANISM: Jatropha curcas
<220> FEATURE:
<221> NAME/KEY: misc_feature
<222> LOCATION: (181)..(181)
<223> OTHER INFORMATION: transcripition start site
<220> FEATURE:
<221> NAME/KEY: 5'UTR
<222> LOCATION: (236)..(463)
<220> FEATURE:
<221> NAME/KEY: CDS
<222> LOCATION: (475)..(1404)

<400> SEQUENCE: 5

```
ttcttttttt tttttttttt gacagttgtt attgtttgtc tttattttta catcttatga    60
aactgtcgtt tggtagctaa taatcaaaat aataataaaa aataataata ataaagaaaa   120
aaaaattgac aaaataaagg gcagtttccc tataaaagca ggtgatgggg gaaggcaaaa   180
gaccatctct cgctctcttc ttctttactt ccccgtttgc tcagttgctt tctttgtaag   240
taatattgaa gcctctgccc ttcttttttg ttgacaaatt ccattttttt gttttactaa   300
tagcatgtta atttctagct tctggaaatg agttattat  actttatatg ataaacttgt   360
gaccattcta tctctttta atcattttta taatttatg caaatctatt ataataatcg     420
tattcgtata atgatatttg tgtttcttca tacaactgga caggtgaaat caat atg      477
                                                              Met
                                                                1 aaa ggt gga aag atg aac ctc tcc att atg gtg gct gcc tgg ttt tgc     525
Lys Gly Gly Lys Met Asn Leu Ser Ile Met Val Ala Ala Trp Phe Cys
              5                  10                  15
```

| | |
|---|---:|
| tgg agt agt att ata ttc gga tgg gca tcg gct agg gaa ata gtt tgt<br>Trp Ser Ser Ile Ile Phe Gly Trp Ala Ser Ala Arg Glu Ile Val Cys<br>       20                    25                    30 | 573 |
| cca ttc tca tca aac caa aac tac aaa gct ggt tcc act cca act tta<br>Pro Phe Ser Ser Asn Gln Asn Tyr Lys Ala Gly Ser Thr Pro Thr Leu<br>35                    40                    45 | 621 |
| gcc att act tat gac gct act act gat aag aaa aac tac gcc cag ttc<br>Ala Ile Thr Tyr Asp Ala Thr Thr Asp Lys Lys Asn Tyr Ala Gln Phe<br>50                    55                    60                    65 | 669 |
| att gaa gat cta aga gaa gca ttt gac ttc agt tat tta agc cat aaa<br>Ile Glu Asp Leu Arg Glu Ala Phe Asp Phe Ser Tyr Leu Ser His Lys<br>              70                    75                    80 | 717 |
| ata cca gtc tta cgg gcc acg gtt gct gca aat cag aaa ttt att gta<br>Ile Pro Val Leu Arg Ala Thr Val Ala Ala Asn Gln Lys Phe Ile Val<br>                  85                    90                    95 | 765 |
| gcc aaa gtc ata aat tct ggg gac ata gaa gta tca gta gga tta aac<br>Ala Lys Val Ile Asn Ser Gly Asp Ile Glu Val Ser Val Gly Leu Asn<br>              100                    105                    110 | 813 |
| gtc att aat gca tat cta gtg gct tat aag gta gga agt aat tcc tat<br>Val Ile Asn Ala Tyr Leu Val Ala Tyr Lys Val Gly Ser Asn Ser Tyr<br>115                    120                    125 | 861 |
| ttc ttt aac gat tcg gaa tct ttg gct gat gca aaa aaa aat ctt ttc<br>Phe Phe Asn Asp Ser Glu Ser Leu Ala Asp Ala Lys Lys Asn Leu Phe<br>130                    135                    140                    145 | 909 |
| aca gac aca aac caa caa aca cta gca ttt act ggt agc tat gca gat<br>Thr Asp Thr Asn Gln Gln Thr Leu Ala Phe Thr Gly Ser Tyr Ala Asp<br>                    150                    155                    160 | 957 |
| ttt gaa tct agg gca aag tta cat aga gag gaa gtg gat tta gga gtg<br>Phe Glu Ser Arg Ala Lys Leu His Arg Glu Glu Val Asp Leu Gly Val<br>                  165                    170                    175 | 1005 |
| gtg gca ttg gat aat tac gta tat aca ctt gaa aaa agt tct cag cca<br>Val Ala Leu Asp Asn Tyr Val Tyr Thr Leu Glu Lys Ser Ser Gln Pro<br>180                    185                    190 | 1053 |
| gca gac att gct aaa cct cta gtt ggt ttt atc gaa atg gtt cca gag<br>Ala Asp Ile Ala Lys Pro Leu Val Gly Phe Ile Glu Met Val Pro Glu<br>195                    200                    205 | 1101 |
| gca gca aga ttc aaa tat att gag aaa aaa ata tca act caa att agc<br>Ala Ala Arg Phe Lys Tyr Ile Glu Lys Lys Ile Ser Thr Gln Ile Ser<br>210                    215                    220                    225 | 1149 |
| aaa acc ttt agg ccg cgt ggt gac ata att agc ctt gag aac aac tgg<br>Lys Thr Phe Arg Pro Arg Gly Asp Ile Ile Ser Leu Glu Asn Asn Trp<br>                    230                    235                    240 | 1197 |
| gga gac ctc tct tat caa ata cag aaa tct gtt gat gat gta ttt ctg<br>Gly Asp Leu Ser Tyr Gln Ile Gln Lys Ser Val Asp Asp Val Phe Leu<br>                  245                    250                    255 | 1245 |
| aag cca gtt caa ttg caa cgt gaa aac tat acc aat atc cta gtg aac<br>Lys Pro Val Gln Leu Gln Arg Glu Asn Tyr Thr Asn Ile Leu Val Asn<br>260                    265                    270 | 1293 |
| aat gtc acc caa gta aaa ggt ctc atg gga gtc ttg ttg aat gca gtc<br>Asn Val Thr Gln Val Lys Gly Leu Met Gly Val Leu Leu Asn Ala Val<br>275                    280                    285 | 1341 |
| aat tac aaa gtc tca atg gaa gaa att att ttc aac gac caa aag tgg<br>Asn Tyr Lys Val Ser Met Glu Glu Ile Ile Phe Asn Asp Gln Lys Trp<br>290                    295                    300                    305 | 1389 |
| ctg cca tgg ctt taa tcctactttt gctctatata tagtagcata aataaaggac<br>Leu Pro Trp Leu | 1444 |
| aacaaattta gtattattgt tgttgtccaa acatgttgct aatgatatat gctctttccc | 1504 |
| tgtaatatcc tcgtctttcc aatgtatgaa tatgatgatg aattatatat gacaaataaa | 1564 | gtttctacta gttcttaat                                                    1583

<210> SEQ ID NO 6
<211> LENGTH: 309
<212> TYPE: PRT
<213> ORGANISM: Jatropha curcas

<400> SEQUENCE: 6

Met Lys Gly Gly Lys Met Asn Leu Ser Ile Met Val Ala Ala Trp Phe
1               5                   10                  15

Cys Trp Ser Ser Ile Ile Phe Gly Trp Ala Ser Ala Arg Glu Ile Val
            20                  25                  30

Cys Pro Phe Ser Ser Asn Gln Asn Tyr Lys Ala Gly Ser Thr Pro Thr
        35                  40                  45

Leu Ala Ile Thr Tyr Asp Ala Thr Thr Asp Lys Lys Asn Tyr Ala Gln
    50                  55                  60

Phe Ile Glu Asp Leu Arg Glu Ala Phe Asp Phe Ser Tyr Leu Ser His
65                  70                  75                  80

Lys Ile Pro Val Leu Arg Ala Thr Val Ala Ala Asn Gln Lys Phe Ile
                85                  90                  95

Val Ala Lys Val Ile Asn Ser Gly Asp Ile Glu Val Ser Val Gly Leu
            100                 105                 110

Asn Val Ile Asn Ala Tyr Leu Val Ala Tyr Lys Val Gly Ser Asn Ser
        115                 120                 125

Tyr Phe Phe Asn Asp Ser Glu Ser Leu Ala Asp Ala Lys Lys Asn Leu
    130                 135                 140

Phe Thr Asp Thr Asn Gln Gln Thr Leu Ala Phe Thr Gly Ser Tyr Ala
145                 150                 155                 160

Asp Phe Glu Ser Arg Ala Lys Leu His Arg Glu Glu Val Asp Leu Gly
                165                 170                 175

Val Val Ala Leu Asp Asn Tyr Val Tyr Thr Leu Glu Lys Ser Ser Gln
            180                 185                 190

Pro Ala Asp Ile Ala Lys Pro Leu Val Gly Phe Ile Glu Met Val Pro
        195                 200                 205

Glu Ala Ala Arg Phe Lys Tyr Ile Glu Lys Ile Ser Thr Gln Ile
    210                 215                 220

Ser Lys Thr Phe Arg Pro Arg Gly Asp Ile Ile Ser Leu Glu Asn Asn
225                 230                 235                 240

Trp Gly Asp Leu Ser Tyr Gln Ile Gln Lys Ser Val Asp Asp Val Phe
                245                 250                 255

Leu Lys Pro Val Gln Leu Gln Arg Glu Asn Tyr Thr Asn Ile Leu Val
            260                 265                 270

Asn Asn Val Thr Gln Val Lys Gly Leu Met Gly Val Leu Leu Asn Ala
        275                 280                 285

Val Asn Tyr Lys Val Ser Met Glu Glu Ile Ile Phe Asn Asp Gln Lys
    290                 295                 300

Trp Leu Pro Trp Leu
305

<210> SEQ ID NO 7
<211> LENGTH: 3181
<212> TYPE: DNA
<213> ORGANISM: Jatropha curcas
<220> FEATURE:
<221> NAME/KEY: misc_feature
<222> LOCATION: (2889)..(2889)
<223> OTHER INFORMATION: transcription start site

```
<220> FEATURE:
<221> NAME/KEY: 5'UTR
<222> LOCATION: (2944)..(3170)

<400> SEQUENCE: 7
gtggaaatta gtcagtggag tcaccgaaac ccgatgagcc gtcctcccac atggcccatc    60
cactcacatg tgcaccaggg agccaatccc ccattctggc tgaccagtat aatcctcaca   120
ctatcggtcc tccgattatt tttccactct ctctctctct ctctctctct ctctctctct   180
ctctctcttt tttataccga caggcggcat ctcaatcgtc tccctcaaat ctagatcatc   240
aggtgcacac aacaggaggt caccctgcgg gcaacgatca atctagatc atcaggtgcg    300 cccaaagaga ccaacccatg gttttccata tcatacagat cagagcagta ggtgcacacg   360
ggggcgccga tctcccattt acccggctaa cagaaattag aatcaggatc catataacag   420
aatcagaatc agaattagaa ttaggatcca tataacagaa tcagtctcac aaacccatgg   480
tgacccactt catcccaatt ccacacaaac aaagcatagc attatcacaa cacaattaat   540
caaacattgc aatcaaatgc agacatattg atcagttgaa catcgtaatg caatgcacaa   600
ttagacatcc attttcaaat gcaattaaat aagtaaataa atactattaa taataaacaa   660
caacgataaa ataaatgata ataataaaca ataacaatga aaataaataa atagttaaat   720
aattaaatga ataataaaga taataaataa ataatgagag cactctattt attatgtatt   780
aaattataga attaatctaa ataaacttat taattatgtc attaattaaa actagtctag   840
gttctattga aatttcgaca gcacctcccc taaaatttga ctaaacaaca attcaacact   900
atagtatcaa agcccatccg ttgggcaatt caaatcaact catcccgtcc gccataacct   960
tatttatcaa ttattcgatc aatcaattca cacagcccat ccaccgggca atcaattcaa  1020
ccaacccatc cgcttcaaac tacatgtatc atccatcaaa ctcacatata tacacttaat  1080
agttcaaaat taactaatta caacctata ttgacctcta agcatgattc aatgatatta   1140
ttaattactt taaaactgtt tacttgtcta agccttaaat tataatcctc ccctatcaat  1200
atttattaaa attcctaaat tagcttacat caatattata ccgactgatt cttagcaaaa  1260
ttatatttga tcgattattc attcaaattc aatttaatta actaataatt attaagttta  1320
taatttatac cgaaaatgag gaaattggtc ttagaacaaa ccaattgaga attgggcgac  1380
gattccatta tcagcgcgaa gagaagagaa ttctgtctct cggggcctcg ccggagtgtc  1440
gccggaccgc cgccactagc ccccgtgcac gatggccaga aagtcgttct tgcccagaat  1500
catgcacttc atacaccttt aaaatcaaaa tttcaccaag aactcaaatc catgctccaa  1560
ttgttgagtc tacggtccgt ttggcccaac caacgccgat cgaagcttaa tgccaccatt  1620
agtggtggtt tcaccaccgg agcccaatca tcggaaccaa gggatggaaa acacacgcaa  1680
gaccaagagg agtcgatcga aggtcctctc gctggctata tttgcccgaa acggcgagaa  1740
tcgccagcga atagaaatcg gagggtaccg tcacttcaag catgattcct ttcgcttccg  1800
gcgtctacta cgtgaacgga gaccataggt gggttcctct cgtcgagcac ttgcagttag  1860
ggtgcttggt tgtcggaatc tgtggtcgat ggccggaaaa cacagtgaac aagggaggag  1920
gaggctgtcg cgtgactgga gaagaagaag gagaagagag gaagaaaaag aaaccaagtc  1980
ggtttctaga tcattctggt tcgattcgaa ctgatttggt ctgattcaac gatttggctt  2040
gattttgctc ggtttgtatg tttttcactt ggttttcaat ttatttgtgt ggttttcgaa  2100
aaattaattt gatttccgga tccggattga tttattttga ttatttttaat taggtttcgt  2160 aacatttcct ccataaaaat aaaaatataa ttagtaatca tatttgatttt ttttgggaaa  2220
```

```
ttaatttata tatatacata atagattaat tgttagagtt tcatattatt tctcgaaaat    2280
tttaactgtt ctcaaattga aaattccaat gatatatttg ggcttaggcc caactcgcga    2340
acttgggctc gaattgagat ttttggtatt tatagcccat atagttgaaa atcaagattt    2400
ttgatttaat aaaaattcga aagtttcgaa ataaaaatt cggggtatta caaaaacctt     2460
tgattttttt ggatttcaat atggatttcc tcccttctta tgcatttatt ttttcctttt    2520
ttatgttgaa taaatcttga gtaatctttc tttgatgagc ttaaaacact aaagatgata    2580
gtgttcaaaa gcttgaaatt acttctaaac gtgtcatatt tctcgtttgt cttttatcaa    2640
tttttgtttt ttctaatcat cggtcatcaa atcagcgcc ccacaccgc tatgactcgg      2700 catttccttg gattttcaat aattcttttt cattgggata tgttgttgtt tgtctttatt    2760
ttacatctta tgaaactgtc gtttggttgc taataataat aataataata ataagaaaa     2820 aaaattgaca aaataaaggg ccgggaaggc agtttccta taaaagcagg tgatggggga     2880
aggcaaaaga ccatctcttg ctctcttctt ctttacttcc ccgtttgctc agttgctttc    2940
tttgtaagta atatagaagc ctctgcccct ctttgttgtt gacaaattcc attttttgtt    3000
ttactattag catgttaatt tctagcttct ggaaatgagt ttattatcct ttatatgata    3060
aacttgtgac cattctatct cttttaatt attttttataa ttttatgcaa ttctattaaa    3120
ataatcgtat tcgtataatg atatttgtgt ttcttcatac aactggacag gtgaaatcaa    3180
t                                                                   3181

<210> SEQ ID NO 8
<211> LENGTH: 2087
<212> TYPE: DNA
<213> ORGANISM: Jatropha curcas
<220> FEATURE:
<221> NAME/KEY: misc_feature
<222> LOCATION: (1794)..(1794)
<223> OTHER INFORMATION: transcription start site
<220> FEATURE:
<221> NAME/KEY: 5'UTR
<222> LOCATION: (1853)..(2076)

<400> SEQUENCE: 8
gaaagttaga gttagggtat aattaaaact actcgcaaaa tttgggatat ttttaacgat    60
ttaaccattc tttgagtatt gcttttgtg gaaatataaa atcaatgagg aaaaaaatg      120 atattaagaa ctagattaca agagtagctt ttatacagaa ttatgaataa aaaatatcta   180
gctattatat cttcgagcca ctttctatta cactttgtag ttgcttctat attatccaaa   240
acatacaaac catggaaaag ataagggagc cattgcactt cacaagtagt agaagcaagt   300
gcaatgcttt ctgcttttga tgaggaacgt aaaaaagtct gactgtttgt taagttctag   360
cagactaatt acattatcta aggtaaacac aataacttgt aatagatttg tgtgtgtcta   420
aacagccggc ccagtcgtaa ccattagatg ctttaagcta aagaaaaat tagatgggaa    480 aaataatcta gcatctaggg catccttaat gtagtgaaga gcatgattag gattttttt    540 tttccatcgg ttttctttat ctttatttag ttttcttttct agagtaggat cgtttaaatt   600 tatcttttatt tacttttctt tctagagcag gatcgtttaa aacaaatctt agttttatt   660 tttcggatct atcatagtta atagaccttc gatgttttg ataccctcct agtggggttg    720
tccaattttg atttgttacg ttttctctca tttgatgaag ttattctca ttattaaaga    780 gttttttacgt gatttgtgat ttttcttttct taaaagtcta aaatataaga tgaatcattt   840
attgattgca gtggagactt taattcttcg aatgctgata atttcttttt tcaatagatc    900
```

```
ttggtagcac caccttccta agttaaaatt tgataatttc aaactcttct ataggaggta      960
acaagttttc tcaaggacaa agttcaagac actagttcaa aaatttatt ttatcattct     1020 atttgaaaat agattggtct ttacctagaa gattaatgta ccaaatcata cattggttat     1080
ggaaatatta tgacctactt aagctataat ctttattaaa ggcttgagaa gtttgtaaaa     1140
aaataaaaat aaaataaat aaataaataa ataaatcaat actaagctta agatgagcgt     1200
tagaaaaact agatgatttg agtttgagtt tagtttgttg gtttgataat gctaattttt     1260
aataaattta attttttaaa aaattatagt ttcctttta ttattttccc ttttttacaaa     1320 taaatgttgg aatagaagac tttgttttct tttctttcat tacttttttt tttttttggt     1380
tacatttctt tcattatttt tcatctaagg tttcaccaat aaaaaaataa taataaaaaa     1440
aattataaac gtgtcatatt tctcgtttgt cttttatcaa ttttgtttt ttctaatcaa     1500 cggtcatcaa atcagcgccc cacacccgct atgacgcggc atttatcaat ttttgttttt     1560
tctccttgga ttttcaataa ttcttttca ttgggatttg ttattgtttg tctttctttt     1620 tttttttt tttgacagtt gttattgttt gtctttattt ttacatctta tgaaactgtc     1680
gtttggtagc taataatcaa aataataata aaaataata ataataaaga aaaaaaatt     1740 gacaaaataa agggcagttt ccctataaaa gcaggtgatg ggggaaggca aaagaccatc     1800
tctcgctctc ttcttcttta cttccccgtt tgctcagttg cttctctttgt aagtaatatt     1860 gaagcctctg cccttctttt ttgttgacaa attccatttt tttgtttac taatagcatg     1920 ttaatttcta gcttctggaa atgagtttat tatactttat atgataaact tgtgaccatt     1980
ctatctcttt ttaatcattt ttataatttt atgcaaatct attataataa tcgtattcgt     2040
ataatgatat ttgtgtttct tcatacaact ggacaggtga aatcaat                 2087
```

<210> SEQ ID NO 9
<211> LENGTH: 3465
<212> TYPE: DNA
<213> ORGANISM: Jatropha curcas
<220> FEATURE:
<221> NAME/KEY: misc_feature
<222> LOCATION: (3208)..(3208)
<223> OTHER INFORMATION: transcription start site
<220> FEATURE:
<221> NAME/KEY: 5'UTR
<222> LOCATION: (3228)..(3454)

<400> SEQUENCE: 9

```
gcttgtgata actaacatgt cccagatgag cgtgccacaa atcagttgtc tcactcttcc       60
ttgttctgtc aacataggct tcttgtgctg acatgacgta gattgattct actcgccgtc      120
cttccatgac tggatctctg attaatttaa ggttatgata aaccttaaca ttatcaagac      180
cgaacaccac ataattacct gcacttgtta tttatgatac agagagcaag ttttctctca      240
ttcttggctc atggtaaatc atctgtaact ccatttctc cttactggag ggagaaacaa      300
tggttgtctt tccaatgtga gctattggca atctcgtgtt atttgttgtg actacaacac      360
gacttccatc ataatcagat acatccgata atttttttt tgtttcctgt catgtgatta      420
gaacttccag aatcaactat ccaatcatca tcatagttga ctctatcact tacagatatt      480
aatgacgact cctgctcggg tcttttcatc atcaactcta ctggcttctg tggcaaatat      540
tcttcctcct gaacaaagaa actgtgaata tcccattcct cttcactttg ttgctagttc      600
tgggttgatg ctatgtttcc ttctactcat ctgcttcgac attctcgggc gaaatgtcct      660
tttttgttgc acttatagca atgatcactt tctcgccagt cgtctttcct ttgtcctggc      720
```

```
cttgctcccc cttgctgtga tggtctccac ttttgctttc tccatccttg ttgattgctc    780 ctttctttc caccatctac tctcgcaacg tttcgaaatc ccctattttt agtaaagaga    840
gctttctcat catccttcaa agcaacttta gacatttttt catccaaagt ctcttcattg    900
gacaagatac tctctaactc gtctaaggtt ggttgtgtag cccaaccatg agtagtagtc    960
acaagaccct taaattcagg tcctagacca tggatgatga tcctcctcat ccttgtctcg   1020
ttgatctcat tgtctggctc taatttcgaa atctcctcac ataaagattt tactttagaa   1080
aagtattgac ttacagtgag gttctattgc gagattgaga acaactcatt ttcaagccgt   1140
tgcagttttg cttcgttctt cttggcaaaa gcagacttga ggatgtccca tgtttccttt   1200
ggtgttttag ctaacttgat ctgttgcatc tgctcatctt ctattgcaat cattagcaca   1260
tacatcgcct tctcgcattt tgtctcccac tctttcagag cttttgcatc cccaactggt   1320
ggtgtagtat tatctcctct gacgatatcc cataagtctt gacctatgag atgatatctc   1380
atatgggtac tccaattccc ataattgttg ctatttagct tctcgatgct attagcaact   1440
ccagaaaaat ccgccataag atactggtgt tcctgacact aaccaatgca cgatggtccc   1500
tgaccaatta cgatcacaat ccttgcttat gaatttgctt caataatagt ccctaactgt   1560
taattccagc agagtaacga taccatccac ttgtcaatga acaccacaaa ataccacggc   1620
tacaacaact accaccacaa ccaggctctg atactacttg gtggatatca gtacaatgat   1680
aaactttgct tcttggactt ggttttgat tggtgcttac aaatacgagg aggggtggta   1740
tttataggca tttccacctc ctcaatgtac ggctaagatt tgctttcaaa aatggatggt   1800
ctagattaca agaaacattc tagagttagg tagacatttc acaaaatatc tttgagtggg   1860
agtattctag aatgccctag gtatttacac actttgtgag cttggatcaa ccatctttgg   1920
gctaaaggct tccctaatct tggcttatta tagcagccca ttttggtggt gacttttctg   1980
ctttaagcta aaagaaaaat tagattggaa aaataatcta gcatctaggg catccttaat   2040
atagtgaaga gcatgattag gatttcgttt tcttttcatc ggttttcttt atctttattt   2100
agttttcttt ctagagtagg atggtttaaa acaaatctta attttattt ctcatatcta   2160 tcatagttaa cagaccttca atgttttgat atcctcctag tggggttgtc caattttgat   2220
ttgttacgtt ttctctcctt tgatgaagtt atttctcatt attaaagagt ttttacgtag   2280
tttgtgattt ttctttcttg atagtctaaa atataagatg aatcatttat tgattgcagt   2340
cgaaaacttc aattcttga atgctgataa tttttttttt caatagatct tggtagcacc   2400
accttcctcc attaaaattt gataatttca aactcttcta taggaggtag caagttttct   2460
caaagacact tcaagacact agttcaaaaa ttttattta tcattctgtt tgaaaataga   2520 ttggtctta cctagaagat taatgtcttt tgtcaaaatc atatgtttat tatggaacta   2580
ttatgaccca cttaagctat aatctttatt aaagagttgc caagttttt tttttttt   2640 ttttttttt ttaaaaaaaa aaaagcaat actaagctta agatgggcct tagagaaaca   2700
gatgatttga gttgagttt agttgttgg tttgataatg ctaattttta ataaatttaa   2760 ttttttaaa aaatatagtt tccttttat tattttccct ttttacaaat aaatattgga   2820
atagaagact ttgttttctt ttctttcatt acttttttt tttggggtta catttctttc   2880 attattttc atctaaggtt tcaccaataa aaaataata ataaaaaaaa aattctaaac   2940
gtgtcatatt ttggtttatc aatttggtt tttttttaat caacggtcat caaatcagcg   3000
ccccacaccc gctatgacgc ggcatttcct tgcattttca ataattcttt ttcattggga   3060
```

```
tttgttgttg tttgtctta ttttacatct tatgaaactg tcgtttggta gctaataata    3120
ataataataa taataataat aaagaaaaaa aattgacaaa ataaagggca gtttccctat    3180
aaaagcaggt gatgggggaa ggcaaaagac catctctcgc tttctttgta agtaatagtg    3240
aagcctctgc ccttcttttt tgttgacaaa ttccattttt tgttttacta atagcatgtt    3300
aatttctagc ttctggaaat gagtttatta tcctttatat gataaacttg tgaacattct    3360
atctcttttt aattattttt ataatttat gcaaagctat taaaataatc gtattcgtat    3420
aatgatattt gtgtttcttc atacaactgg acaggtgaaa tcaat    3465
```

<210> SEQ ID NO 10
<211> LENGTH: 309
<212> TYPE: PRT
<213> ORGANISM: Jatropha curcas

<400> SEQUENCE: 10

```
Met Lys Gly Gly Lys Met Asn Leu Ser Ile Met Val Ala Ala Trp Phe
1               5                   10                  15

Cys Trp Ser Ser Ile Ile Phe Gly Trp Ala Ser Ala Arg Glu Ile Val
            20                  25                  30

Cys Pro Phe Ser Ser Asn Gln Asn Tyr Lys Ala Gly Ser Thr Pro Thr
        35                  40                  45

Leu Ala Ile Thr Tyr Asp Ala Thr Thr Asp Lys Lys Asn Tyr Ala Gln
    50                  55                  60

Phe Ile Glu Asp Leu Arg Glu Ala Phe Asp Phe Ser Tyr Leu Ser His
65                  70                  75                  80

Lys Ile Pro Val Leu Arg Ala Thr Val Ala Ala Asn Gln Lys Phe Ile
                85                  90                  95

Val Ala Lys Val Ile Asn Ser Gly Asp Ile Glu Val Ser Val Gly Leu
            100                 105                 110

Asn Val Ile Asn Ala Tyr Leu Val Ala Tyr Lys Val Gly Ser Asn Ser
        115                 120                 125

Tyr Phe Phe Asn Asp Ser Glu Ser Leu Ala Asp Ala Lys Lys Asn Leu
    130                 135                 140

Phe Thr Asp Thr Asn Gln Gln Thr Leu Ala Phe Thr Gly Ser Tyr Ala
145                 150                 155                 160

Asp Phe Glu Ser Arg Ala Lys Leu His Arg Glu Glu Val Asp Leu Gly
                165                 170                 175

Val Val Ala Leu Asp Asn Tyr Val Tyr Thr Leu Glu Lys Ser Ser Gln
            180                 185                 190

Pro Ala Asp Ile Ala Lys Pro Leu Val Gly Phe Ile Glu Met Val Pro
        195                 200                 205

Glu Ala Ala Arg Phe Lys Tyr Ile Glu Lys Lys Ile Ser Thr Gln Ile
    210                 215                 220

Ser Lys Thr Phe Arg Pro Arg Gly Asp Ile Ile Ser Leu Glu Asn Asn
225                 230                 235                 240

Trp Gly Asp Leu Ser Tyr Gln Ile Gln Lys Ser Val Asp Val Phe
                245                 250                 255

Leu Lys Pro Val Gln Leu Gln Arg Glu Asn Tyr Thr Asn Ile Leu Val
            260                 265                 270

Asn Asn Val Thr Gln Val Lys Gly Leu Met Gly Val Leu Leu Asn Ala
        275                 280                 285

Val Asn Tyr Lys Val Ser Met Glu Glu Ile Ile Phe Asn Asp Gln Lys
    290                 295                 300
```

```
Trp Leu Pro Trp Leu
305

<210> SEQ ID NO 11
<211> LENGTH: 309
<212> TYPE: PRT
<213> ORGANISM: Jatropha curcas

<400> SEQUENCE: 11

Met Lys Gly Gly Lys Met Asn Leu Ser Ile Met Val Ala Ala Trp Phe
1               5                   10                  15

Cys Trp Ser Ser Ile Ile Phe Gly Trp Ala Ser Ala Arg Glu Ile Val
            20                  25                  30

Cys Pro Phe Ser Ser Asn Gln Asn Tyr Lys Ala Gly Ser Thr Pro Thr
                35                  40                  45

Leu Val Ile Thr Tyr Asp Ala Thr Thr Asp Lys Lys Asn Tyr Ala Gln
            50                  55                  60

Phe Ile Glu Asp Leu Arg Glu Ala Phe Asp Phe Ser Tyr Leu Ser His
65                  70                  75                  80

Lys Ile Pro Val Leu Arg Ala Thr Val Ala Ala Asn Gln Lys Phe Ile
                85                  90                  95

Val Ala Lys Val Ile Asn Ser Gly Asp Ile Glu Val Ser Val Gly Leu
            100                 105                 110

Asn Val Ile Asn Ala Tyr Leu Val Ala Tyr Lys Val Gly Ser Asn Ser
        115                 120                 125

Tyr Phe Phe Asn Asp Ser Glu Ser Leu Ala Asp Ala Lys Lys Asn Leu
    130                 135                 140

Phe Thr Asp Thr Asn Gln Gln Thr Leu Ala Phe Thr Gly Ser Tyr Ala
145                 150                 155                 160

Asp Phe Glu Ser Arg Ala Lys Leu His Lys Glu Val Asp Leu Gly
                165                 170                 175

Val Val Ala Leu Asp Asn Tyr Val Tyr Thr Leu Glu Lys Ser Ser Gln
            180                 185                 190

Pro Ala Asp Ile Ala Lys Pro Leu Val Gly Phe Ile Glu Met Val Pro
        195                 200                 205

Glu Ala Ala Arg Phe Lys Tyr Ile Glu Lys Lys Ile Ser Thr Gln Ile
    210                 215                 220

Ser Lys Thr Phe Arg Pro Arg Gly Asp Ile Ile Ser Leu Glu Asn Asn
225                 230                 235                 240

Trp Gly Asp Leu Ser Tyr Gln Ile Gln Lys Ser Val Asp Val Phe
                245                 250                 255

Leu Lys Pro Val Gln Leu Gln Arg Glu Asn Tyr Thr Asn Ile Leu Val
            260                 265                 270

Asn Asn Val Thr Gln Val Lys Gly Leu Met Gly Val Leu Leu Asn Ala
        275                 280                 285

Val Asn Tyr Lys Val Ser Met Glu Glu Ile Ile Phe Asn Asp Gln Lys
    290                 295                 300

Trp Leu Pro Trp Leu
305

<210> SEQ ID NO 12
<211> LENGTH: 309
<212> TYPE: PRT
<213> ORGANISM: Jatropha curcas

<400> SEQUENCE: 12
```

Met Lys Gly Gly Lys Met Asn Leu Ser Ile Met Val Ala Ala Trp Phe
1               5                   10                  15

Cys Trp Ser Ser Ile Ile Phe Gly Trp Ala Ser Ala Arg Glu Ile Val
            20                  25                  30

Cys Pro Phe Ser Ser Asn Gln Asn Tyr Lys Ala Gly Ser Thr Pro Thr
            35                  40                  45

Leu Val Ile Thr Tyr Asp Ala Thr Asp Lys Lys Asn Tyr Ala Gln
50                  55                  60

Phe Ile Glu Asp Leu Arg Glu Ala Phe Asp Phe Ser Tyr Leu Ser His
65                  70                  75                  80

Lys Ile Pro Val Leu Arg Ala Thr Val Ala Ala Asn Gln Lys Phe Ile
                85                  90                  95

Val Ala Lys Val Ile Asn Ser Gly Asp Ile Glu Val Ser Val Gly Leu
            100                 105                 110

Asn Val Ile Asn Ala Tyr Leu Val Ala Tyr Lys Val Gly Ser Asn Ser
            115                 120                 125

Tyr Phe Phe Asn Asp Ser Glu Ser Leu Ala Asp Ala Lys Lys Asn Leu
        130                 135                 140

Phe Thr Asp Thr Asn Gln Gln Thr Leu Ala Phe Thr Gly Ser Tyr Ala
145                 150                 155                 160

Asp Phe Glu Ser Arg Ala Lys Leu His Arg Glu Val Asp Leu Gly
                165                 170                 175

Val Val Ala Leu Asp Asn Tyr Val Tyr Thr Leu Glu Lys Ser Ser Gln
            180                 185                 190

Pro Ala Asp Ile Ala Lys Pro Leu Val Gly Phe Ile Glu Met Val Pro
        195                 200                 205

Glu Ala Ala Arg Phe Lys Tyr Ile Glu Lys Lys Ile Ser Thr Gln Ile
    210                 215                 220

Ser Lys Thr Phe Arg Pro Arg Gly Asp Ile Ile Ser Leu Glu Asn Asn
225                 230                 235                 240

Trp Gly Asp Leu Ser Tyr Gln Ile Gln Lys Ser Val Asp Asp Val Phe
                245                 250                 255

Leu Lys Pro Val Gln Leu Gln Arg Glu Asn Tyr Thr Asn Ile Leu Val
            260                 265                 270

Asn Asn Val Thr Gln Val Lys Gly Leu Met Gly Val Leu Leu Asn Ala
            275                 280                 285

Val Asn Tyr Lys Val Ser Met Glu Glu Ile Ile Phe Asn Asp Gln Lys
        290                 295                 300

Trp Leu Pro Trp Leu
305

<210> SEQ ID NO 13
<211> LENGTH: 293
<212> TYPE: PRT
<213> ORGANISM: Jatropha curcas

<400> SEQUENCE: 13

Met Lys Gly Gly Lys Met Asn Leu Ser Ile Met Val Ala Ala Trp Phe
1               5                   10                  15

Cys Trp Ser Cys Ile Ile Phe Gly Trp Ala Ser Ala Arg Glu Ile Val
            20                  25                  30

Cys Pro Phe Ser Ser Asn Gln Asn Tyr Lys Ala Gly Ser Thr Pro Thr
            35                  40                  45

Leu Thr Ile Thr Tyr Asp Ala Ala Ala Asp Lys Lys Asn Tyr Ala Gln
50                  55                  60

Phe Ile Lys Asp Leu Arg Glu Ala Phe Gly Phe Ser Tyr Ser Ser His
65                  70                  75                  80

Glu Ile Pro Val Leu Arg Ala Thr Val Ala Pro Asn Gln Lys Phe Ile
                85                  90                  95

Val Ala Lys Val Ile Asn Val Ala Asn Leu Glu Val Ser Leu Gly Leu
            100                 105                 110

Asn Val Val Asn Ala Tyr Leu Val Gly Tyr Lys Val Gly Gly Thr Ser
            115                 120                 125

Tyr Phe Phe Asn Asp Pro Glu Ser Leu Ala Asp Ala Lys Thr Tyr Leu
            130                 135                 140

Phe Thr Asp Thr Lys Gln Gln Thr Leu Ser Phe Thr Gly Ser Tyr Ala
145                 150                 155                 160

Asp Phe Leu Ser Arg Ala Asn Val His Arg Glu Asp Val Asp Leu Gly
                165                 170                 175

Val Gln Ala Leu Asp Asn Tyr Ile Tyr Thr Leu Glu Lys Ser Ser Lys
            180                 185                 190

Pro Ala Asp Ile Ala Lys Pro Leu Val Gly Phe Ile Glu Met Val Pro
            195                 200                 205

Glu Ala Ala Arg Phe Lys Tyr Ile Glu Lys Val Leu Ser Gln Ile
            210                 215                 220

Ser Lys Thr Leu Arg Pro Gly Gly Asp Ile Ile Ser Leu Glu Asn Asn
225                 230                 235                 240

Trp Gly Asp Leu Ser Tyr Gln Ile Gln Lys Cys Val Asn Gly Val Phe
                245                 250                 255

Leu Lys Pro Val Gln Leu Gln Arg Glu Asn Tyr Thr Asn Ile Leu Val
            260                 265                 270

Asn Asn Val Thr Gln Val Ala Gly Val Met Gly Val Leu Leu Asn Ala
            275                 280                 285

Val Asn Tyr Lys Val
            290

<210> SEQ ID NO 14
<211> LENGTH: 293
<212> TYPE: PRT
<213> ORGANISM: Jatropha curcas

<400> SEQUENCE: 14

Met Lys Gly Gly Lys Met Asn Leu Ser Ile Met Val Ala Ala Trp Phe
1               5                   10                  15

Cys Trp Ser Cys Ile Ile Phe Gly Trp Ala Ser Ala Arg Glu Ile Val
            20                  25                  30

Cys Pro Phe Ser Ser Asn Gln Asn Tyr Lys Ala Gly Ser Thr Pro Thr
            35                  40                  45

Leu Thr Ile Thr Tyr Asp Ala Ala Asp Lys Lys Asn Tyr Ala Asn
50                  55                  60

Phe Ile Arg Asp Leu Arg Glu Ala Phe Gly Phe Ser Tyr Ser Ser His
65                  70                  75                  80

Glu Ile Pro Val Leu Arg Ala Thr Val Ala Ala Asn Gln Lys Phe Ile
                85                  90                  95

Val Ala Lys Val Ile Asn Val Ala Asn Leu Glu Val Ser Leu Gly Leu
            100                 105                 110

Asn Val Val Asn Ala Tyr Leu Val Gly Tyr Lys Val Gly Gly Thr Ser
            115                 120                 125

Tyr Phe Phe Asn Asp Pro Glu Ser Leu Ala Asp Ala Lys Thr Tyr Leu

```
                130             135             140
Phe Thr Asp Thr Lys Gln Gln Thr Leu Ser Phe Thr Gly Ser Tyr Ala
145                 150                 155                 160

Asp Phe Leu Ser Arg Ala Asn Val His Arg Glu Asp Val Asp Leu Gly
            165                 170                 175

Val Gln Ala Leu Asp Asn Tyr Ile Tyr Thr Leu Glu Lys Ser Ser Lys
        180                 185                 190

Pro Ala Asp Ile Ala Lys Pro Leu Val Gly Phe Ile Glu Met Val Pro
            195                 200                 205

Glu Ala Ala Arg Phe Glu Tyr Ile Glu Lys Lys Ile Ser Thr Gln Ile
    210                 215                 220

Ser Lys Thr Phe Arg Pro Arg Gly Asp Ile Ile Ser Leu Glu Asn Asn
225                 230                 235                 240

Trp Gly Asp Leu Ser Tyr Gln Ile Gln Lys Ser Val Asp Asp Val Phe
                245                 250                 255

Leu Lys Pro Val Gln Leu Gln Arg Glu Asn Tyr Thr Asn Ile Leu Val
            260                 265                 270

Asn Asn Val Thr Gln Val Lys Gly Leu Met Gly Val Leu Leu Asn Ala
        275                 280                 285

Val Lys Tyr Lys Val
    290
```

```
<210> SEQ ID NO 15
<211> LENGTH: 32
<212> TYPE: DNA
<213> ORGANISM: Jatropha curcas

<400> SEQUENCE: 15
aactgcagat ggtgagcaag ggcgaggagc tg                              32

<210> SEQ ID NO 16
<211> LENGTH: 34
<212> TYPE: DNA
<213> ORGANISM: Jatropha curcas

<400> SEQUENCE: 16
ggggtacctt acttgtacag ctcgtccatg ccgt                            34

<210> SEQ ID NO 17
<211> LENGTH: 23
<212> TYPE: DNA
<213> ORGANISM: Jatropha curcas

<400> SEQUENCE: 17
gctggttcca ctccaacttt aac                                        23

<210> SEQ ID NO 18
<211> LENGTH: 30
<212> TYPE: DNA
<213> ORGANISM: Jatropha curcas

<400> SEQUENCE: 18
cgggatccgg tacttcctat ttctttaacg                                 30

<210> SEQ ID NO 19
<211> LENGTH: 25
<212> TYPE: DNA
<213> ORGANISM: Jatropha curcas

<400> SEQUENCE: 19
```
tcagactttg tatttgactg cattc                                               25

<210> SEQ ID NO 20
<211> LENGTH: 31
<212> TYPE: DNA
<213> ORGANISM: Jatropha curcas

<400> SEQUENCE: 20
cccaagctta attatctaat gcctgcaccc c                                        31

<210> SEQ ID NO 21
<211> LENGTH: 33
<212> TYPE: DNA
<213> ORGANISM: Jatropha curcas

<400> SEQUENCE: 21
cccaagcttc actaggatat tggtatagtt ttc                                      33

<210> SEQ ID NO 22
<211> LENGTH: 20
<212> TYPE: DNA
<213> ORGANISM: Jatropha curcas

<400> SEQUENCE: 22
gtctgctggc tttgaacttt                                                     20

<210> SEQ ID NO 23
<211> LENGTH: 20
<212> TYPE: DNA
<213> ORGANISM: Jatropha curcas

<400> SEQUENCE: 23 caccccctaaa tccacatcct                                                    20

<210> SEQ ID NO 24
<211> LENGTH: 36
<212> TYPE: DNA
<213> ORGANISM: Jatropha curcas

<400> SEQUENCE: 24
ggccacgcgt cgactagtac gggggggggg gggggg                                   36

<210> SEQ ID NO 25
<211> LENGTH: 20
<212> TYPE: DNA
<213> ORGANISM: Jatropha curcas

<400> SEQUENCE: 25
ggccacgcgt cgactagtac                                                     20

<210> SEQ ID NO 26
<211> LENGTH: 20
<212> TYPE: DNA
<213> ORGANISM: Jatropha curcas

<400> SEQUENCE: 26
gggcatcggc tagggaaata                                                     20

<210> SEQ ID NO 27
<211> LENGTH: 23
<212> TYPE: DNA
<213> ORGANISM: Jatropha curcas -continued

```
<400> SEQUENCE: 27
tctcatcaaa ccaaaactac aaa                                         23

<210> SEQ ID NO 28
<211> LENGTH: 20
<212> TYPE: DNA
<213> ORGANISM: Jatropha curcas

<400> SEQUENCE: 28
agaggtctcc ccagttgttc                                             20

<210> SEQ ID NO 29
<211> LENGTH: 18
<212> TYPE: DNA
<213> ORGANISM: Jatropha curcas

<400> SEQUENCE: 29
tgaatcttgc tgcctctg                                               18

<210> SEQ ID NO 30
<211> LENGTH: 20
<212> TYPE: DNA
<213> ORGANISM: Jatropha curcas

<400> SEQUENCE: 30
gggcatcggc tagggaaata                                             20

<210> SEQ ID NO 31
<211> LENGTH: 19
<212> TYPE: DNA
<213> ORGANISM: Jatropha curcas

<400> SEQUENCE: 31
gagaggatgt ggatttagg                                              19

<210> SEQ ID NO 32
<211> LENGTH: 22
<212> TYPE: DNA
<213> ORGANISM: Jatropha curcas

<400> SEQUENCE: 32
cttcaagaca ctagttcaaa aa                                          22

<210> SEQ ID NO 33
<211> LENGTH: 21
<212> TYPE: DNA
<213> ORGANISM: Jatropha curcas

<400> SEQUENCE: 33
tgatgagaat ggacaaacta t                                           21

<210> SEQ ID NO 34
<211> LENGTH: 24
<212> TYPE: DNA
<213> ORGANISM: Jatropha curcas

<400> SEQUENCE: 34
ccataaccaa tgtatgattt ggta                                        24

<210> SEQ ID NO 35
<211> LENGTH: 16
<212> TYPE: DNA
<213> ORGANISM: Jatropha curcas
```

```
<220> FEATURE:
<221> NAME/KEY: misc_feature
<222> LOCATION: (1)..(16)
<223> OTHER INFORMATION: n is any nucleotide

<400> SEQUENCE: 35
ngtcgaswga nawgaa                                                    16

<210> SEQ ID NO 36
<211> LENGTH: 18
<212> TYPE: DNA
<213> ORGANISM: Jatropha curcas

<400> SEQUENCE: 36
cccaagtaaa aggtctca                                                  18

<210> SEQ ID NO 37
<211> LENGTH: 32
<212> TYPE: DNA
<213> ORGANISM: Jatropha curcas

<400> SEQUENCE: 37
cggaattcgt attatttgga tggtagaaaa tt                                  32

<210> SEQ ID NO 38
<211> LENGTH: 19
<212> TYPE: DNA
<213> ORGANISM: Jatropha curcas

<400> SEQUENCE: 38
gatatttgtg tttcttcat                                                 19

<210> SEQ ID NO 39
<211> LENGTH: 22
<212> TYPE: DNA
<213> ORGANISM: Jatropha curcas

<400> SEQUENCE: 39
tttgttgtcc tttatttatg ct                                             22

<210> SEQ ID NO 40
<211> LENGTH: 20
<212> TYPE: DNA
<213> ORGANISM: Jatropha curcas

<400> SEQUENCE: 40
tttacttccc cgtttgctca                                                20

<210> SEQ ID NO 41
<211> LENGTH: 24
<212> TYPE: DNA
<213> ORGANISM: Jatropha curcas

<400> SEQUENCE: 41
tatagcatta gcaacaataa taat                                           24

<210> SEQ ID NO 42
<211> LENGTH: 23
<212> TYPE: DNA
<213> ORGANISM: Jatropha curcas

<400> SEQUENCE: 42
cattagcaac atgtttggac aac                                            23
```

```
<210> SEQ ID NO 43
<211> LENGTH: 26
<212> TYPE: DNA
<213> ORGANISM: Jatropha curcas

<400> SEQUENCE: 43
caccccatta cttatgacgc tactac                                        26

<210> SEQ ID NO 44
<211> LENGTH: 22
<212> TYPE: DNA
<213> ORGANISM: Jatropha curcas

<400> SEQUENCE: 44
gtaggattaa agccatggca gc                                            22

<210> SEQ ID NO 45
<211> LENGTH: 23
<212> TYPE: DNA
<213> ORGANISM: Escherichia coli

<400> SEQUENCE: 45
gtcagtggca gtgaagggcg aac                                           23

<210> SEQ ID NO 46
<211> LENGTH: 23
<212> TYPE: DNA
<213> ORGANISM: Escherichia coli

<400> SEQUENCE: 46
ttccatacct gttcaccgac gac                                           23

<210> SEQ ID NO 47
<211> LENGTH: 19
<212> TYPE: DNA
<213> ORGANISM: Escherichia coli

<400> SEQUENCE: 47
gtggcagtga agggcgaac                                                19

<210> SEQ ID NO 48
<211> LENGTH: 19
<212> TYPE: DNA
<213> ORGANISM: Escherichia coli

<400> SEQUENCE: 48
aggtacggta ggagttggc                                                19

<210> SEQ ID NO 49
<211> LENGTH: 21
<212> TYPE: DNA
<213> ORGANISM: Jatropha curcas

<400> SEQUENCE: 49
tgcagtcaat tacaaagtct g                                             21

<210> SEQ ID NO 50
<211> LENGTH: 22
<212> TYPE: DNA
<213> ORGANISM: Jatropha curcas

<400> SEQUENCE: 50
agtaaaaggt ctcatgggag tc                                            22
```

<210> SEQ ID NO 51
<211> LENGTH: 20
<212> TYPE: DNA
<213> ORGANISM: Jatropha curcas

<400> SEQUENCE: 51
taatggtccc tctggatgtg                                              20

<210> SEQ ID NO 52
<211> LENGTH: 23
<212> TYPE: DNA
<213> ORGANISM: Jatropha curcas

<400> SEQUENCE: 52
agaaaagaaa agaaaaaagc agc                                          23

<210> SEQ ID NO 53
<211> LENGTH: 862
<212> TYPE: DNA
<213> ORGANISM: Jatropha curcas

<400> SEQUENCE: 53
ggcatcggct agggaaatag tttgtccatt ctcatcaaac caaaactaca aagctggttc    60
ccctccaact ttaaccatta cttatgacgc tactactgat aagaaaaact acgcccagtt   120
cattaaagat ctaagagaag catttggctt cagttattca agccatgaaa taccagtctt   180
acgggccaca gttgctccaa atcagaaatt tattgtagcc aaagtcataa atgtagcgaa   240
tttagaagta tcattaggat taaacgtcgt taatgcgtat ttagtgggtt ataaggtagg   300
aggtacttcc tatttcttta acgatccgga atctttggct gatgcaaaaa catatctttt   360
cacagacaca aagcaacaaa cgctatcatt tactggtagc tatgcagatt ttctatctag   420
ggcaaacgta cacagagagg atgtggattt aggggtgcag gcattagata attacatata   480
tacacttgaa aaagttcaa agccagcaga cattgctaaa cctctagttg gttttatcga    540
aatggttcca gaggcagcaa gattcaaata tattgagaaa aaagtattaa gtcaaattag   600
caaaaccttt aggccgggtg gtgacataat tagccttgag aacaactggg gagacctctc   660
ttatcaaata cagaaatgtg taatggtgt atttctgaag ccagttcaat tacaacgtga    720
aaactatacc aatatcctag tgaacaatgt cacccaagta gcaggtgtca tgggagtctt   780
gttgaatgca gtcaattaca aagtctgaat ggaagaaatt attttcaact accaaaagtg   840
gctgccatgg ctttaatcct ac                                            862

<210> SEQ ID NO 54
<211> LENGTH: 1161
<212> TYPE: DNA
<213> ORGANISM: Jatropha curcas

<400> SEQUENCE: 54
gaccatctct tgctctcttc ttctttactt ccccgtttgc tcagttgctt tctttgtgaa    60
atcaatatga aggtggaaa gatgaatctc tccattatgg tggctgcatg gttttgctgg   120
agtagtatta tattcggatg ggcatcggct agggaaatag tttgtccatt ctcatcaaac   180
caaaactaca agctggttc ccctccaact ttaaccatta cttatgacgc tactactgat    240
aagaaaaact acgcccagtt cattaaagat ctaagagaag catttggctt cagttattca   300
agccatgaaa taccagtctt acgggccaca gttgctccaa atcagaaatt tattgtagcc   360

| | |
|---|---|
| aaagtcataa atgtagcgaa tttagaagta tcattaggat taaacgtcgt taatgcgtat | 420 |
| ttagtgggtt ataaggtagg aggtacttcc tatttcttta acgatccgga atctttggct | 480 |
| gatgcaaaaa catatctttt cacagacaca aagcaacaaa cgctatcatt tactggtagc | 540 |
| tatgcagatt ttctatctag ggcaaacgta cacagagagg atgtggattt aggggtgcag | 600 |
| gcattagata attacatata tacacttgaa aaaagttcaa agccagcaga cattgctaaa | 660 |
| cctctagttg gttttatcga aatggttcca gaggcagcaa gattcaaata tattgagaaa | 720 |
| aaagtattaa gtcaaattag caaaaccttt aggccgggtg gtgacataat tagccttgag | 780 |
| aacaactggg gagacctctc ttatcaaata cagaaatgtg taaatggtgt atttctgaag | 840 |
| ccagttcaat tacaacgtga aaactatacc aatatcctag tgaacaatgt cacccaagta | 900 |
| gcaggtgtca tgggagtctt gttgaatgca gtcaattaca aagtctgaat ggaagaaatt | 960 |
| attttcaact accaaaagtg gctgccatgg ctttaatcct acttttgctc tatatataga | 1020 |
| gtagcataaa taaggacaa caaatttatt attattgttg ctaatgctat atgctatttc | 1080 |
| cctgtaatat cctcatcttt ccaatgtatg aatatgatga tgaattatat atgacaaata | 1140 |
| aagtttctac tagttcttaa t | 1161 |

<210> SEQ ID NO 55
<211> LENGTH: 1176
<212> TYPE: DNA
<213> ORGANISM: Jatropha curcas

<400> SEQUENCE: 55

| | |
|---|---|
| gaccatctct cgctctcttc ttctttactt ccccgtttgc tcagttgctt tctttgtgaa | 60 |
| atcaatatga aggtggaaa gatgaacctc tccattatgg tggctgcctg gttttgctgg | 120 |
| agtagtatta tattcggatg ggcatcggct agggaaatag tttgtccatt ctcatcaaac | 180 |
| caaaactaca aagctggttc cactccaact ttagccatta cttatgacgc tactactgat | 240 |
| aagaaaaact acgcccagtt cattgaagat ctaagagaag catttgactt cagttatttta | 300 |
| agccataaaa taccagtctt acgggccacg gttgctgcaa atcagaaatt tattgtagcc | 360 |
| aaagtcataa attctgggga catagaagta tcagtaggat taaacgtcat taatgcatat | 420 |
| ctagtggctt ataaggtagg aagtaattcc tatttcttta acgattcgga atctttggct | 480 |
| gatgcaaaaa aaaatctttt cacagacaca aaccaacaaa cactagcatt tactggtagc | 540 |
| tatgcagatt ttgaatctag ggcaaagtta catagagagg aagtggattt aggagtggtg | 600 |
| gcattggata attacgtata tacacttgaa aaaagttctc agccagcaga cattgctaaa | 660 |
| cctctagttg gttttatcga aatggttcca gaggcagcaa gattcaaata tattgagaaa | 720 |
| aaaatatcaa ctcaaattag caaaaccttt aggccgcgtg gtgacataat tagccttgag | 780 |
| aacaactggg gagacctctc ttatcaaata cagaaatctg ttgatgatgt atttctgaag | 840 |
| ccagttcaat tgcaacgtga aaactatacc aatatcctag tgaacaatgt cacccaagta | 900 |
| aaaggtctca tgggagtctt gttgaatgca gtcaattaca aagtctcaat ggaagaaatt | 960 |
| attttcaacg accaaaagtg gctgccatgg ctttaatcct acttttgctc tatatatagt | 1020 |
| agcataaata aaggacaaca aatttagtat tattgttgtt gtccaaacat gttgctaatg | 1080 |
| atatatgctc tttccctgta atatcctcgt cttttccaatg tatgaatatg atgatgaatt | 1140 |
| atatatgaca aataaagttt ctactagttc ttaatt | 1176 |

<210> SEQ ID NO 56
<211> LENGTH: 1140

```
<212> TYPE: DNA
<213> ORGANISM: Jatropha curcas

<400> SEQUENCE: 56
gaccatctct cgctttcttt gtgaaatcaa tatgaaaggt ggcaagatga acctctctat      60
tatggtggct gcatggtttt gctggagttg tattatattc ggatgggcat cggctaggga     120
aatagtttgt ccattctcat caaaccaaaa ctacaaagct ggttccactc caactttaac     180
cattacttat gacgctgctg ctgataagaa aaactacgcc aacttcatta gagatctaag     240
agaagcattt ggcttcagtt attcaagcca tgaaatacca gtcctacggg ccacggttgc     300
tgcaaatcag aaatttattg tagccaaagt cataaatgta gcgaatttag aagtatcatt     360
aggattaaac gtcgttaatg catatttagt ggcttataag gcaggaggta catcctattt     420
ctttaacgat cccgaatctt tggctgatgc aaaaaaatat cttttcacag acacaaagca     480
acaaacgcta tcatttactg gtagctatgc agatttTcta tctagggcaa acgtacacag     540
agaggatgtg gatttagggg tgctggcatt agataattac atatatatac ttcacaaaag     600
ttctcaacca gcagacattg ctaaacctct agttggtttt atcgaaatgg ttccagaggc     660
agcaagattc aaatatattg agaaaaaagt attaactcaa attagcgaaa cctttaggcc     720
gcgtggtgtc ataattagcc ttgagaacaa ctggggagac ctctcttatc aaatacagaa     780
atctgtaaat ggtatatttc tgaagccagt tcaattgcaa cgtgaaaact ataccaatat     840
cctagtgaac aatgtcaccc aagtaacagg tctcatggga gtcttgttga atgcagtcaa     900
ttacaaagtc tcaatggaag aaattatttt caactaccaa aagtggctgc catggcttta     960
atcctacttt tgctctatat atagtagcat aaataaagga caacaaattt agtattattg    1020
ttgttgtcca aacatgttgc caatgatata tgctatttcc ctgtaatatc ctcatctttc    1080
caatgtatga atatgatgat gtattatata tgacaaataa agtttctact agttcttaat    1140
```